United States Patent
Shibuya et al.

(10) Patent No.: US 6,797,717 B2
(45) Date of Patent: Sep. 28, 2004

(54) ANILIDE COMPOUNDS AND DRUGS CONTAINING THE SAME

(75) Inventors: Kimiyuki Shibuya, Tokorozawa (JP); Katsumi Kawamine, Higashimurayama (JP); Yukihiro Sato, Higashimurayama (JP); Toshiyuki Edano, Kawagoe (JP); Mitsuteru Hirata, Tsurugashima (JP); Chiyoka Ozaki, Tokyo (JP)

(73) Assignee: Kowa Company, Ltd. (JP)

( * ) Notice: Subject to any disclaimer, the term of this patent is extended or adjusted under 35 U.S.C. 154(b) by 45 days.

(21) Appl. No.: 10/034,669

(22) Filed: Dec. 19, 2001

(65) Prior Publication Data

US 2002/0099074 A1 Jul. 25, 2002

Related U.S. Application Data

(62) Division of application No. 09/381,850, filed as application No. PCT/JP98/01337 on Mar. 25, 1998, now Pat. No. 6,362,208.

(30) Foreign Application Priority Data

Mar. 25, 1997 (JP) ................................. 9-90146

(51) Int. Cl.[7] .................... A61K 31/435; C07D 471/04; C07D 513/04; C07D 498/04
(52) U.S. Cl. ..................... 514/301; 514/302; 514/303; 546/113; 546/114; 546/115; 546/116; 546/118
(58) Field of Search ................................. 546/113, 114, 546/115, 116, 118; 514/303, 301, 302

(56) References Cited

U.S. PATENT DOCUMENTS

| | | | |
|---|---|---|---|
| 3,720,686 A | | 3/1973 | Narayanan et al. |
| 4,088,768 A | | 5/1978 | Paget et al. |
| 4,384,881 A | | 5/1983 | Kuyama et al. |
| 4,509,971 A | | 4/1985 | Forster |
| 5,162,360 A | | 11/1992 | Creswell et al. |
| 5,290,801 A | | 3/1994 | Higley et al. |
| 5,700,819 A | | 12/1997 | Aotsuka et al. |
| 5,886,191 A | * | 3/1999 | Dominguez et al. ........ 548/490 |
| 5,939,462 A | | 8/1999 | Connell et al. |

FOREIGN PATENT DOCUMENTS

| DE | 2003841 | | 7/1970 |
|---|---|---|---|
| DE | 2239311 | | 2/1973 |
| EP | 0 372 455 A | | 6/1990 |
| FR | 2190426 | | 2/1974 |
| JP | 56-86170 | | 7/1981 |
| JP | 58-116489 | * | 7/1983 |

OTHER PUBLICATIONS

Czarnocka–Janowicz et al, Acta Poloniae (1979) 36(15) p. 529–537.*
Database Crossfire (Beilstein Institute), Beilstein Registry No. 828994, 843437, 849006 and Mathur KB et al., Indian J. Chem. 3:397–401 (1965).
J. Med. Chem., 14(11), 1075–7 (1971).
J. Med. Chem., 27(7), 914–7 (1984).
Chem. Abs. 94:65548 (1981).
Higley, C.A., et al., *Journal of Medicinal Chemistry*, 37(21):3511–3522 (1994).
Mahmoud, A.M., et al., *Journal of the Indian Chemical Society*, 59(5):675–677 (1982).

(List continued on next page.)

*Primary Examiner*—Bernard Dentz
(74) *Attorney, Agent, or Firm*—Peter F. Corless; John B. Alexander; Edwards & Angell, LLP

(57) ABSTRACT

The invention relates to a novel anilide compound and a pharmaceutical composition comprising the same. The invention relates to a compound represented by the following general formula:

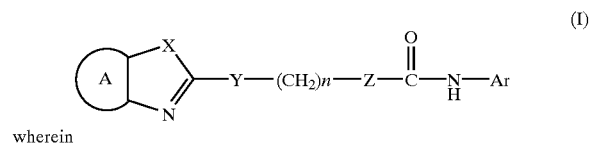

wherein

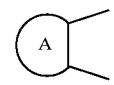

represents a divalent residue of benzene with a substituent(s), heterocycle-condensed benzene which may or may not have a substituent, pyridine which may or may not have a substituent, cyclohexane or naphthalene or 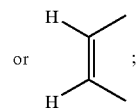 ;

Ar represents an aryl group which may or may not have a substituent,

X represents —NH—, oxygen atom or sulfur atom;

Y represents —NR$_4$—, oxygen atom, sulfur atom, sulfoxide or sulfone;

Z represents single bond or —NR$_5$—;

R$_4$ represents hydrogen atom, a lower alkyl group, an aryl group or a silylated lower alkyl group which may or may not have a substituent;

R$_5$ represents hydrogen atom, a lower alkyl group, an aryl group or a silylated lower alkyl group which may or may not have a substituent; and n represents an integer of 0 to 15.

The inventive compounds are useful in the form of pharmaceutical composition, specifically as acyl coenzyme A cholesterol acyltransferase (ACAT) inhibitor.

17 Claims, No Drawings

OTHER PUBLICATIONS

Walchshofer, N., et al., *European Jouranal of Medicinal Chemistry Chimica Therapeutica*, 21(1):59–64 (1986).

Database Crossfire Beilstein, "Online! Beilstein Institut zur Foerderung der Chemischen Wissenschaften, Frankfurt am Main, DE": Database accession No. 7764919 (Beilstein Registry Number).

Database Crossfire Beilstein, "Online! Beilstein Institut zur Foerderung der Chemischen Wissenschaften, Frankfurt am Main, DE": Database accession No. 4198734, 4201833 (Beilstein Registry Number).

Chemical Abstracts, vol. 64, No. 3520 (1966).

* cited by examiner

ANILIDE COMPOUNDS AND DRUGS CONTAINING THE SAME

This application is a divisional of application(s) application No. U.S. Ser. No. 09/381,850, filed on Dec. 6, 1999, now U.S. Pat. No. 6,362,208, which is a 371 of PCT/JP98/01337 filed on Mar. 25, 1998.

TECHNICAL FIELD

The present invention relates to a novel anilide compound and a pharmaceutical composition containing the same. More specifically, the invention relates to a compound represented by the general formula I:

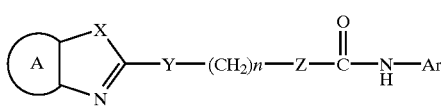

wherein

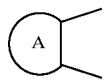

represents a divalent residue of benzene with a substituent(s), heterocycle-condensed benzene which may or may not have a substituent, pyridine which may or may not have a substituent, cyclohexane or naphthalene

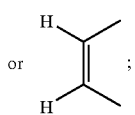

Ar represents an aryl group which may or may not have a substituent;
X represents —NH—, oxygen atom or sulfur atom;
Y represents —$NR_4$—, oxygen atom, sulfur atom, sulfoxide or sulfone;
Z represents single bond or —$NR_5$—;
$R_4$ represents hydrogen atom, a lower alkyl group, an aryl group or a silylated lower alkyl group which may or may not have a substituent;
$R_5$ represents hydrogen atom, a lower alkyl group, an aryl group or a silylated lower alkyl group which may or may not have a substituent; and
n represents an integer of 0 to 15;
a salt thereof or a solvated compound thereof and pharmaceutical compositions comprising these compounds.

BACKGROUND OF THE INVENTION

Following the transfer of the (Japanese) dietary life to European-style diets comprising high calorie and high cholesterol due to the improvement of the living standard and the increase of the ratio of aged people in the (Japanese) population, hyperlipidemia and arteriosclerotic diseases caused by hyperlipidemia have increased in number rapidly in recent years. The increase of these diseases is now one of the social problems (in Japan). Conventional pharmaceutical treatment of hyperlipidemia and arteriosclerosis has mainly targeted the reduction of lipid in blood as the etiology thereof. The treatment has never targeted arteriosclerotic lesions of themselves. Acyl coenzyme A cholesterol acyltransferase (ACAT) is the enzyme to catalyze the synthesis of cholesterol ester from cholesterol to play a significant role in the cholesterol metabolism and absorption in gastrointestinal tract. It is suggested that the inhibition of ACAT esterifying free cholesterol in the epidermal cell of small intestine works to inhibit cholesterol absorption from intestinal lumen and that the inhibition of cholesterol ester generation in liver owing to ACAT inhibition suppresses VLDL secretion from liver into blood stream, with the resultant action to decrease blood cholesterol. It is considered that many of conventional ACAT inhibitors function as anti-lipidemia agents to exert the action of decreasing blood cholesterol by allowing the inhibitors to react with the ACAT enzyme in small intestine and liver.

As ACAT inhibitors, for example, U.S. Pat. No. 4,716,175 describes 2,2 dimethyl-N-(2,4,6-trimethoxyphenyl) dodecanamide; and EP 372, 445 describes N'-(2,4-difluorophenyl)-N-[5-(4,5-diphenyl-1H-imidazol-2-ylthio) pentyl]-N-heptyl urea in the specification. However, many of these conventional ACAT inhibitors as anti-hyperlipidemia agents principally work to decrease blood cholesterol and are administered at large doses to permit sufficient exertion of the action. Due to the emergence of side effects including intestinal bleeding, intestinal disorders, diarrhea and liver disorders at high frequencies at clinical test stages, accordingly, the development of these agents for clinical practice has been very difficult.

Arteriosclerosis is a disease essentially involving unique features of hypertrophy of inner vascular membrane and lipid accumulation. Recent research works indicate that suppression of macrophage foaming essentially functioning for the formation of arteriosclerotic lesions possibly degenerates arteriosclerotic lesions. Macrophage-derived foam cell (storing cholesterol ester as lipid droplet inside the cell) is observed in arteriosclerotic lesions. It is indicated that macrophage foaming is deeply involved in the progress of the disease. Additionally, it is reported that ACAT activity is elevated in the wall of blood tubes in arteriosclerotic lesions, indicating that cholesterol ester is accumulated in the wall of blood tubes (Gyres, P. J. et al., Exp. Mole. Pathol., 44, 329–339 (1986)).

Due to the inhibition of cholesterol esterification by ACAT inhibitors, free cholesterol is generated inside cells and is then eliminated with high-density lipoprotein (HDL) to be transferred to and metabolized in liver (reverse transfer by HDL). It is suggested that the accumulation of cholesterol in diseased sites is thereby suppressed. Consequently, direct anti-arteriosclerotic action is exerted. A report tells that ACAT includes two sub-types, namely an ACAT type present in small intestine and an ACAT type, present in vascular wall (Quinoonen, P. M. et al., Biochem., 27, 7344–7350 (1988)). Conventional research works on ACAT inhibitors have mostly been carried out by using the ACAT type present in small intestine and liver (Tomoda, H. et al., J. Antibiotics 47, 148–153 (1994)). Based on the assumption that a pharmaceutical agent selectively inhibiting the ACAT type which presents in vascular wall may work as a therapeutic agent of arteriosclerosis with less side effects, the present inventors have synthetically produced such inhibitors and have carried out examinations on them.

DISCLOSURE OF THE INVENTION

So as to attain the object, the inventors have made investigations. Consequently, the inventors have found that a compound represented by the general formula I:

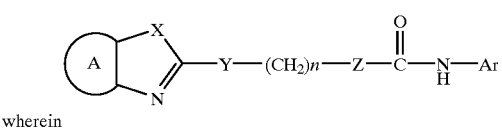

wherein

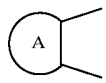

represents a divalent residue of benzene with a substituent(s), heterocycle-condensed benzene which may or may not have a substituent, pyridine which may or may not have a substituent, cyclohexane or naphthalene

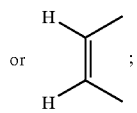

Ar represents an aryl group which may or may not have a substituent;
X represents —NH—, oxygen atom or sulfur atom;
Y represents —NR$_4$—, oxygen atom, sulfur atom, sulfoxide or sulfone;
Z represents single bond or —NR$_5$—;
R$_4$ represents hydrogen atom, a lower alkyl group, an aryl group or a silylated lower alkyl group which may or may not have a substituent;
R$_5$ represents hydrogen atom, a lower alkyl group, an aryl group or a silylated lower alkyl group which may or may not have a substituent; and
n represents an integer of 0 to 15;
a salt thereof or a solvated compound thereof exerts an excellent ACAT inhibitory action. Thus, the invention has been achieved.

The inventors have found that the inventive compounds exert ACAT inhibitory actions in an organ-specific manner and an action inhibiting the transfer of intra-cellular cholesterol and that the inventive compounds are particularly useful as anti-hyperlipidemia agents with an excellent action to reduce cholesterol in blood and as a prophylactic and therapeutic agent of arteriosclerosis with an action to suppress macrophage foaming.

Thus, the compound represented by the general formula I, a salt thereof or a solvated product thereof is provided in accordance with the invention.

Additionally, the invention provides pharmaceutical compositions comprising the compound represented by the general formula I, a salt thereof or a solvated product thereof, together with carriers pharmaceutically acceptable.

Still additionally, the invention provides the compounds shown as the above formula I, salts thereof or solvated compounds thereof, and ACAT inhibitors, agents inhibiting intra-cellular cholesterol transfer, blood cholesterol-reducing agents, or macrophage foaming-suppressing agents. In other words, the invention provides therapeutic and prophylactic agents of diseases including hyperlipidemia, arteriosclerosis, arteriosclerosis of carotid and cerebral arteries, cerebrovascular diseases, ischemic cardiac diseases, coronary arteriosclerosis, nephrosclerosis, arteriosclerotic nephrosclerosis, arteriocapillary sclerotic nephrosclerosis, malignant nephrosclerosis, ischemic intestinal diseases, acute mesenteric blood tube occlusion, chronic intestinal angina, ischemic colitis, aortic aneurysm and occlusive arteriosclerosis (ASO).

As compounds similar to the compound of the formula I, 3-(benzothiazol-2-ylthio)-N-(phenyl)propanamide and 3-(benzoxazol-2-ylthio)-N-(phenyl)propanamide are disclosed in J. Chem. Eng. Data, 27, 207 (1982) and Fungitsidy, Ed. Melnilov, N. N. Izd. Fan Uzb. SSR: Tashkent, USSR. 82–88 (1980), respectively. However, it has absolutely never been known that these compounds exert ACAT inhibitory actions.

BEST MODE FOR CARRYING OUT THE INVENTION

Preferable examples of the compound represented by the general formula I in accordance with the invention include a compound represented by the following formula II, a salt thereof or a solvated product thereof, and a compound represented by the following formula III, a salt thereof or a solvated product thereof:

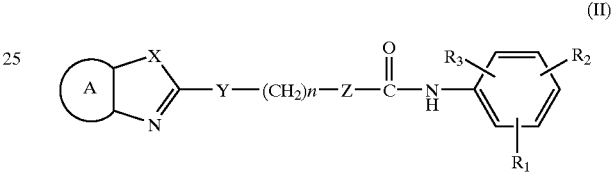

wherein

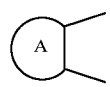

represents a divalent residue of benzene with a substituent(s), heterocycle-condensed benzene which may or may not have a substituent, pyridine which may or may not have a substituent, cyclohexane or naphthalene X represents —NH—, oxygen atom or sulfur atom;

Y represents —NR$_4$—, oxygen atom, sulfur atom, sulfoxide or sulfone;

Z represents single bond or —NR$_5$—,

R$_1$, R$_2$ and R$_3$ may be the same or different and represent hydrogen atom, a lower alkyl group, a lower alkoxyl group, halogen atom, hydroxyl group, phosphate group, sulfonamide group, or amino group which may or may not have a substituent; otherwise, any combination of two of R$_1$, R$_2$ and R$_3$ represents an alkylene dioxy group;

R$_4$ represents hydrogen atom, a lower alkyl group, an aryl group or a silylated lower alkyl group which may or may not have a substituent;

$R_5$ represents hydrogen atom, a lower alkyl group, an aryl group or a silylated lower alkyl group which may or may not have a substituent; and n represents an integer of 0 to 15;

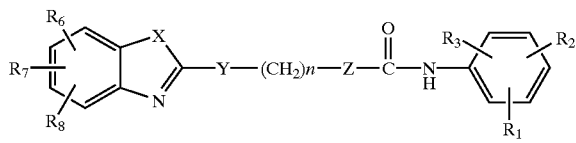

wherein

X represents —NH—, oxygen atom or sulfur atom;

Y represents —$NR_4$—, oxygen atom, sulfur atom, sulfoxide or sulfone;

Z represents single bond or —$NR_5$—;

$R_1$, $R_2$ and $R_3$ may be the same or different and represent hydrogen atom, a lower alkyl group, a lower alkoxyl group, halogen atom, hydroxyl group, phosphate group, sulfonamide group, or amino group which may or may not have a substituent; otherwise, any combination of two of $R_1$, $R_2$ and $R_3$ represents alkylene dioxy group;

$R_4$ represents hydrogen atom, a lower alkyl group, an aryl group or a silylated lower alkyl group which may or may not have a substituent;

$R_6$, $R_7$ and $R_8$ may be the same or different and represent hydrogen atom, a lower alkyl group which may or may not have a substituent, a lower alkoxyl group which may or may not have a substituent, halogen atom, hydroxyl group, carboxyl group, an alkoxycarbonyl group which may or may not have a substituent, an alkylcarbonyloxy group which may or may not have a substituent, an alkylcarbonyl group which may or may not have a substituent, carbamoyl group which may or may not have a substituent, a hydroxyalkyl group, phosphate group, cyano group, nitro group, sulfonamide group, amino group which may or may not have a substituent, an aminoalkyl group which may or may not have a substituent, or a heterocyclic residue; otherwise, any combination of two of $R_6$, $R_7$ and $R_8$ represents an alkylene dioxy group, provided that $R_6$, $R_7$ and $R_8$ never simultaneously represent hydrogen atom;

and n represents an integer of 0 to 15. More preferable is a compound represented by the following general formula IV, a salt thereof or a solvated product thereof:

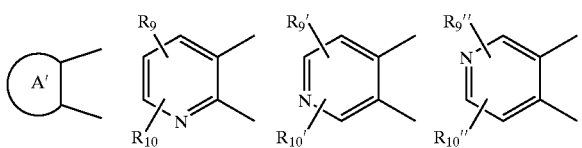

wherein represents

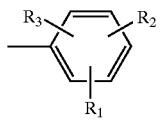 or

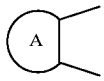

X represents —NH—, oxygen atom or sulfur atom;

Y represents —$NR_4$—, oxygen atom, sulfur atom, sulfoxide or sulfone;

Z represents single bond or —$NR_5$—;

$R_1$, $R_2$ and $R_3$ may be the same or different and represent hydrogen atom, a lower alkyl group, a lower alkoxyl group, halogen atom, hydroxyl group, phosphate group, sulfonamide group, or amino group which may or may not have a substituent; otherwise, any combination of two of $R_1$, $R_2$ and $R_3$ represents an alkylene dioxy group;

$R_4$ represents hydrogen atom, a lower alkyl group, an aryl group or a silylated lower alkyl group which may or may not have a substituent;

$R_5$ represents hydrogen atom, a lower alkyl group, an aryl group or a silylated lower alkyl group which may or may not have a substituent;

$R_9$, $R_{10}$, $R_9'$, $R_{10}'$, $R_9''$, $R_{10}''$, $R_9'''$, and $R_{10}'''$ may be the same or different and represent hydrogen atom, a lower alkyl group which may or may not have a substituent, a lower alkoxyl group which may or may not have a substituent, halogen atom, hydroxyl group, carboxyl group, an alkoxycarbonyl group which may or may not have a substituent, an alkylcarbonyloxy group which may or may not have a substituent, an alkylcarbonyl group which may or may not have a substituent, carbamoyl group which may or may not have a substituent, a hydroxyalkyl group, phosphate group, sulfonamide group, amino group which may or may not have a substituent, an aminoalkyl group which may or may not have a substituent, or a heterocyclic residue; otherwise, any combination of two thereof represents an alkylene dioxy group;

and n represents an integer of 0 to 15.

Ar in the general formula I represents an aryl group which may or may not have a substituent; a specifically preferable group is the following group:

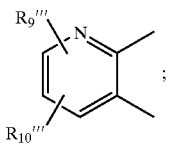

wherein $R_1$, $R_2$ and $R_3$ may be the same or different and represent hydrogen atom, a lower alkyl group, a lower alkoxyl group, halogen atom, hydroxyl group, phosphate group, sulfonamide group, or amino group which may or may not have a substituent; otherwise, any combination of two of $R_1$, $R_2$ and $R_3$ represents an alkylene dioxy group.

The following group in the general formula I represents a divalent residue of benzene with a substituent(s), heterocycle-condensed benzene which may or may not have a substituent, pyridine which may or may not have a substituent, cyclohexane or naphthalene, or

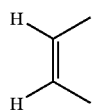

A divalent residue of benzene with a substituent preferably includes the group represented by the following formula:

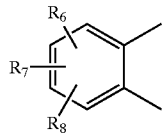

wherein $R_6$, $R_7$, and $R_8$ may be the same or different and represent hydrogen atom, a lower alkyl group which may or may not have a substituent, a lower alkoxyl group which may or may not have a substituent, halogen atom, hydroxyl group, carboxyl group, an alkoxycarbonyl group which may or may not have a substituent, an alkylcarbonyloxy group which may or may not have a substituent, an alkylcarbonyl group which may or may not have a substituent, carbamoyl group which may or may not have a substituent, a hydroxyalkyl group, phosphate group, cyano group, nitro group, sulfonamide group, amino group which may or may not have a substituent, an aminoalkyl group which may or may not have a substituent, or a heterocyclic residue; otherwise, any combination of two of $R_6$, $R_7$, and $R_8$ represents alkylene dioxy group, provided that $R_6$, $R_7$, and $R_8$ never simultaneously represent hydrogen atom.

A divalent residue of heterocycle-condensed benzene which may or may not have a substituent preferably includes the group represented by the following formula:

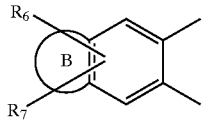

wherein $R_6$ and $R_7$ may be the same or different and represent those described above; the ring B represents a saturated or unsaturated heterocyclic group with at least one oxygen atom, nitrogen atom or sulfur atom in a 5- to 7-membered ring condensed with benzene ring.

A divalent residue of pyridine preferably includes the group represented by the formula:

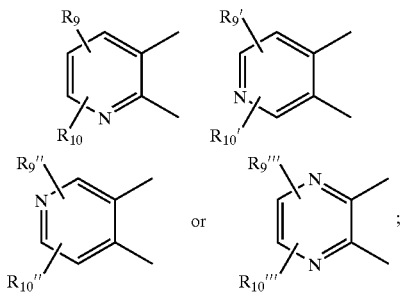

wherein $R_9$, $R_{10}$, $R_9'$, $R_{10}'$, $R_9''$, $R_{10}''$, $R_9'''$, and $R_{10}'''$ may be the same or different and represent hydrogen atom, a lower alkyl group which may or may not have a substituent, a lower alkoxyl group which may or may not have a substituent, halogen atom, hydroxyl group, carboxyl group, an alkoxycarbonyl group which may or may not have a substituent, an alkylcarbonyloxy group which may or may not have a substituent, an alkylcarbonyl group which may or may not have a substituent, carbamoyl group which may or may not have a substituent, a hydroxyalkyl group, phosphate group, sulfonamide group, amino group which may or may not have a substituent, an aminoalkyl group which may or may not have a substituent, or a heterocyclic residue; otherwise, any combination of two thereof represents an alkylene dioxy group.

The aryl group in $R_4$ and $R_5$ is preferably phenyl group, naphthyl group and the like; and these aryl groups may or may not have the substituents described above.

The lower alkyl group represented by each symbol in the general formula I preferably includes a linear or branched alkyl group with one to 15 carbon atoms, preferably one to 10 carbon atoms and more preferably one to 6 carbon atoms. For example, the lower alkyl group is preferably methyl group, ethyl group, n-propyl group, iso-propyl group, n-butyl group, iso-butyl group, tert-butyl group, n-pentyl group, n-hexyl group or the like. As the lower alkoxyl group, preference is given to an alkoxyl group comprising alkyl groups such as those described above. The alkoxycarbonyl group preferably contains the alkoxyl groups described above. The alkylcarbonyloxy group preferably contains the lower alkyl groups described above. The alkylcarbonyl group preferably contains the lower alkyl groups described above.

Additionally, the lower alkyl groups, the lower alkoxyl groups, the alkoxycarbonyl groups, the alkylcarbonyloxy groups, the alkylcarbonyl groups or the carbamoyl groups may or may not have substituents. These substituents may work as alternative substituents for each other; for example, alkoxy lower alkyl group, alkoxyalkoxyl group, lower alkoxyalkoxycarbonyl groups, alkoxycarbonyl-substituted alkyl group, alkoxycarbonyl-substituted alkoxyl group, alkoxycarbonyl-substituted alkoxycarbonyl group may be possible.

Still additionally, other substituents include for example halogen atoms such as chlorine atom and fluorine atom, hydroxyl group, silyl groups such as trimethylsilyl group, dimethyl t-butylsilyl group, and dimethylphenylsilyl group, saturated or unsaturated heterocyclic residues containing one or two or more oxygen atoms, nitrogen atoms or sulfur atoms in the ring thereof, such as oxethanyl group, tetrahydrofuryl group and pyrrolidinyl group. The alkylene dioxy group preferably contains a linear or branched alkylene group with one to 6 carbon atoms.

The halogen atom is preferably fluorine atom, chlorine atom, bromine atom or iodine atom or the like. The amino group may or may not be substituted with one or two substituents. The substituents for the amino group preferably include lower alkyl groups such as those described above, aryl groups such as phenyl group and naphthyl group, and aralkyl groups such as benzyl group and phenethyl group; and the aromatic rings thereof may or may not be substituted with lower alkyl groups and lower alkoxyl groups such as those described above, additionally. Furthermore, two of the substituents for the amino group together may form a 5- to 7-membered ring which may or may not contain oxygen, sulfur or nitrogen. The heterocyclic residues are preferably of a monocycle, a polycycle or a condensed ring comprising a 5- to 7-membered ring, saturated or unsaturated, containing one or two hetero-atoms, preferably one to four hetero-atoms such as oxygen atom, nitrogen atom or sulfur atom; and these heterocyclic residues may or may not be substituted with the lower alkyl groups, the lower alkoxyl groups, the alkylene dioxy groups, halogen atom, the amino group, and substituted amino groups. The heterocyclic residues include for example tetrazolyl group, 2-, 4- or 5-imidazolyl group, 3- or 4-pyrazolyl group, 2-, 4- or 5-oxazolyl group, 2-, 4- or 5-thiazolyl group, oxazolin-2-, 4- or 5-yl group, [1,3]-dioxylan-2- or 4-yl group, and these heterocyclic residues substituted with lower alkyl groups such as methyl group and ethyl group.

The acid addition salt of the compound I in accordance with the invention includes for example salts thereof with inorganic acids, such as hydrochloride salt, sulfate salt, nitrate salt, and phosphate salt, and salts thereof with organic acids, such as methanesulfonate salt, maleate salt, fumarate salt and citrate salt.

Additionally, the solvated product thereof is prepared by adding solvents used for the production and purification thereof, for example water and alcohol, to the compound I, with no specific limitation, as long as the solvated product never disadvantageously affects the ACAT inhibitory action. The solvated product is preferably a hydrated product thereof.

The invention relates to the compound represented by the general formulae I, II, III or IV, a salt thereof or a solvated product thereof, and a pharmaceutical composition comprising the same and a pharmaceutically acceptable carrier. More specifically, the invention relates to a pharmaceutical composition as ACAT inhibitor, intra-cellular cholesterol transfer inhibitory agent, blood cholesterol-reducing agent, or macrophage foaming-suppressing agent. Still furthermore, the invention relates to a pharmaceutical composition as a prophylactic and therapeutic agent of hyperlipidemia, arteriosclerosis, cerebrovascular diseases, ischemic cardiac disorders, ischemic colon disorders or aortic aneurysm.

Still additionally, the invention relates to a method for therapeutically treating diseases due to ACAT, intra-cellular cholesterol transfer, blood cholesterol or macrophage foaming and a method for therapeutically treating hyperlipidemia, arteriosclerosis, cerebrovascular diseases, ischemic cardiac disorders, ischemic colon disorders or aortic aneurysm, comprising administering a therapeutically effective dose of the compound represented by the general formula I, II, III or IV, a salt thereof or a solvated product thereof.

Still more additionally, the invention relates to the use of the compound represented by the general formula I, II, III or IV, a salt thereof or a solvated compound thereof for producing an ACAT inhibitor, an agent inhibiting intra-cellular cholesterol transfer, an agent reducing blood cholesterol, or an agent suppressing macrophage foaming and the use thereof for therapeutically treating hyperlipidemia, arteriosclerosis, cerebrovascular diseases, ischemic cardiac disorders, ischemic colon disorders or aortic aneurysm.

The compound I can be produced by a variety of known methods, with no specific limitation. The compound I can be produced for example by the following steps.

1. Process of Producing Compound with Z Representing Single Bond (1) Following the reaction scheme described hereinbelow, reaction of carboxylic acid represented by the general formula V or a reactive derivative thereof, for example acid halide, with amine represented by the general formula VI generates an amide derivative represented by the general formula VII. Reaction of the resulting compound represented by the general formula VII with a compound represented by the general formula VIII can generate the objective compound I' with Z representing single bond:

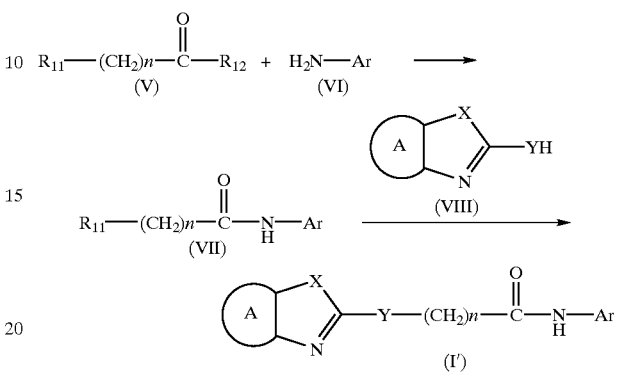

wherein $R_{11}$ represents an elimination group; and $R_{12}$ represents a residue of a reactive derivative of hydroxyl group or carboxyl group.

A general method for peptide synthesis is applicable to the reaction of the compound V with the compound VI. $R_{11}$ in the general formula V is preferably halogen atom such as chlorine atom and bromine atom; and the residue of a reactive derivative as represented by $R_{12}$ is preferably an acid anhydride residue of mesyl acid, tosyl acid, acetic acid and pivalic acid. For example, the two compounds react together in the presence of a condensing agent in a solvent whereby the objective compound can be recovered. As the condensing agent, use may be made of for example 1-(3'-dimethylaminopropyl)-3-ethylcarbodiimide (WSC) and 1,3-dicyclohexylcarbodiimide (DCC), singly or in combination with 1-hydroxybenzotriazole (HOBt) and N-hydroxysuccinimide (HOSU). As the solvent, use can be made of for example dimethylformamide, methylene chloride, chloroform, tetrahydrofuran and toluene, singly or in combination thereof, with no specific limitation.

The reaction varies, depending on the raw materials to be used; the reaction proceeds generally at 0 to 100° C., preferably around ambient temperature, for one to 30 hours, preferably 10 to 20 hours. When a highly reactive carboxylic halogenide is used as the compound V, the compound V is allowed to react with the compound VI in the presence of bases, for example triethylamine, 4-dimethylaminopyridine or N-methylmorpholine by general methods.

The starting compounds V and VI are known compounds; the compound V can be produced by a method comprising oxidizing haloalkyl alcohol with Jones reagents and the like, while the compound VI can be produced by a method comprising subjecting a nitrobenzene derivative to a reductive reaction including contact reduction to prepare a corresponding aniline derivative.

The reaction of the compound VII thus recovered by the aforementioned methods with the compound VIII can be progressed in the presence or absence of bases in a solvent. As the solvent, use may be made of those described above, including bases for example inorganic bases including alkali metal hydroxides such as sodium hydroxide and potassium hydroxide, alkali metal carbonates such as sodium carbonate and potassium carbonate, and alkali metal hydrogen carbonates such as sodium hydrogen carbonate and potassium hydrogen carbonate; and organic bases such as pyridine, triethylamine, N,N-diisopropylethylamine, N-methylmorpholine, and N,N-dimethylaniline.

(2) Following the reaction represented by the following scheme, the compound represented by the general formula VIII is allowed to react with free carboxylic acid or an inactive carboxylic acid form as the compound represented by the general formula V, to recover a carboxylate derivative represented by the general formula IX. The resulting compound represented by the general formula IX or a reactive derivative thereof, for example an acid halide, is allowed to react with an aniline derivative represented by the general formula VI, to generate the objective compound I' with Z representing single bond:

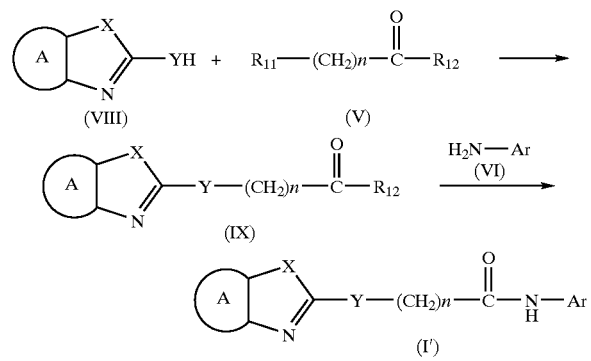

wherein $R_{11}$ represents an elimination group and $R_{12}$ represents a residue of a reactive derivative of hydroxyl group or carboxyl group.

The reaction of the compound VIII with the compound V can be facilitated by the second step described above in (1).

The reaction is progressed by using potassium hydroxide as the base and ethanol as the solvent, preferably. The reaction of the compound VI with the compound III can be facilitated by the first step described above in (1). If necessary, $R_{12}$ in the compound IX can be modified as a reactive derivative residue, prior to the reaction.

2. Process of Producing Compound I" with Z Representing —NH—.

The compound represented by the general formula I wherein Z represents —NH— can be produced by a variety of methods. The compound can be produced by the method represented by the following reaction scheme.

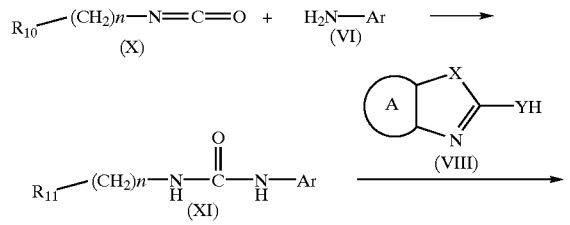

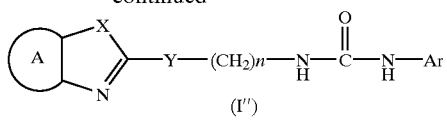

By allowing an isocyanate derivative represented by the general formula X to react with an aniline derivative represented by the general formula VI, a urea derivative represented by the general formula XI can be recovered.

By allowing the compound VIII to react with the resulting urea derivative, the objective compound I" with Z representing —NH— can be recovered.

As regards the reaction of the compound X with the compound VI at the first step, reaction of one to 2 equivalents of the compound VI with one equivalent of the compound X in a solvent can yield the compound XI. As the solvent, preferably, use is made of for example methylene chloride, chloroform, ether, tetrahydrofuran, toluene, xylene, and dimethylformamide, with no specific limitation. The reaction progresses at 0° C. to the boiling point of the solvent used, over one to 24 hours.

The isocyanate derivative represented by the general formula X is a known compound and can be produced, for example by a method comprising allowing the carboxylic acid as the compound X to react with diphenylphosphoryl azide in the presence of a base (the method by Shioiri et al.) and a method en route of acid azide prepared by allowing an acid halide as the compound V to react with sodium azide.

The reaction of the compound XI with the compound VIII can be facilitated according to the second step of the reaction 1.1.

The intermediates and objective compounds as recovered in the individual reactions can be isolated and purified by purification methods routinely used in synthetic organic chemistry, for example filtration, extraction, rinsing, drying, concentration, recrystallization, and various chromatographic means. Furthermore, the intermediates can be subjected, with no purification, to next reaction.

The resulting compound I can be modified as an acid addition salt in a conventional manner.

Alternatively, solvated products thereof with solvents such as reaction solvent and recrystallization solvent, specifically hydrated product thereof, may also be recovered.

Specific examples of the compounds recovered by the production methods are shown in Tables 1, 2, 3, 4, 5, 6, 7 and 8.

TABLE 1

(I) Structure: A-ring fused with X/N oxazole/imidazole — Y—(CH₂)n—Z—C(=O)—NH—Ar

| Example No. | A | X | Y | Z | n | Ar |
|---|---|---|---|---|---|---|
| 1 | 2,3-pyridinyl | O | S | * | 5 | 2,6-diisopropylphenyl |
| 2 | 3,4-pyridinyl | O | S | * | 5 | 2,6-diisopropylphenyl |
| 3 | 3,4-pyridinyl (N at 1) | O | S | * | 5 | 2,6-diisopropylphenyl |
| 4 | 2,3-pyridinyl (N at 1) | O | S | * | 5 | 2,6-diisopropylphenyl |
| 5 | 2,3-pyridinyl | NH | S | * | 5 | 2,6-diisopropylphenyl |
| 6 | 3,4-pyridinyl | NH | S | * | 5 | 2,6-diisopropylphenyl |
| 7 | 2,3-pyridinyl | O | S | * | 8 | 2,6-diisopropylphenyl |
| 8 | 3,4-pyridinyl | O | S | * | 8 | 2,6-diisopropylphenyl |
| 9 | 3,4-pyridinyl | O | S | * | 8 | 2,6-diisopropylphenyl |
| 10 | 2,3-pyridinyl | O | S | * | 8 | 2,6-diisopropylphenyl |
| 11 | 6-methyl-2,3-pyridinyl | O | S | * | 5 | 2,6-diisopropylphenyl |

TABLE 1-continued
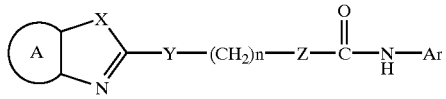
(I)
| Example No. | A 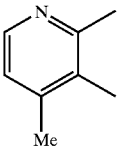 | X | Y | Z | n | Ar |
|---|---|---|---|---|---|---|
| 12 |  | O | S | * | 5 | 2,6-diisopropylphenyl |
*: Single Bond
TABLE 2
| Example No. | A 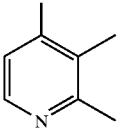 | X | Y | Z | n | Ar |
|---|---|---|---|---|---|---|
| 13 | 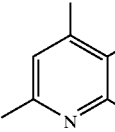 | O | S | * | 5 | 2,6-diisopropylphenyl |
| 14 | 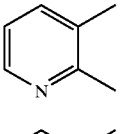 | O | S | * | 5 | 2,6-diisopropylphenyl |
| 15 | 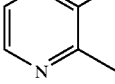 | O | NR* | * | 5 | 2,6-diisopropylphenyl |
| 16 | 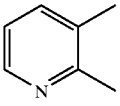 | O | NMe | * | 5 | 2,6-diisopropylphenyl |
| 17 | 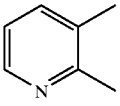 | O | NH | * | 5 | 2,6-diisopropylphenyl |
| 18 | 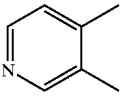 | O | NH | * | 5 | 2,6-diisopropylphenyl |
| 19 | 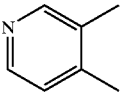 | O | NH | * | 5 | 2,6-diisopropylphenyl |

TABLE 2-continued

| Example No. | A | X | Y | Z | n | Ar |
|---|---|---|---|---|---|---|
| 20 | pyridine with 2,3-dimethyl | O | NH | * | 5 | 2,6-diisopropylphenyl |
| 21 | pyridine with 2,3-dimethyl | S | S | * | 5 | 2,6-diisopropylphenyl |
| 22 | phenyl with 2,3-dimethyl, OH | O | S | * | 5 | 2,6-diisopropylphenyl |
| 23 | phenyl with 2,3-dimethyl, OAc | O | S | * | 5 | 2,6-diisopropylphenyl |
| 24 | phenyl with 2,3-dimethyl, COOMe | O | S | * | 5 | 2,6-diisopropylphenyl |
| 25 | phenyl with 2,3-dimethyl, COOH | O | S | * | 5 | 2,6-diisopropylphenyl |

*: Single Bond
R*: dimethylphenylsilylmethyl

TABLE 3

| Example No. | A | X | Y | Z | n | Ar |
|---|---|---|---|---|---|---|
| 26 | phenyl with 2,3-dimethyl, CH$_2$OH | O | S | * | 5 | 2,6-diisopropylphenyl |
| 27 | phenyl with 2,3-dimethyl, CH$_2$NMe$_2$ | O | S | * | 5 | 2,6-diisopropylphenyl |

TABLE 3-continued
| Example No. | A | X | Y | Z | n | Ar |
|---|---|---|---|---|---|---|
| 28 |  | O | S | * | 5 | 2,6-diisopropylphenyl |
| 29 | 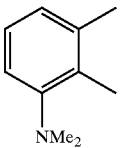 | O | S | * | 5 | 2,6-diisopropylphenyl |
| 30 | 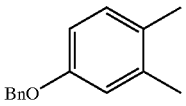 | O | S | * | 5 | 2,6-diisopropylphenyl |
| 31 | 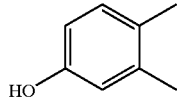 | O | S | * | 8 | 2,6-diisopropylphenyl |
| 32 | 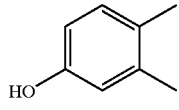 | O | S | * | 5 | 2,6-diisopropylphenyl |
| 33 | 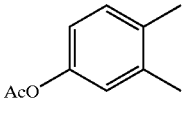 | O | S | * | 8 | 2,6-diisopropylphenyl |
| 34 | 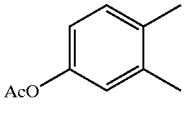 | O | S | * | 5 | 2,6-diisopropylphenyl |
| 34 | 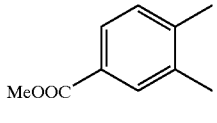 | O | S | * | 5 | 2,6-diisopropylphenyl |
| 36 | 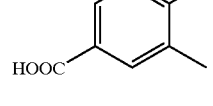 | O | S | * | 5 | 2,6-diisopropylphenyl |
| 37 | 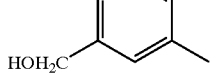 | O | S | * | 5 | 2,6-diisopropylphenyl |
| 38 | 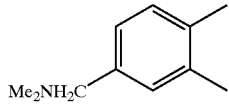 | O | S | * | 5 | 2,6-diisopropylphenyl |

TABLE 3-continued
| Example No. |  (A) | X | Y | Z | n | Ar |
|---|---|---|---|---|---|---|
| 39 | 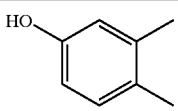 | O | S | * | 5 | 2,6-diisopropylphenyl |
*: Single Bond
TABLE 4
| Example No. |  (A) | X | Y | Z | n | Ar |
|---|---|---|---|---|---|---|
| 40 | 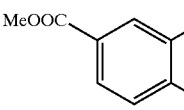 | O | S | * | 5 | 2,6-diisopropylphenyl |
| 41 | 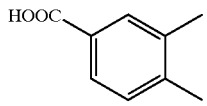 | O | S | * | 5 | 2,6-diisopropylphenyl |
| 42 | 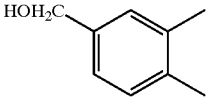 | O | S | * | 5 | 2,6-diisopropylphenyl |
| 43 | 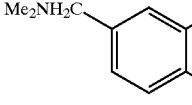 | O | S | * | 5 | 2,6-diisopropylphenyl |
| 44 | 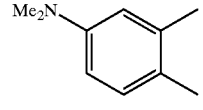 | O | S | * | 5 | 2,6-diisopropylphenyl |
| 45 | 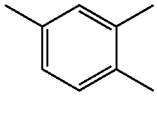 | O | S | * | 5 | 2,6-diisopropylphenyl |
| 46 | 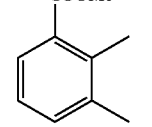 | O | S | * | 5 | 2,6-diisopropylphenyl |
| 47 | 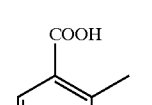 | O | S | * | 5 | 2,6-diisopropylphenyl |
| 48 | 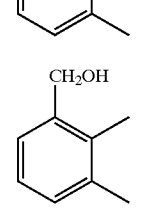 | O | S | * | 5 | 2,6-diisopropylphenyl |

TABLE 4-continued
| Example No. | A  | X | Y | Z | n | Ar |
|---|---|---|---|---|---|---|
| 49 | 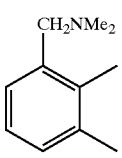 CH₂NMe₂ | O | S | * | 5 | 2,6-diisopropylphenyl |
| 50 | 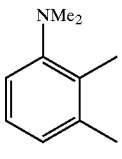 NMe₂ | O | S | * | 5 | 2,6-diisopropylphenyl |
| 51 | 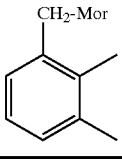 CH₂-Mor | O | S | * | 5 | 2,6-diisopropylphenyl |
*: Single Bond
TABLE 5
| Example No. | A  | X | Y | Z | n | Ar |
|---|---|---|---|---|---|---|
| 52 | 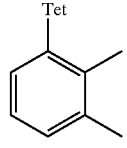 Tet | O | S | * | 5 | 2,6-diisopropylphenyl |
| 53 | 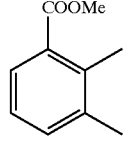 COOMe | S | S | * | 1 | 2,6-diisopropylphenyl |
| 54 | 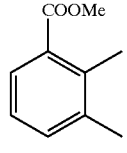 COOMe | O | S | * | 8 | 2,6-diisopropylphenyl |
| 55 | 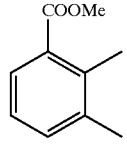 COOMe | O | S | —NH— | 7 | 2,6-diisopropylphenyl |
| 56 | 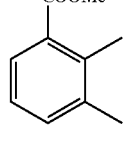 COOMe | O | SO | —NH— | 7 | 2,6-diisopropylphenyl |

TABLE 5-continued

| Example No. | A | X | Y | Z | n | Ar |
|---|---|---|---|---|---|---|
| 57 | Me₂N-phenyl (3,4-dimethyl) | O | S | —NH— | 7 | 2,6-diisopropylphenyl |
| 58 | COOMe-phenyl (2,3-dimethyl) | O | SO₂ | * | 5 | 2,6-diisopropylphenyl |
| 59 | COO(CH₂)₂NMe₂-phenyl (2,3-dimethyl) | O | S | * | 5 | 2,6-diisopropylphenyl |
| 60 | CONH(CH₂)₂NMe₂-phenyl (2,3-dimethyl) | O | S | * | 5 | 2,6-diisopropylphenyl |
| 61 | COOMe-phenyl (2,3-dimethyl) | O | S | * | 5 | 2,4,6-trifluorophenyl |
| 62 | COOMe-phenyl (2,3-dimethyl) | O | S | * | 5 | 2,4,6-trimethoxy-phenyl |

*: Single Bond

TABLE 6

| Example No. | A | X | Y | Z | n | Ar |
|---|---|---|---|---|---|---|
| 63 | MeOOC-phenyl (3,4-dimethyl) | NH | S | * | 5 | 2,6-diisopropylphenyl |
| 64 | Me₂N-phenyl (3,4-dimethyl) | NH | S | * | 5 | 2,6-diisopropylphenyl |
| 65 | Me₂N-phenyl (3,4-dimethyl) | S | S | * | 5 | 2,6-diisopropylphenyl |

TABLE 6-continued

| Example No. | A | X | Y | Z | n | Ar |
|---|---|---|---|---|---|---|
| 66 | (trans-1,2-dimethylcyclohexane) | O | S | * | 5 | 2,6-diisopropylphenyl |
| 67 | (cis-1,2-dimethylcyclohexane) | O | S | * | 5 | 2,6-diisopropylphenyl |
| 68 | cis-CH=CH (2-butene) | NH | S | * | 5 | 2,6-diisopropylphenyl |
| 69 | 2,3-dimethylnaphthalene | O | S | * | 5 | 2,6-diisopropylphenyl |
| 70 | PhMe₂Si-CH₂-O-(3-methylphenyl) | O | S | * | 5 | 2,6-diisopropylphenyl |
| 71 | 3-COOMe-2,3-dimethylphenyl | O | S | N(CH₃)(CH₂)₈CH₃ | 6 | 2,6-diisopropylphenyl |
| 72 | 2,3-dimethylpyridine | O | S | N(CH₃)(CH₂)₆CH₃ | 6 | 2,6-diisopropylphenyl |
| 73 | 3-CF₃-2,3-dimethylphenyl | O | S | * | 1 | 2,6-diisopropylphenyl |
| 74 | 3-CF₃-2,3-dimethylphenyl | O | S | * | 5 | 2,6-diisopropylphenyl |
| 75 | 3-CF₃-2,3-dimethylphenyl | O | S | * | 8 | 2,6-diisopropylphenyl |

*: Single Bond

TABLE 7

| Example No. | A (structure) | X | Y | Z | n | Ar |
|---|---|---|---|---|---|---|
| 76 | 4-F₃C, 2,3-dimethylphenyl | O | S | * | 5 | 2,6-diisopropylphenyl |
| 77 | 3-C(CH₃)₃, 2-methylphenyl (2,3-dimethyl with C(CH₃)₃) | O | S | * | 5 | 2,6-diisopropylphenyl |
| 78 | 3,4,5-tri(MeO), 2-methylphenyl | O | S | * | 5 | 2,6-diisopropylphenyl |
| 79 | 3-COOEt, 2-methylphenyl | O | S | * | 5 | 2,6-diisopropylphenyl |
| 80 | 3-COOCH₂OMe, 2-methylphenyl | O | S | * | 5 | 2,6-diisopropylphenyl |
| 81 | 3-COOC(CH₃)₃, 2-methylphenyl | O | S | * | 5 | 2,6-diisopropylphenyl |
| 82 | 3-COOCH₂COOC(CH₃)₃, 2-methylphenyl | O | S | * | 5 | 2,6-diisopropylphenyl |
| 83 | (substituted benzoate ester) | O | S | * | 5 | 2,6-diisopropylphenyl |

TABLE 7-continued

| Example No. | A (structure) | X | Y | Z | n | Ar |
|---|---|---|---|---|---|---|
| 84 | 4,4-dimethyl-oxazoline on 2,3-dimethylphenyl | O | S | * | 5 | 2,6-diisopropylphenyl |
| 85 | 1,3-dioxolane on 2,3-dimethylphenyl | O | S | * | 5 | 2,6-diisopropylphenyl |

*: Single Bond

TABLE 8

| Example No. | A (structure) | X | Y | Z | n | Ar |
|---|---|---|---|---|---|---|
| 86 | 4,5-dimethyl-1,3-dioxolane on 2,3-dimethylphenyl | O | S | * | 5 | 2,6-diisopropylphenyl |
| 87 | acetyl on 2,3-dimethylphenyl | O | S | * | 5 | 2,6-diisopropylphenyl |
| 88 | 1H-pyrazol-3-yl on 2,3-dimethylphenyl | O | S | * | 5 | 2,6-diisopropylphenyl |

TABLE 8-continued

| Example No. | [structure A] | X | Y | Z | n | Ar |
|---|---|---|---|---|---|---|
| 89 | [MeOOC-phenyl-COOMe with methyl] | O | S | * | 5 | 2,6-diisopropylphenyl |
| 90 | [isobenzofuranone with methyl] | O | S | * | 5 | 2,6-diisopropylphenyl |
| 91 | [HO-phenyl-COOMe with dimethyl] | O | S | * | 5 | 2,6-diisopropylphenyl |
| 92 | [dihydrobenzofuran with gem-dimethyl] | O | S | * | 5 | 2,6-diisopropylphenyl |

*: Single Bond

The inventive compound represented by the general formula I has an ACAT inhibitory action and/or an action inhibiting intra-cellular cholesterol transfer and is therefore useful as a therapeutic agent of hyperlipidemia or a therapeutic agent of arteriosclerosis in the field of clinical medicine. Particularly because the inventive compound exerts an action selectively inhibiting an ACAT type present in vascular wall, the inventive compound possibly exerts less side effects, compared with non-selective ACAT inhibitors, which is preferable as an effective ingredient of pharmaceutical agent.

The inventive pharmaceutical composition contains the compound represented by the general formula I, an acid addition salt thereof or a solvated product thereof as the effective ingredient. Singly or in combination with other pharmaceutically acceptable carriers such as excipients, binders and diluents, the effective ingredient can be prepared as dosage forms such as tablet, capsule, granule, powder, injection and suppository. These dosage forms can be produced according to known methods. For preparing an oral dosage form, the compound represented by the general formula I is formulated with an appropriate combination of excipients such as starch, mannitol and lactose, binders such as sodium carboxymethylcellulose and hydroxypropylcellulose, disintegrators such as crystal cellulose and carboxymethylcellulose, lubricants such as talc and magnesium stearate, and fluidity-enhancing agents such as light silicic anhydride.

The inventive pharmaceutical composition is administered orally or parenterally.

The dose of the inventive pharmaceutical composition varies, depending on the body weight, age, sex and diseased conditions of a patient. For an adult, generally, the compound represented by the general formula I is preferably administered at 1 to 1000 mg, preferably 5 to 200 mg per day in one to three dividend doses.

The ACAT inhibitory action of the inventive compound represented by the general formula I is tested in the following experimental examples.

Experimental Example 1

ACAT Inhibitory Action

In a conventional manner, microsome was prepared from the thoracic aorta of a rabbit fed with a 1% cholesterol diet for 8 weeks, which was then suspended in 0.15 M phosphate buffer, pH 7.4, to prepare an enzyme solution. An enzyme solution was prepared from a rabbit small intestine on normal diet, which was defined as an enzyme solution derived from small intestine.

The ACAT inhibitory activity was assayed by a modification of the method by J. G. Hyder, J. Lipid Res., 24, 1127–1134 (1983). More specifically, 2 µl of a test compound dissolved in dimethyl sulfoxide (DMSO) was added to 88 µl of 0.15 M phosphate buffer, pH 7.4 containing $^{14}$C-Oleoyl-CoA (40 µM, 60,000 dpm) and 2.4 mg/ml bovine serum albumin, for incubation at 37° C. for 5 minutes. 10 µl of an enzyme solution was added to the resulting solution for reaction at 37° C. for 5 days (small intestine-derived enzyme solution was subjected to reaction for 3 minutes). Subsequently, the reaction was terminated by adding 3 ml of chloroform/methanol (2/1) and 0.5 ml of 0.04 N hydrochloric acid to the reaction solution, to extract lipid. The solvent layer was concentrated and dried, which was then dissolved in hexane and spotted on a TLC plate (manufactured by Merck, Co.). The plate was eluted with hexane:ether:acetic acid (75:25:1). The radioactivity of the resulting cholesterol ester fraction was assayed by BAS 2000 (manufactured by Fuji Photo Film, Co., Ltd.). Compared with the radioactivity of a control prepared by single addition of DMSO, $IC_{50}$ was determined. The results are shown in Table 9.

TABLE 9

| A | B | C | D |
|---|---|---|---|
| 1 | 0.025 | 0.14 | 5.6 |
| 6 | 0.60 | 1.0 | 1.7 |
| 27 | 0.042 | 0.32 | 7.6 |
| 28 | 0.029 | 0.12 | 4.1 |
| 29 | 0.042 | 0.054 | 1.3 |
| 34 | 0.070 | 0.21 | 3.0 |
| 38 | 0.25 | 0.17 | 0.7 |
| 46 | 0.032 | 0.33 | 10.3 |
| 50 | 0.036 | 0.077 | 2.1 |
| Control 1 | 0.45 | 0.87 | 1.9 |
| Control 2 | 0.047 | 0.13 | 2.8 |
| Control 3 | 0.034 | 0.056 | 1.7 |
| Control 4 | 0.026 | 0.037 | 1.4 |

A: Test Compounds(Compounds of Examples)
B: $IC_{50}$ ($\mu$M) of vascular wall-derived enzyme
C: $IC_{50}$ ($\mu$M) of small intestine-derived enzyme
D: $IC_{50}$ ($\mu$M) (for small intestine-derived enzyme)/$IC_{50}$ ($\mu$M) (for vascular wall-derived enzyme)

Experimental Example 2

ACAT Inhibitory Action (Anti-foaming Action) in J1744 Cells and HepG2 Cells

J774 cells or HepG2 cells were inoculated on a 24-well plate; J774 cells and HepG2 cells were cultured in DMEM and MEM culture broths (each of the broths containing 10% calf fetus serum), respectively, in a 5% $CO_2$ incubator at 37° C. for 24 hours. These culture broths were individually exchanged to 0.5 ml of DMEM and MEM containing 10 $\mu$g/ml 25-OH cholesterol and a test sample, for 18-hr culturing. After discarding the culture media, the resulting cultures were rinsed twice with PBS and extracted with 1.5 ml of hexane:isopropanol (3:2), for concentration and drying. The extracts were dissolved in isopropanol containing 0.2 ml of 10% Triton X-100, to assay total cholesterol (TC) and free cholesterol (FC) by using Cholesterol E Test WAKO (manufactured by Wako Pure Chemicals, Co.) and Free Cholesterol E Test Wako (manufactured by Wako Pure Chemicals, Co.). After extraction, cellular residue was solubilized in 0.25 ml of 2 N NaOH at 37° C. for 30 minutes, to assay protein by BCA Protein Assay Reagent (Pierce). Based on the difference between TC and FC, cholesterol ester was calculated per protein, to determine $IC_{50}$, compared with the calculated control $IC_{50}$ value. The results are shown in Table 10.

TABLE 10

| A | B | C | D |
|---|---|---|---|
| 1 | 1.30 | 4.1 | 3.2 |
| 6 | 10.0 | 10.0 | 1.0 |
| 27 | 1.31 | — | — |
| 28 | 0.47 | 0.42 | 0.9 |
| 29 | 0.26 | 1.9 | 7.3 |
| 34 | 0.60 | 8.15 | 13.5 |
| 38 | 1.83 | — | — |
| 46 | 0.098 | 29.76 | 303.4 |
| 50 | 0.82 | 0.72 | 0.9 |
| 75 | 0.012 | 0.089 | 7.4 |
| 88 | 1.64 | 10.0 | 6.1 |
| Control 1 | 0.56 | 5.30 | 9.5 |
| Control 2 | 0.58 | 1.1 | 1.9 |
| Control 3 | 0.32 | 1.3 | 4.3 |
| Control 4 | 0.12 | 0.75 | 6.3 |

A: Test Compounds(Compounds of Examples)
B: $IC_{50}$ ($\mu$M) of J774-derived enzyme
C: $IC_{50}$ ($\mu$M) of HepG2-derived enzyme
D: $IC_{50}$ (HepG2)/$IC_{50}$(J774)

The following compounds were tested as control compounds by the same method. The results are shown in Tables 7 and 8.
Control 1:
5-[2-(2-(4-fluorophenyl)ethyl)-3-(1-methyl-1H-imidazol-2-yl)-2H-1-benzopyran-6-yl]oxy-2,2-dimethyl-N-(2,6-diisopropylphenyl)pentanamide (WO92/09582)
Control 2:
(+)-(S)-2-[5-(3,5-dimethylpyrazol-1-yl)pentasulfinyl]-4,5-diphenylimidazole (EP, A, 523941)
Control 3:
N-(2,2,5,5-tetramethyl-1,3-dioxan-4-ylcarbonyl)-β-alanine 2(S)-[N'-(2,2-dimethylpropyl)-N'-nonylureido]-1(S)-cyclohexyl ester (EP, A, 421441)
Control 4:
[5-(4,5-diphenyl-1H-imidazol-2-ylthio)pentyl]-N-heptyl-2-benzoxazolamine (WO93/23392)

EXAMPLES

The inventive compounds are specifically described below. The invention is not limited to these specific examples.

Example 1

Production of 6-(oxazolo[4,5-b]pyridin-2-ylthio)-N-(2,6-diisopropylphenyl)hexanamide Potassium carbonate (64 mg, 0.47 mmol) and 18-crown-6 (11 mg, 0.04 mmol) were added to a solution of 2-mercaptooxazolo[4,5-b]pyridine (64 mg, 0.42 mmol) and 6-bromo-N-(2,6-diisopropylphenyl)hexanamide (150 mg, 0.42 mmol) in DMF (3 ml), and the resulting mixture was stirred at 80° C. for 4 hours. After the reaction solution was diluted with water, the organic layer was extracted with ethyl acetate. The organic layer was washed with water and dried over anhydrous magnesium sulfate, from which the solvents were distilled off. The residue was purified by silica gel column chromatography (elution solvents:hexane:ethyl acetate=2:1); the resulting crystal was recrystallized from ethyl acetate-hexane, to recover the objective compound of 49 mg (at a yield of 27%) as a colorless needle-like crystal.
Melting Point: 94–95° C. IR (KBr) cm$^{-1}$: 3230, 2965, 1646, 1497, 1403. 1H-NMR (d$_6$-DMSO) δ: 1.14 (12H, d, J=6.8 Hz), 1.52–1.68 (2H, m), 1.68–1.82 (2H, m), 1.82–1.97 (2H, m), 2.33–2.45 (2H, m), 3.11 (2H, sept, J=6.8 Hz), 3.43 (2H, t, J=7.0 Hz), 7.12 (1H, d, J=8.1 Hz), 7.12 (1H, d, J=6.6 Hz), 7.22 (1H, dd, J=8.1, 6.6 Hz), 7.31 (1H, dd, J=8.1, 4.8 Hz) 7.98 (1H, dd, J=8.1, 1.5 Hz), 8.42 (1H, d, J=4.8 Hz), 8.72 (1H, br s). EIMS m/z (relative intensity): 425 (M$^+$), 407 (100). Elementary Analysis: $C_{24}H_{31}N_3O_2S$ Required: C, 67.73; H, 7.34; N, 9.87; S, 7.53. Found: C, 67.68; H, 7.33; N, 9.86; S, 7.57.

Example 2

Production of 6-(oxazolo[4,5-c]pyridin-2-ylthio)-N-(2,6-diisopropylphenyl)hexanamide In the same manner as in Example 1 except for the use of 2-mercaptooxazolo[4,5-c]pyridine instead of 2-mercaptooxazolo[4,5-b]pyridine, reaction progressed to recover the objective compound as a colorless needle-like crystal.

Melting Point: 126–127° C. IR (KBr) cm$^{-1}$: 3239, 2963, 1645, 1494, 1460. 1H-NMR (d$_6$-DMSO) δ: 1.14 (12H, d, J=6.9 Hz), 1.52–1.65 (2H, m), 1.67–1.80 (2H, m), 1.83–1.96 (2H, m), 2.33–2.43 (2H, m), 3.11 (2H, sept, J=6.9 Hz), 3.42 (2H, t, J=7.1 Hz), 7.12 (1H, d, J=8.3 Hz), 7.12 (1H, d, J=6.9 Hz), 7.22 (1H, dd, J=8.3, 6.9 Hz), 7.66 (1H, dd, J=5.5, 1.0 Hz) 8.49 (1H, d, J=5.5 Hz), 8.72 (1H, br s), 8.89 (1H, s). EIMS m/z (relative intensity): 425 (M$^+$,100). Elementary Analysis: $C_{24}H_{31}N_3O_2S$ Required: C, 67.73; H, 7.34; N, 9.87; S, 7.53. Found: C, 67.65; H, 7.40; N, 9.59; S, 7.44.

Example 3

Production of 6-(oxazolo[5,4-c]pyridin-2-ylthio)-N-(2,6-diisopropylphenyl)hexanamide In the same manner as in Example 1 except for the use of 2-mercaptooxazolo[5,4-c]pyridine instead of 2-mercaptooxazolo[4,5-b]pyridine, reaction progressed to recover the objective compound as a colorless needle-like crystal.

Melting Point: 164–165° C. IR (KBr) cm$^{-1}$: 3227, 2963, 1652, 1482, 1115. 1H-NMR (d$_6$-DMSO) δ: 1.14 (12H, d, J=6.8 Hz), 1.53–1.67 (2H, m), 1.67–1.82 (2H, m), 1.84–1.96 (2H, m), 2.33–2.42 (2H, m), 3.11 (2H, sept, J=6.8 Hz), 3.44 (2H, t, J=7.2 Hz), 7.12 (1H, d, J=8.4 Hz), 7.12 (1H, d, J=6.7 Hz), 7.22 (1H, dd, J=8.4, 6.7 Hz), 7.63 (1H, dd, J=5.4, 1.0 Hz) 8.49 (1H, d, J=5.4 Hz), 8.71 (1H, br s), 8.89 (1H, d, J=0.7 Hz). EIMS m/z (relative intensity): 425 (M$^+$), 230 (100). Elementary Analysis: $C_{24}H_{31}N_3O_2S$ Required: C, 67.73; H, 7.34; N, 9.87, S, 7.53. Found: C, 67.84; H, 7.43; N, 9.74, S, 7.51.

Example 4

Production of 6-(oxazolo[5,4-b]pyridin-2-ylthio)-N-(2,6-diisopropylphenyl)hexanamide In the same manner as in Example 1 except for the use of 2-mercaptooxazolo[5,4-b]pyridine instead of 2-mercaptooxazolo[4,5-b]pyridine, reaction progressed to recover the objective compound as a colorless needle-like crystal.

Melting Point: 146–147° C. IR (KBr) cm$^{-1}$: 3252, 2967, 1648, 1492, 1207. 1H-NMR (d$_6$-DMSO) δ: 1.14 (12H, d, J=6.8 Hz), 1.53–1.67 (2H, m), 1.67–1.81 (2H, m), 1.83–1.96 (2H, m), 2.43–2.55 (2H, m), 3.11 (2H, sept, J=6.8 Hz), 3.40 (2H, t, J=7.2 Hz), 7.12 (1H, d, J=8.6 Hz), 7.12 (1H, d, J=6.7 Hz), 7.22 (1H, dd, J=8.6, 6.7 Hz), 7.40 (1H, dd, J=7.8, 5.1 Hz) 8.01 (1H, dd, J=7.8, 1.6 Hz), 8.22 (1H, dd, J=5.1, 1.6 Hz), 8.71 (1H, br s). EIMS m/z (relative intensity): 425 (M$^+$), 176 (100). Elementary Analysis: $C_{24}H_{31}N_3O_2S$ Required: C, 67.73; H, 7.34; N, 9.87; S, 7.53. Found: C, 67.84; H, 7.44; N, 9.63; S, 7.50.

Example 5

Production of 6-(imidazolo[4,5-b]pyridin-2-ylthio)-N-(2,6-diisopropylphenyl)hexanamide Potassium carbonate (86 mg, 0.62 mmol) and 18-crown-6 (15 mg, 0.06 mmol) were added to a solution of 2-mercaptoimidazolo[4,5-b]pyridine (85 mg, 0.56 mmol) and 6-bromo-N-(2,6-diisopropylphenyl)hexanamide (200 mg, 0.56 mmol) in DMF (4 ml), and the resulting mixture was stirred at 80° C. for 4 hours. After the reaction solution was diluted with water, the organic layer was extracted with ethyl acetate. The organic layer was washed with water and dried over anhydrous magnesium sulfate, from which the solvents were distilled off. The residue was purified by silica gel column chromatography (elution solvents:chloroform:methanol=100:1); the resulting crystal was recrystallized from chloroform-ethyl acetate-hexane, to recover the objective compound of 73 mg (at a yield of 31%) as a colorless needle-like crystal.

Melting Point: 227–229° C. IR (KBr) cm$^{-1}$: 3235, 2963, 1651, 1395, 1268. 1H-NMR (d$_6$-DMSO) δ: 1.14 (12H, d, J=6.8 Hz), 1.51–1.89 (6H, m), 2.38 (2H, m), 3.11 (2H, sept, J=6.8 Hz), 3.36 (2H, t, J=7.1 Hz), 7.11 (1H, dd, J=8.3, 4.9 Hz), 7.11 (1H, d, J=8.3 Hz), 7.12 (1H, d, J=6.6 Hz), 7.22 (1H, dd, J=8.3, 6.6 Hz), 7.77 (1H, d, J=8.3 Hz) 8.19 (1H, d, J=4.9 Hz), 8.72 (1H, br s). EIMS m/z (relative intensity): 424 (M$^+$), 165 (100). Elementary Analysis: $C_{24}H_2N_4OS$ Required: C, 67.89; H, 7.60; N, 13.20; S, 7.55. Found: C, 68.01; H, 7.62; N, 12.96; S, 7.41.

Example 6

Production of 6-(imidazolo[4,5-c]pyridin-2-ylthio)-N-(2,6-diisopropylphenyl)hexanamide In the same manner as in Example 5 except for the use of 2-mercaptoimidazolo[4,5-c]pyridine instead of 2-mercaptoimidazolo[4,5-b]pyridine, reaction progressed to recover the objective compound as a colorless needle-like crystal.

Melting Point: 96–98° C. IR (KBr) cm$^{-1}$: 3231, 2962, 1649, 1463, 1278. 1H-NMR (d$_6$-DMSO) δ: 1.14 (12H, d, J=6.8 Hz), 1.51–1.89 (6H, m), 2.38 (2H, m), 3.11 (2H, sept, J=6.8 Hz), 3.36 (2H, t, J=5.6 Hz), 7.12 (1H, d, J=8.3 Hz), 7.12 (1H, d, J=6.6 Hz), 7.22 (1H, dd, J=8.3, 6.6 Hz), 7.40 (1H, dd, J=5.6, 1.0 Hz) 8.19 (1H, d , J=5.6 Hz), 8.70 (1H, d, J=1.0 Hz), 8.71 (1H, br s). EIMS m/z (relative intensity): 424 (M$^+$), 165 (100). Elementary Analysis: $C_{24}H_{32}N_4OS$ Required: C, 67.89; H, 7.60; N, 13.20; S, 7.55. Found: C, 67.95; H, 7.66; N, 12.92; S, 7.33.

Example 7

Production of 9-(oxazolo[4,5-b]pyridin-2-ylthio)-N-(2,6-diisopropylphenyl)nonanamide In the same manner as in Example 1 except for the use of 9-bromo-N-(2,6-diisopropylphenyl)nonanamide instead of 6-bromo-N-(2,6-diisopropylphenyl)hexanamide, reaction progressed to recover the objective compound as a colorless amorphous.

IR (KBr)cm$^{-1}$: 3435, 3234, 2926, 1647, 1494, 1402. 1H-NMR (d$_6$-DMSO) δ: 1.13 (12H, d, J=6.8 Hz), 1.39–1.72 (10H, m), 1.85 (2H, quint, J=7.2 Hz), 2.34 (2H, m), 3.10 (2H, sept, J=6.8 Hz), 3.39 (2H, t, J=7.2 Hz), 7.10 (1H, d, J=8.6 Hz), 7.11 (1H, d, J=6.8 Hz), 7.21 (1H, dd, J=8.6, 6.8 Hz), 7.30 (1H, dd, J=8.1, 5.0 Hz), 7.97 (1H, dd, J=8.1, 1.5 Hz), 8.41 (1H, dd, 5.0, 1.5 Hz),8.68 (1H, br s). EIMS m/z (relative intensity): 467 (M$^+$, 100). Elementary Analysis: C$_{27}$H$_{37}$N$_3$O$_2$S Required: C, 69.34; H, 7.97; N, 8.99; S, 6.86. Found: C, 69.39; H, 8.05; N, 8.85; S, 6.56.

Example 8

Production of 9-(oxazolo[4,5-c]pyridin-2-ylthio)-N-(2,6-diisopropylphenyl)nonanamide In the same manner as in Example 6 except for the use of 9-bromo-N-(2,6-diisopropylphenyl)nonanamide instead of 6-bromo-N-(2,6-diisopropylphenyl)hexanamide, reaction progressed to recover the objective compound as a colorless needle-like crystal.

Melting Point: 74–75° C. IR (KBr) cm$^{-1}$: 3434, 3237, 2928, 1647, 1107. 1H-NMR (d$_6$-DMSO) δ: 1.13 (12H, d, J=6.8 Hz), 1.38–1.71 (10H, m), 1.84 (2H, quint, J=7.3 Hz), 2.34 (2H, m), 3.10 (2H, sept, J=6.8 Hz), 3.38 (2H, t, J=7.3 Hz), 7.11 (1H, d, J=8.3 Hz), 7.11 (1H, d, J=6.8 Hz), 7.21 (1H, dd, J=8.3, 6.8 Hz), 7.64 (1H, dd, J=5.4, 0.7 Hz), 8.47 (1H, d, J=5.4 Hz), 8.68 (1H, br s), 8.88 (1H, d, 0.7 Hz). EIMS m/z (relative intensity): 467 (M$^+$), 217(100). Elementary Analysis: C$_{27}$H$_{37}$N$_3$O$_2$S Required: C, 69.34; H, 7.97; N, 8.99; S, 6.86. Found: C, 69.28; H, 8.00; N, 8.85; S, 6.80.

Example 9

Production of 9-(oxazolo[5,4-c]pyridin-2-ylthio)-N-(2,6-diisopropylphenyl)nonanamide In the same manner as in Example 3 except for the use of 9-bromo-N-(2,6-diisopropylphenyl)nonanamide instead of 6-bromo-N-(2,6-diisopropylphenyl)hexanamide, reaction progressed to recover the objective compound as a colorless needle-like crystal.

Melting Point: 81–82° C. IR (KBr)cm$^{-1}$: 3435, 3259, 2927, 1647, 1480. 1H-NMR (d$_6$-DMSO) δ: 1.13 (12H, d, J=7.1 Hz), 1.39–1.69 (10H, m), 1.85 (2H, quint, J=7.2 Hz), 2.34 (2H,m), 3.10 (2H, sept, J=7.1 Hz), 3.40 (2H, t, J=7.2 Hz), 7.11 (1H, d, J=8.5 Hz), 7.11 (1H, d, J=6.8 Hz), 7.21 (1H, dd, J=8.5, 6.8 Hz), 7.62 (1H, dd, J=5.1, 1.0 Hz), 8.47 (1H, d, J=5.1 Hz), 8.83 (1H, br s), 8.88 (1H, d, 1.0 Hz). EIMS m/z (relative intensity): 467 (M$^+$), 217(100). Elementary Analysis: C$_{27}$H$_{37}$N$_3$O$_2$S Required: C, 69.34; H, 7.97; N, 8.99; S, 6.86. Found: C, 69.37; H, 8.03; N, 8.85; S, 6.82.

Example 10

Production of 9-(oxazolo[5,4-b]pyridin-2-ylthio)-N-(2,6-diisopropylphenyl)nonanamide In the same manner as in Example 4 except for the use of 9-bromo-N-(2,6-diisopropylphenyl)nonanamide instead of 6-bromo-N-(2,6-diisopropylphenyl)hexanamide, reaction progressed to recover the objective compound as a colorless oil.

IR (cap) cm$^{-1}$: 3253, 2962, 2929, 1651, 1489, 1210. 1H-NMR (d$_6$-DMSO) δ: 1.13 (12H, d, J=6.8 Hz), 1.38–1.69 (10H, m), 1.84 (2H, quint, J=7.1 Hz), 2.34 (2H,m), 3.10 (2H, sept, J=6.8 Hz), 3.37 (2H, t, J=7.1 Hz), 7.10 (1H, d, J=8.6 Hz), 7.11 (1H, d, J=6.6 Hz), 7.21 (1H, dd, J=8.6, 6.6 Hz), 7.38 (1H, dd, J=7.8, 4.9 Hz), 8.00 (1H, dd, J=7.8, 1.5 Hz), 8.21 (1H, dd, 4.9, 1.5 Hz), 8.68 (1H, br s). EIMS m/z (relative intensity): 467 (M$^+$, 100). Elementary Analysis: C$_{27}$H$_{37}$N$_3$O$_2$S Required: C, 69.34; H, 7.97; N, 8.99; S, 6.86. Found: C, 69.60; H, 8.20; N, 8.58; S, 6.86.

Example 11

Production of 6-(5-methyloxazolo[4,5-b]pyridin-2-ylthio)-N-(2,6-diisopropylphenyl)hexanamide 10% palladium-carbon (200 mg) was added to an ethanol suspension (50 ml) of 3-hydroxy-6-methyl-2-nitropyridine (2.0 g, 13.0 mmol), with stirring in hydrogen gas atmosphere for 90 minutes. After reaction, the catalyst palladium-carbon was filtered off.

To the resulting ethanol solution of 2-amino-3-hydroxy-6-methylpyridine was added potassium o-ethyl dithiocarbonate (4.16 g, 26.0 mmol), for heating under reflux for 17 hours to distill off the solvent. The residue was dissolved in water. Through addition of acetic acid, the resulting solution was adjusted to pH 5. The deposited crystal was filtered and washed with water, and then, the resulting crystal was dried under heating at 80° C.

Potassium carbonate (86 mg, 0.62 mmol) and 18-crown-6 (15 mg, 0.06 mmol) were added to a solution of the resulting 2-mercapto-5-methyl-oxazolo[4,5-b]pyridine (94 mg, 0.56 mmol) and 6-bromo-N-(2,6-diisopropylphenyl)hexanamide (200 mg, 0.5 mmol) in DMF (4 ml), and the resulting mixture was stirred at 80° C. for 4 hours. After the reaction solution was diluted with water, the organic layer was extracted with ethyl acetate. The organic layer was washed with water and dried over anhydrous magnesium sulfate, from which the solvents were distilled off. The residue was purified by silica gel column chromatography (elution solvents:chloroform:methanol=20:1); the resulting crystal was recrystallized from methanol-ethyl acetate-hexane, to recover the objective compound of 150 mg (at a yield of 61%) as a colorless needle-like crystal.

Melting Point: 145–146° C. IR (KBr) cm$^{-1}$: 3229, 2963, 1645, 1504, 1400. 1H-NMR (d$_6$-DMSO) δ: 1.14 (12H, d, J=6.8 Hz), 1.55–1.93 (6H, m),(2H, m), 2.56 (3H, s), 1.15 3.11 (2H, sept, J=6.8 Hz), 3.40 (2H, t, J=7.1 Hz), 1.16 7.12 (1H, d, J=8.5 Hz), 7.12 (1H, d, J=6.6 Hz), 7.16 (1H, d, J=8.3 Hz), 7.22 (1H, dd, J=8.5, 6.6 Hz), 7.84 (1H, d, J=8.3 Hz), 8.72 (1H, br s). EIMS m/z (relative intensity): 439 (M$^+$), 230 (100). Elementary Analysis: C$_{25}$H$_{33}$N$_3$O$_2$S Required: C, 68.30; H, 7.57; N, 9.56; S, 7.29. Found: C, 68.14; H, 7.60; N, 9.45; S, 7.31.

Example 12

Production of 6-(4-methyloxazolo[5,4-b]pyridin-2-ylthio)-N-(2,6-diisopropylphenyl)hexanamide In the same manner as in Example 11 except for the use of 2-hydroxy-4-methyl-3-nitropyridine instead of 3-hydroxy-6-methyl-2-nitropyridine, reaction progressed to recover the objective compound as a colorless crystal.

Melting Point: 157–158° C. IR (KBr) cm$^{-1}$: 3430, 3261, 1648, 1533. 1H-NMR (d$_6$-DMSO) δ: 1.13 (12H, d, J=7.1 Hz), 1.53–1.94 (6H, m), 2.38 (2H, m), 2.53 (3H, s), 3.09 (2H, sept, J=7.1 Hz), 3.37 (2H, t, J=7.2 Hz), 7.08 (1H, d, J=8.8 Hz), 7.09 (1H, d, J=6.6 Hz), 7.17 (1H, dd, J=4.9, 0.7 Hz), 7.19 (1H, dd, J=8.8, 6.6 Hz), 8.04 (1H, d, J=4.9 Hz), 8.64 (1H, br s). EIMS m/z (relative intensity): 439 (M$^+$, 100). Elementary Analysis: C$_{25}$H$_{33}$N$_3$O$_2$ S Required: C, 68.30; H, 7.57; N, 9.56; S, 7.29. Found: C, 68.14; H, 7.53; N, 9.43; S, 7.26.

Example 13

Production of 6-(7-methyloxazolo[4,5-b]pyridin-2-ylthio)-N-(2,6-diisopropylphenyl)hexanamide In the same manner as in Example 11 except for the use of 2-amino-3-hydroxy-4-methylpyridine instead of 2-amino-3-hydroxy-6-methylpyridine, reaction progressed to recover the objective compound as a colorless crystal.

Melting Point: 145–147° C. IR (KBr) cm$^{-1}$: 3234, 2962, 1647, 1500, 1124. 1H-NMR (d$_6$-DMSO) δ: 1.13 (12H, d, J=6.8 Hz), 1.55–1.63 (2H, m), 1.70–1.79 (2H, m), 1.87–1.95 (2H, m), 2.35–2.42 (2H, m), 2.50 (3H, s), 3.10 (2H, sept, J=6.8 Hz), 3.41 (2H, t, J=7.2 Hz), 7.11 (1H, d, J=7.8 Hz), 7.11 (1H, d, J=7.6 Hz), 7.14 (1H, dd, J=5.1, 0.7 Hz), 7.22 (1H, dd, J=7.8, 7.6 Hz), 8.27 (1H, d, J=5.1 Hz), 8.73 (1H, br s). EIMS m/z (relative intensity): 439 (M$^+$), 230 (100). Elementary Analysis: $C_{25}H_{33}N_3O_2S$ Required: C, 68.30; H, 7.57; N, 9.56; S, 7.29. Found: C, 68.13; H, 7.62; N, 9.28; S, 7.14.

Example 14

Production of 6-(5,7-dimethyloxazolo[4,5-b]pyridin-2-ylthio)-N-(2,6-diisopropylphenyl)hexanamide In the same manner as in Example 11 except for the use of 2-amino-4,6-dimethyl-3-hydroxypyridine instead of 2-amino-3-hydroxy-6-methylpyridine, reaction progressed to recover the objective compound as a colorless crystal.

Melting Point: 169–171° C. IR (KBr) cm$^-$: 3206, 2966, 1641, 1503, 1114. 1H-NMR ($d_6$-DMSO) δ: 1.13 (12H, d, J=6.8 Hz), 1.52–1.62 (2H, m), 1.68–1.78 (2H, m), 1.84–1.94 (2H, m), 2.36–2.47 (2H, m), 2.48 (3H, s), 2.50 (3H, s), 3.09 (2H, sept, J=6.8 Hz), 3.38 (2H, t, J=7.1 Hz), 6.99 (1H, s), 7.11 (1H, d, J=7.8 Hz), 7.11 (1H, d, J=7.6 Hz), 7.21 (1H, dd, J=7.8, 7.6 Hz), 8.72 (1H, br s). EIMS m/z (relative intensity): 453 (M$^+$), 181 (100). Elementary Analysis: $C_{26}H_{35}N_3O_2S$ Required: C, 68.84; H, 7.78; N, 9.26; S, 7.07. Found: C, 68.95; H, 7.77; N, 9.17; S, 7.10.

Example 15

Production of 6-(N-dimethylphenylsilylmethyl-N-oxazolo[4,5-b]pyridin-2-ylamino)-N-(2,6-diisopropylphenyl)hexanamide Potassium carbonate (42 mg, 0.3 mmol) and 18-crown-6 (5 mg, 0.02 mmol) were added to a solution of 6-(oxazolo[4,5-b]pyridin-2-ylamino)-N-(2,6-diisopropylphenyl)hexanamide (78 mg, 0.19 mmol) and chloromethyldimethylphenylsilane (42 mg, 0.23 mmol) in DMF (2 ml), and the resulting mixture was stirred at 80° C. for 2 hours. After the reaction solution was diluted with water, the organic layer was extracted with ether. The organic layer was washed with water and dried over anhydrous magnesium sulfate, from which the solvents were distilled off. The residue was purified by preparative thin layer chromatography (elution solvents:hexane:acetone=5:3), to recover the objective compound of 47 mg (at a yield of 44%) as a colorless oil.

IR (cap) cm$^{-1}$: 3252, 2962, 1645, 1563, 1413. 1H-NMR ($d_6$-DMSO) δ: 0.38 (6H, s), 1.11 (12H, d, J=6.8 Hz), 1.30–1.40 (2H, m), 1.58–1.72 (4H, m), 2.31 (2H, t, J=7.3 Hz), 3.07 (2H, sept, J=6.8 Hz), 3.36 (2H, s), 3.43 (2H, t, J=6.8 Hz), 6.86 (1H, dd, J=7.8, 5.1 Hz), 7.09 (1H, d, J=8.3 Hz), 7.09 (1H, d, J=7.1 Hz), 7.19 (1H, dd, J=8.3, 7.1 Hz), 7.30–7.35 (3H, m), 7.46 (1H, dd, J=7.8, 1.5 Hz), 7.54–7.58 (2H, m), 8.05 (1H, dd, J=5.1, 1.5 Hz), 8.64 (1H, br s). EIMS m/z (relative intensity): 541 (M$^+$-Me), 135 (100). Elementary Analysis: $C_{33}H_{44}N_4O_2Si$ Required: C, 71.18; H, 7.96; N, 10.06. Found: C, 70.94; H, 8.02; N, 10.12.

Example 16

Production of 6-(N-methyl-N-oxazolo[4,5-b]pyridin-2-yl-amino)-N-(2,6-diisopropylphenyl)hexanamide Potassium carbonate (152 mg, 1.1 mmol) and 18-crown-6 (26.4 mg, 0.1 mmol) were added to a solution of the resulting 6-bromo-N-(2,6-diisopropylphenyl)hexanamide (354 mmol, 1.0 mmol) and N-benzylmethylamine (121 mg, 1.0 mmol) in DMF (5 ml), and the resulting mixture was stirred at 80° C. for 2 hours. After the reaction solution was diluted with water, the organic layer was extracted with ether. The organic layer was washed with water and dried over anhydrous magnesium sulfate, from which the solvents were distilled off. The residue was purified by silica gel column chromatography (20 g of silica gel; elution solvents:chloroform:methanol=30:1); the resulting crystal was recrystallized from acetone-ether-methanol, to recover the objective compound of 235 mg (at a yield of 60%) as a colorless needle-like crystal. To a solution in ethanol (5 ml) of the benzylmethylaminoanilide (220 mg, 0.56 mmol) were added a catalytic amount of conc. hydrochloric acid (0.05 ml) and 10% palladium-carbon catalyst (100 mg), and the resulting mixture was stirred at ambient temperature in hydrogen atmosphere for 15 hours. The reaction solution was filtered through celite. The resulting filtrate was concentrated under reduced pressure, which was then diluted with ethyl acetate. The organic layer was sequentially washed with an aqueous saturated sodium hydrogen carbonate solution and saturated sodium chloride solution, and was then dried over anhydrous magnesium sulfate, from which the solvents were distilled off to recover 6-methylamino-N-(2,6-diisopropylphenyl)hexanamide (145 mg at a yield of 85%) as a solid material. The methylaminoanilide (120 mg, 0.39 mmol) and 2-methyloxazolo[4,5-b]pyridine (50 mg, 0.3 mmol) were mixed together and stirred at 100° C. for 3 hours. The reaction residue was purified by silica gel column chromatography (12 g of silica gel; elution solvents:hexane:acetone=5:3). The resulting crystal was recrystallized from acetone-ether-hexane, to recover the objective compound (97 mg at a yield of 76%) as a colorless crystal.

Melting Point: 162–164° C. IR (KBr) cm$^{-1}$: 3435, 3230, 1656, 1562, 1412. 1H-NMR ($d_6$-DMSO) δ: 1.11 (12H, d, J=6.8 Hz), 1.40–1.50 (2H, m), 1.67–1.79 (4H, m), 2.35 (2H, t, J=6.8 Hz), 3.08 (2H, sept, J=6.8 Hz), 3.18 (3H, s), 3.57 (2H, t, J=7.1 Hz), 6.90 (1H, dd, J=7.8, 5.1 Hz), 7.09 (1H, d, J=8.1 Hz), 7.09 (1H, d, J=6.8 Hz), 7.19 (1H, dd, J=8.1, 6.8 Hz), 7.57 (1H, dd, J=7.8, 1.5 Hz), 8.09 (1H, dd, J=5.1, 1.5 Hz), 8.65 (1H, br s). EIMS m/z (relative intensity): 422 (M$^+$), 176 (100). Elementary Analysis: $C_{25}H_{34}N_4O_2$ Required: C, 71.06; H, 8.11; N, 13.26. Found: C, 71.04; H, 8.27; N, 13.05.

Example 17

Production of 6-(oxazolo[4,5-b]pyridin-2-ylamino)-N-(2,6-diisopropylphenyl)hexanamide 2-Methylthiooxazolo[4,5-b]pyridine (65.0 mg, 0.39 mmol) and 6-amino-N-(2,6-diisopropylphenyl)hexanamide (114 mg, 0.39 mmol) were mixed together and stirred at 90° C. for 2 hours. The reaction mixture was purified by preparative thin layer chromatography (elution solvents:hexane:acetone=5:3). The resulting crude crystal was recrystallized from dichloromethane-ether-hexane, to recover the objective compound as a colorless needle-like crystal.

Melting Point: 152–153° C. IR (KBr) cm$^{-1}$: 3416, 2964, 1656, 1571, 1413. 1H-NMR ($d_6$-DMSO) δ: 1.11 (12H, d, J=6.8 Hz), 1.43–1.57 (2H, m), 1.64–1.77 (4H, m), 2.35 (2H, t, J=7.3 Hz), 3.08 (2H, sept, J=6.8 Hz), 3.38 (2H, dd, J=12.9, 6.8 Hz), 6.89 (1H, dd, J=7.8, 5.1 Hz), 7.09 (1H, d, J=8.3 Hz), 7.09 (1H, d, J=7.1 Hz), 7.19 (1H, dd, J=8.3, 7.1 Hz), 7.53 (1H, dd, J=7.8, 1.5 Hz), 7.87 (1H, br s), 8.06 (1H, dd, J=5.1, 1.5 Hz), 8.65 (1H, br s). EIMS m/z (relative intensity): 408 (M$^+$, 100). Elementary Analysis: $C_{24}H_{32}N_4O_2$ Required: C, 70.56; H, 7.89; N, 13.71. Found: C, 70.70; H, 7.87; N, 13.51.

Example 18

Production of 6-(oxazolo[4,5-c]pyridin-2-ylamino)-N-(2,6-diisopropylphenyl)hexanamide In the same manner as in Example 17 except for the use of 2-methylthiooxazolo[4,5-c]pyridine instead of 2-methylthiooxazolo[4,5-b]pyridine, reaction progressed to recover the objective compound as a colorless needle-like crystal.

Melting Point: 170–171° C. IR (KBr) cm$^{-1}$: 3258, 2966, 1648, 1578, 1465. 1H-NMR (d$_6$-DMSO) δ: 1.11 (12H, d, J=7.1 Hz), 1.44–1.54 (2H, m), 1.63–1.75 (4H, m), 2.35 (2H, t, J=6.8 Hz), 3.08 (2H, sept, J=7.1 Hz), 3.37 (2H, dd, J=12.9, 6.8 Hz), 7.09 (1H, d, J=8.3 Hz), 7.09 (1H, d, J=7.1 Hz), 7.19 (1H, dd, J=8.3, 7.1 Hz), 7.31 (1H, dd, J=5.1, 0.7 Hz), 7.73 (1H, br s), 8.17 (1H, d, J=5.1 Hz), 8.46 (1H, d, J=0.7 Hz), 8.67 (1H, br s). EIMS m/z (relative intensity): 408 (M$^+$), 162 (100). Elementary Analysis: $C_{24}H_{32}N_4O_2$ Required: C, 70.56; H, 7.89; N, 13.71. Found: C, 70.63; H, 7.96; N, 13.54.

Example 19

Production of 6-(oxazolo[5,4-c]pyridin-2-ylamino)-N-(2,6-diisopropylphenyl)hexanamide In the same manner as in Example 17 except for the use of 2-methylthiooxazolo[5,4-c]pyridine instead of 2-methylthiooxazolo[4,5-b]pyridine, reaction progressed to recover the objective compound as a colorless needle-like crystal.

Melting Point: 189–190° C. IR (KBr) cm$^{-1}$: 3231, 2963, 1664, 1577, 1468. 1H-NMR (d$_6$-DMSO) δ: 1.11 (12H, d, J=6.8 Hz), 1.43–1.52 (2H, m), 1.64–1.75 (4H, m), 2.35 (2H, t, J=6.3 Hz), 3.08 (2H, sept, J=6.8 Hz), 3.38 (2H, dd, J=12.9, 6.8 Hz), 7.09 (1H, d, J=8.3 Hz), 7.09 (1H, d, J=7.1 Hz), 7.18 (1H, dd, J=5.4, 0.7 Hz), 7.19 (1H, dd, J=8.3, 7.1 Hz), 7.98 (1H, br s), 8.21 (1H, d, J=5.4 Hz), 8.45 (1H, d, J=0.7 Hz), 8.67 (1H, br s). EIMS m/z (relative intensity): 408 (M$^+$), 162 (100). Elementary Analysis: $C_{24}H_{32}N_4O_2$ Required: C, 70.56; H, 7.89; N, 13.71. Found: C, 70.40; H, 7.96; N, 13.55.

Example 20

Production of 6-(oxazolo[5,4-b]pyridin-2-ylamino)-N-(2,6-diisopropylphenyl)hexanamide In the same manner as in Example 17 except for the use of 2-methylthiooxazolo[5,4-b]pyridine instead of 2-methylthiooxazolo[4,5-b]pyridine, reaction progressed to recover the objective compound as a colorless needle-like crystal.

Melting Point: 177–178° C. IR (KBr) cm$^{-1}$: 3232, 2962, 1660, 1585, 1404. 1H-NMR (d$_6$-DMSO) δ: 1.11 (12H, d, J=6.8 Hz), 1.45–1.54 (2H, m), 1.64–1.76 (4H, m), 2.35 (2H, t, J=6.8 Hz), 3.08 (2H, sept, J=6.8 Hz), 3.37 (2H, dd, J=12.9, 6.8 Hz), 7.09 (1H, d, J=8.3 Hz), 7.09 (1H, d, J=6.8 Hz), 7.09 (1H, dd, J=7.6, 5.1 Hz), 7.19 (1H, dd, J=8.3, 6.8 Hz), 7.48 (1H, dd, J=7.6, 0.5 Hz), 7.73 (1H, br s), 7.79 (1H, dd, J=5.1, 0.5 Hz), 8.64 (1H, br s). Elementary Analysis: $C_{24}H_{32}N_4O_2$ Required: C, 70.56; H, 7.89; N, 13.71. Found: C, 70.68; H, 7.97; N, 13.44.

Example 21

Production of 6-(thiazolo[5,4-b]pyridin-2-ylthio)-N-(2,6-diisopropylphenyl)hexanamide Potassium carbonate (46 mg, 0.33 mmol) and 18-crown-6 (8 mg, 0.03 mmol) were added to a solution in DMF (2 ml) of 2-mercaptothiazolo[5,4-b]pyridine (51 mmol, 0.3 mmol) and 6-bromo-N-(2,6-diisopropylphenyl)hexanamide (106 mg, 0.3 mmol), and the resulting mixture was stirred at 80° C. for one hour. After the reaction solution was diluted with water, the organic layer was extracted with ethyl acetate. The organic layer was washed with water and dried over anhydrous magnesium sulfate, from which the solvents were distilled off. The residue was purified by silica gel column chromatography (elution solvents:chloroform:methanol= 50:1); the resulting crystal was recrystallized from acetone-ether-hexane, to recover the objective compound of 108 mg (at a yield of 82%) as a colorless needle-like crystal.

Melting Point: 137–138° C. IR (KBr) cm$^{-1}$: 3436, 3233, 1647, 1435, 1377. 1H-NMR (d$_6$-DMSO) d :δ 1.12 (12H, d, J=6.8 Hz), 1.52–1.60 (2H, m), 1.70–1.78 (2H, m), 1.82–1.90 (2H, m), 2.37 (2H, t, J=6.8 Hz), 3.08 (2H, sept, J=6.8 Hz), 3.41 (2H, t, J=7.3 Hz), 7.10 (1H, d, J=7.6 Hz), 7.2 (1H, t, J=7.6 Hz), 7.47 (1H, dd, J=8.3, 4.6 Hz), 8.14 (1H, dd, J=8.3, 1.5 Hz) 8.45 (1H, dd, J=4.6, 1.5 Hz), 8.71 (1H, br s). Elementary Analysis: $C_{24}H_{31}N_3OS_2$ Required: C, 65.27; H, 7.07; N, 9.51; S, 14.52. Found: C, 65.46; H, 7.13; N, 9.33; S, 14.24.

Example 22

Production of 6-(4-hydroxybenzoxazol-2-ylthio)-N-(2,6-diisopropylphenyl)hexanamide 2-Nitro-3-benzyloxyphenol (334 mg, 1.36 mmol) was dissolved in acetic acid (3 ml) under heating, followed by addition of zinc (1.78 g, 27.2 mmol), and the resulting mixture was stirred at ambient temperature for one hour. After the reaction solution was diluted with water, the organic layer was extracted with ethyl acetate. The organic layer was washed sequentially with sodium hydrogen carbonate, water and saturated sodium chloride solution, and was dried over anhydrous magnesium sulfate, from which the solvents were distilled off. The residue was purified by silica gel column chromatography (50 g of silica gel; elution solvents:hexane:acetone=20:3 to 5:1) and solidified from acetone-hexane, to recover 2-amino-3-benzyloxyphenol (155 mg at a yield of 53%) as a brown powder.

To a solution in ethanol (10 ml) of the aminophenol (135 mg, 0.627 mmol) was added potassium o-ethyl dithiocarbonate (151 mg, 0.941 mmol), and the resulting mixture was refluxed under heating for 24 hours. After the solution was left to stand for cooling, the solvents were distilled off under reduced pressure; to the resulting residue was added 1 N hydrochloric acid to adjust the solution to acidity, to extract the organic layer. The organic layer was washed with saturated sodium chloride solution and dried over anhydrous sodium sulfate, from which the solvents were distilled off to recover a solid material. The solid material was prepared as a powder by using acetone and hexane, to recover 2-mercapto-4-benzyloxybenzoxazole (143 mg at a yield of 89%).

To a solution in DMF (3 ml) of the oxazole (135 mg, 0.525 mmol) and 6-bromo-N-(2,6-diisopropylphenyl) hexanamide (186 mg, 0.525 mmol) were added potassium carbonate (110 mg, 0.788 mmol) and 18-crown-6 (14 mg, 0.053 mmol), and the resulting mixture was stirred at 80° C. for 90 minutes. After the reaction solution was diluted with water, the organic layer was extracted with ether. The organic layer was washed sequentially with water and saturated sodium chloride solution, and was dried over anhydrous magnesium sulfate, from which the solvents were distilled off. The residue was purified by silica gel column chromatography (25 g of silica gel; elution solvents:hexane:acetone=20:3); the resulting crystal was recrystallized from acetone-hexane, to recover the objective compound of 206 mg (at a yield of 74%) as a colorless crystal.

The amide (188 mg, 0.354 mmol) was dissolved in trifluoroacetic acid (5 ml) while cooling in ice bath, followed by addition of thiophenol (440 mg, 3.54 mmol) with stirring for 2 minutes. After the temperature was then back to ambient temperature, the mixture was stirred for 12 hours. Furthermore, thiophenol (440 mg, 3.54 mmol) was added to the resulting solution, for 24-hr-stirring. Under reduced pressure, the solvents were distilled off. The resulting residue was diluted with water and extracted with ethyl acetate. The organic layer was washed sequentially with saturated sodium hydrogen carbonate solution, water and saturated sodium chloride solution, and was dried over anhydrous sodium sulfate, from which the solvents were distilled off. The residue was purified by silica gel column chromatography (75 g of silica gel; elution solvents:hexane:acetone= 5:1 to 10:3), and the resulting crystal was recrystallized from acetone-hexane, to recover the objective compound (108 mg at a yield of 69%) as a colorless crystal.

Melting Point: 160–161° C. IR (KBr) cm$^{-1}$: 3226, 2963, 1652, 1480, 1036, 1H-NMR (d$_6$-DMSO) δ: 1.12 (12H, d, J=6.8 Hz), 1.50–1.91 (6H, m), 2.36 (2H, m), 3.09 (2H, sept, J=6.8 Hz), 3.33 (2H, t, J=7.1 Hz), 6.72 (1H, dd, J=8.1, 1.2 Hz), 6.97 (1H, dd, J=8.1, 1.2 Hz), 7.06 (1H, t, J=8.1 Hz), 7.09 (1H, d, J=8.5 Hz), 7.09 (1H, d, J=6.6 Hz), 7.19 (1H, dd, J=8.5, 6.6 Hz) 8.66 (1H, br s), 9.57 (1H, br s). EIMS m/z (relative intensity): 440 (M$^+$, 100). Elementary Analysis: C$_{25}$H$_{32}$N$_2$O$_3$S Required: C, 68.15; H, 7.32; N, 6.36; S, 7.28. Found: C, 68.05; H, 7.33; N, 6.34; S, 7.18.

Example 23

Production of 6-(4-acetyloxybenzoxazol-2-ylthio)-N-(2,6-diisopropylphenyl)hexanamide Acetic anhydride (18 mg, 0.177 mmol) was added to a solution of 6-(4-hydroxybenzoxazol-2-ylthio)-N-(2,6-diisopropylphenyl)hexanamide (52 mg, 0.118 mmol) in pyridine (1 ml), with stirring at ambient temperature for 12 hours. The reaction solution was diluted with an aqueous 5% potassium hydrogen sulfate solution, was extracted the organic layer with ether. The organic layer was washed sequentially with an aqueous 5% potassium hydrogen sulfate solution, water and saturated sodium chloride solution, and was dried over anhydrous magnesium sulfate, from which the solvents were distilled off. The residue was purified by silica gel column chromatography (5 g of silica gel; elution solvents:hexane:acetone=5:1), and the resulting crystal was recrystallized from acetone-hexane, to recover the objective compound (37 mg at a yield of 64%) as a colorless crystal.

Melting Point: 116–117° C. IR (KBr) cm$^{-1}$: 3436, 3222, 2962, 1772, 1645. 1H-NMR (d$_6$-DMSO) δ: 1.12 (12H, d, J=6.8 Hz), 1.50–1.91 (6H, m), 2.32 (3H, s), 2.36 (2H, m), 3.09 (2H, sept, J=6.8 Hz), 3.34 (2H, t, J=7.1 Hz), 7.08 (1H, dd, J=8.1, 1.0 Hz), 7.09 (1H, d, J=8.6 Hz), 7.09 (1H, d, J=6.6 Hz), 7.20 (1H, dd, J=8.6, 6.6 Hz), 7.29 (1H, t, J=8.1 Hz), 7.46 (1H, dd, J=8.1, 1.0 Hz), 8.67 (1H, br.s), EIMS m/z (relative intensity): 482 (M$^+$, 100). Elementary Analysis: C$_{27}$H$_{34}$N$_2$O$_4$S Required: C, 67.19; H, 7.10; N, 5.80; S, 6.64. Found: C, 67.19; H, 7.18; N, 5.82; S, 6.55.

Example 24

Production of 6-(4-methoxycarbonylbenzoxazol-2-ylthio)-N-(2,6-diisopropylphenyl)hexanamide p-Toluenesulfonic acid monohydrate (95 mg, 0.5 mmol) was added to a solution of 3-hydroxyanthranilic acid (1.93 g, 12.6 mmol) in hydrochloric acid-saturated methanol (40 ml) solution, for reflux under heating for 12 hours. The solvents were distilled off, and the resulting residue was diluted with ethyl acetate. The organic layer was washed sequentially with an aqueous potassium hydrogen carbonate solution, water and saturated sodium chloride solution, and was dried over anhydrous sodium sulfate, from which the solvents were distilled off. The residue was dissolved in ether, and then, insoluble matters were filtered off. The filtrate was concentrated to recover the residue. Triethylamine (1.85 g, 18.25 mmol) was added to a solution of the residue (1.22 g, 7.37 mmol) in dichloromethane (10 ml), followed by dropwise addition of a solution of thiophosgene (923 mg, 8.03 mmol) in dichloromethane (2 ml), for subsequent stirring at ambient temperature for 5 minutes. The reaction solution was concentrated, and the resulting residue was diluted with ethyl acetate. The organic layer was washed sequentially with 1 N hydrochloric acid, water and saturated sodium chloride solution, and was dried over anhydrous sodium sulfate, from which the solvents were distilled off. The resulting solid matter was crystallized from ethyl acetate-hexane, to recover 4-methoxycarbonyl-2-mercaptobenzoxazole (1.28 g at a yield of 84%). To a solution in DMF (20 ml) of the oxazole (1.05 g, 5.0 mmol) and 6-bromo-N-(2,6-diisopropylphenyl)hexanamide (1.77 g, 5.0 mmol) were added potassium carbonate (1.04 g, 7.5 mmol) and 18-crown-6 (132 mg, 0.5 mmol), and the resulting mixture was stirred at 80° C. for 2 hours. After the reaction solution was diluted with water, the organic layer was extracted with ether. The organic layer was washed sequentially with water and saturated sodium chloride solution, and was dried over anhydrous magnesium sulfate, from which the solvents were distilled off. The residue was purified by silica gel column chromatography (100 g of silica gel; elution solvents:hexane:acetone=5:1); the resulting crystal was recrystallized from acetone-hexane, to recover the objective compound of 1.84 g (at a yield of 76%) as a colorless needle-like crystal.

Melting Point: 131–132° C. IR (KBr) cm$^{-1}$: 3408, 3221, 3172, 2965, 1713, 1641. 1H-NMR (d$_6$-DMSO) δ: 1.13 (12H, d, J=6.8 Hz), 1.53–1.97 (6H, m), 2.39 (2H, m), 3.10 (2H, sept, J=6.8 Hz), 3.40 (2H, t, J=7.2 Hz), 3.91 (3H, s), 7.08 (1H, d, J=8.8 Hz), 7.09 (1H, d, J=6.6 Hz), 7.19 (1H, dd, J=8.8, 6.6 Hz), 7.34 (1H, t, J=8.1 Hz), 7.74 (1H, dd, J=8.1, 1.2 Hz), 7.82 (1H, dd, J=8.1, 1.2 Hz), 8.60 (1H, br s). EIMS m/z (relative intensity): 482 (M$^+$), 176 (100). Elementary Analysis: C$_{27}$H$_{34}$N$_2$O$_4$S Required: C, 67.19; H, 7.10; N 5.80; S, 6.64. Found: C, 67.29; H, 7.21; N, 5.71; S, 6.62.

Example 25

Production of 6-(4-carboxybenzoxazol-2-ylthio)-N-(2,6-diisopropylphenyl)hexanamide To a solution in THF (10 ml) of 6-(4-methoxycarbonylbenzoxazol-2-ylthio)-N-(2,6-diisopropylphenyl)hexanamide (965 mg, 2.0 mmol) was added t-BuOH (4 ml), followed by addition of a solution of lithium hydroxide monohydrate (336 mg, 8 mmol) in water (4 ml), with stirring at ambient temperature for 12 hours. After distillation of the solvents under reduced pressure, the resulting residue was extracted with ethyl acetate. The organic layer was washed sequentially with 0.5 N hydrochloric acid, water and saturated sodium chloride solution, and was dried over anhydrous sodium sulfate, from which the solvents were distilled off. The resulting crude crystal was recrystallized from acetone-hexane, to recover the objective compound (799 mg at a yield of 85%) as a colorless crystal.

Melting Point: 174–176° C. IR (KBr) cm$^{-1}$: 3421, 3244, 2963, 1649, 1493. 1H-NMR (d$_6$-DMSO) δ: 1.12 (12H, d, J=6.8 Hz), 1.47–1.88 (6H, m), 2.37 (2H, m), 3.09 (2H, sept, J=6.8 Hz), 3.34 (2H, t, J=7.1 Hz), 7.08 (1H, d, J=8.5 Hz), 7.09 (1H, d, J=6.6 Hz), 7.19 (1H, dd, J=8.5, 6.6 Hz), 7.34 (1H, t, J=7.9 Hz), 7.74(1H, dd, J=7.9,0.5 Hz), 7.80 (1H, dd, J=7.9,0.5 Hz), 8.76 (1H, br s). Elementary Analysis: C$_{23}$H$_{32}$N$_2$O$_4$S Required: C, 66.64; H, 6.88; N, 5.98; S, 6.84. Found: C, 66.36; H, 6.86; N, 6.03; S, 6.64.

Example 26

Production of 6-(4-hydroxymethylbenzoxazol-2-ylthio)-N-(2,6-diisopropylphenyl)hexanamide To a solution in THF (10 ml) of 6-(4-carboxybenzoxazol-2-ylthio)-N-(2,6-diisopropylphenyl)hexanamide (613 mg, 1.5 mmol) was added triethylamine (200 mg, 1.98 mmol), followed by gradual addition of methyl chloroformate (195 mg, 1.80 mmol) under cooling in ice bath, with stirring for 30 minutes. The deposited triethylamine hydrochloride salt was filtered off; to the resulting filtrate under cooling in ice bath was gradually added an aqueous suspension (1.5 m) of sodium borohydride (227 mg, 6.0 mmol); and the resulting mixture was stirred for 30 minutes. To the reaction solution was added water, to extract the organic layer with ethyl acetate. The organic layer was washed sequentially with water and saturated sodium chloride solution and dried over anhydrous sodium sulfate, from which the solvents were distilled off. The residue was purified by silica gel column chromatography (25 g of silica gel; elution solvents:hexane:acetone=5:2 to 5:3), and the resulting crude crystal was recrystallized from acetone-ether-hexane, to recover the objective compound (468 mg at a yield of 69%) as a colorless crystal.

Melting Point: 93–95° C. IR (KBr) cm$^{-1}$: 3358, 3243, 2963, 1646, 1506. 1H-NMR (d$_6$-DMSO) δ: 1.13 (12H, d, J=6.8 Hz), 1.50–1.92 (6H,m), 2.37 (2H, m), 3.09 (2H, sept, J=6.8 Hz), 3.35 (2H, t, J=7.1 Hz), 4.67 (1H, t, J=5.5 Hz),4.83 (2H, d, J=5.5 Hz), 7.09 (1H, d, J=8.1 Hz), 7.09 (1H, d, J=6.6 Hz), 7.19 (1H, dd, J=8.1, 6.6 Hz), 7.24 (1H, t, J=7.8 Hz), 7.37 (1H, dd, J=7.8, 1.4 Hz), 7.40 (1H, dd, J=7.8, 1.4 Hz), 8.66 (1H, br s). EIMS m/z (relative intensity): 454 (M$^+$), 204 (100). Elementary Analysis: C$_{26}$H$_{34}$N$_2$O$_3$S Required: C, 68.69; H, 7.54; N, 6.16; S, 7.05. Found: C, 68.70; H, 7.57; N, 6.15; S, 7.01.

Example 27

Production of 6-[4-(N,N-dimethylaminomethyl)benzoxazol-2-ylthio]-N-(2,6-diisopropylphenyl)hexanamide To a solution in THF (5 ml) of 6-(4-hydroxymethylbenzoxazol-2-ylthio)-N-(2,6-diisopropylphenyl)hexanamide (182 mg, 0.4 mmol) were added triethylamine (81 mg, 0.8 mmol) and 4-dimethylaminopyridine (9.8 mg, 0.08 mmol), followed by dropwise addition of methane sulfonylchloride (64 mg, 0.56 mmol) under cooling in ice bath with stirring, and the resulting mixture was stirred for 30 minutes. The reaction solution was extracted with ethyl acetate; the organic layer was washed sequentially with 0.5 N hydrochloric acid, water and saturated sodium chloride solution and dried over anhydrous sodium sulfate, from which the solvents were distilled off. To a solution in THF (7 ml) of the resulting residue (209 mg) was added an aqueous 40% N,N-dimethylamine solution (180 mg, 1.6 mmol), for reflux under heating for one hour. After the reaction solution was left to stand and cooled, the reaction solution was extracted with ethyl acetate; the organic layer was washed with an aqueous sodium hydrogen carbonate solution, water and saturated sodium chloride solution and dried over anhydrous sodium sulfate, from which the solvents were distilled off. The residue was purified by silica gel column chromatography (10 g of silica gel; elution solvents:hexane:acetone=5:3, chloroform:ammonia-saturated methanol=19:1), and the resulting crystal was recrystallized from acetone-hexane, to recover the objective compound (137 mg at a yield of 71%) as a colorless crystal.

Melting Point: 113–115° C. IR (KBr) cm$^{-1}$: 3435, 3237, 2964, 1647, 1506. H-NMR (d$_6$-DMSO) δ: 1.12 (12H, d, J=6.8 Hz), 1.52–1.93 (6H,m), 2.24 (6H, s), 2.37 (2H, m), 3.09 (2H, sept, J=6.8 Hz), 3.35 (2H, t, J=7.2 Hz), 3.77 (2H, s), 7.09 (1H, d, J=8.3 Hz), 7.09 (1H, d, J=6.8 Hz), 7.19 (1H, dd, J=8.3, 6.8Hz), 7.22 (1H, t, J=7.6 Hz), 7.28 (1H, dd, J=7.6, 1.7 Hz), 7.41 (1H, dd, J=7.6, 1.7 Hz), 8.65 (1H, br s). EIMS m/z (relative intensity): 481 (M$^+$), 207 (100) Elementary Analysis: C$_{28}$H$_{39}$N$_3$O$_2$S Required: C, 69.82; H, 8.16; N, 8.72; S, 6.66. Found: C, 69.76; H, 8.23; N, 8.64; S, 6.72.

Example 28

Production of 6-(4-N,N-dimethylaminobenzoxazol-2-ylthio)-N-(2,6-diisopropylphenyl)hexanamide To a solution in THF (50 ml) of 2-amino-3-nitrophenol (1.54 g, 10 mmol) was added portions of sodium hydride (528 mg, 22 mmol) under cooling in ice bath, and the resulting mixture was stirred at 60° C. for 5 minutes. Then, portions of thiophosgene (1.38 g, 12 mmol) were added to the mixture, which was then stirred at 60° C. for 5 minutes. After distillation of the solvent, the resulting residue was adjusted to acidity by using 1 N hydrochloric acid; the resulting solid matter was filtered and recovered, which was then purified by silica gel column chromatography (200 g of silica gel; elution solvents: chloroform, chloroform:methanol=100:1 to 50:1), and the resulting solid matter was crystallized from acetone-hexane, to recover 2-mercapto-4-nitrobenzoxazole (807 mg at a yield of 41%) as a yellow crystal. To a solution in DMF (6 ml) of the resulting oxazole (216 mg, 1.1 mmol) and 6-bromo-N-(2,6-diisopropylphenyl)hexanamide (390 mg, 1.1 mmol) were added potassium carbonate (228 mg, 1.65 mmol) and 18-crown-6 (29 mg, 0.11 mmol), and the resulting mixture was stirred at 80° C. for 2 hours. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (70 g of silica gel; elution solvents:hexane:acetone=5:1 to 10:3); the resulting crystal was recrystallized from acetone-hexane, to recover 6-(4-nitrobenzoxazol-2-ylthio)-N-(2,6-diisopropylphenyl)hexanamide (304 mg at a yield of 59%) as a pale yellow crystal (melting point of 132–133° C.).

The nitro material (386 mg, 0.822 mmol) was dissolved in acetic acid (8 ml), followed by addition of zinc (1.07 g, 16.44 mmol) under cooling in ice bath, and the resulting mixture was stirred at ambient temperature for 5 minutes. The reaction solution was diluted with ethyl acetate and filtered through celite, which was then adjusted to neutrality by using an aqueous sodium hydrogen carbonate solution. The organic layer was washed sequentially with an aqueous sodium hydrogen carbonate solution, water and saturated sodium chloride solution, and was dried over anhydrous sodium sulfate, from which the solvents were distilled off. The residue was purified by silica gel column chromatography (38 g of silica gel; elution solvents:dichloromethane:hexane:acetone=4:4:1); the resulting crystal was recrystallized from acetone-hexane, to recover 6-(4-aminobenzoxazol-2-ylthio)-N-(2,6-diisopropylphenyl)hexanamide (231 mg at a yield of 64%) as a pale yellow crystal (melting point of 167–168° C.). To a solution of the amine material (273 mg, 0.621 mmol) in acetonitrile (7.5 ml) were sequentially added a solution of an aqueous 37% formaldehyde solution (504 mg, 5.78 mmol) in acetonitrile (7.5 ml) and a suspension of sodium cyanoborohydride (156 mg, 2.48 mmol) in acetonitrile (1 ml); and acetic acid (48 µl) was added to the resulting mixture with stirring at ambient temperature. The resulting mixture was further stirred for 30 minutes as it was. After distillation of the solvents, the resulting residue was diluted with water, and extracted with ethyl acetate. The organic layer was sequentially washed with water and saturated sodium chloride solution and dried over anhydrous sodium sulfate, from which the solvents were distilled off. The residue was purified by preparative thin layer chromatography (elution solvents:hexane:acetone=5:2); the resulting crystal was recrystallized from acetone-hexane, to recover the objective compound (177 mg at a yield of 61%) as a colorless crystal.

Melting Point: 129–130° C. IR (KBr) cm$^{-1}$: 3435, 3226, 2967, 1645, 1524. 1H-NMR (d$_6$-DMSO) δ: 1.13 (12H, d, J=7.1 Hz), 1.51–1.92 (6H, m), 2.36 (2H, m), 3.09 (2H, sept, J=7.1 Hz), 3.16 (6H, s), 3.30 (2H, t, J=7.1 Hz), 6.49 (1H, dd, J=8.8, 0.7 Hz), 6.84 (1H, dd, 8.1, 0.7 Hz), 7.07 (1H, d, J=8.1 Hz), 7.08 (1H, d, J=8.6 Hz), 7.09 (1H, d, J=6.4 Hz), 7.19 (1H, dd, J=8.6, 6.4 Hz), 8.63 (1H, br s). EIMS m/z (relative intensity): 467 (M$^+$, 100) Elementary Analysis: C$_{27}$H$_{37}$N$_3$O$_2$S Required: C, 69.34; H, 7.97; N, 8.99; S, 6.86. Found: C, 69.42; H, 8.10; N, 8.85; S, 6.77.

Example 29

Production of 6-(5-benzyloxybenzoxazol-2-ylthio)-N-(2,6-diisopropylphenyl)hexanamide To a solution in acetatic acid (21 ml) of 4-benzyloxy-2-nitrophenol (1.67 g, 6.8mmol) was added zinc (8.89 g, 136 mmol) under cooling in ice bath, with stirring at ambient temperature for 2 hours. Zinc was filtered off by using celite; the filtrate was adjusted to neutrality with sodium hydrogen carbonate, and extracted with ethyl acetate. The organic layer was sequentially washed with an aqueous sodium hydrogen carbonate solution, water and saturated sodium chloride solution and dried over anhydrous sodium sulfate, from which the solvents were distilled off to recover 4-benzyloxy-2-aminophenol (1.40 g at a yield of 95%) as a brown oil. To a solution of the aminophenol (1.4 g, 6.5 mmol) in ethanol (35 ml) was added potassium o-ethyl dithiocarbonate (1.34 g, 8.36 mmol), for reflux under heating for 24 hours. After the reaction solution was left to stand for cooling, the solvents were distilled off; the resulting residue was dissolved in water and adjusted to acidity by using conc. hydrochloric acid, and extracted with ethyl acetate. The organic layer was washed with saturated sodium chloride solution and dried over anhydrous sodium sulfate, from which the solvents were distilled off. The resulting solid material was crystallized from acetone-hexane, to recover 2-mercapto-5-benzyloxybenzoxazole (1.27 g at a yield of 71%) as a pale pink crystal. To a solution of the oxazole (514 mg, 2.0 mmol) and 6-bromo-N-(2,6-diisopropylphenyl)hexanamide (708 mg, 2.0 mmol) in DMF (5 ml) were added potassium carbonate (345 mg, 2.5 mmol) and 18-crown-6 (65 mg, 0.24 mmol), and the resulting mixture was stirred at 80° C. for 3 hours. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (50 g of silica gel; elution solvents:hexane:acetone=5:1 to 10:3); the resulting crystal was recrystallized from acetone-hexane, to recover the objective compound (734 mg at a yield of 69%) as a pale red crystal.

Melting Point: 102–104° C. IR (KBr) cm$^{-1}$: 3413, 3243, 2964, 1644, 1496. 1H-NMR (d$_6$-DMSO) δ: 1.12 (12H, d, J=6.8 Hz), 1.46–1.92 (6H, m), 2.47 (2H, m), 3.09 (2H, sept, J=6.8 Hz), 3.33 (2H, t, J=7.1 Hz), 5.13 (2H, s), 6.94 (1H, dd, J=8.8, 2.4 Hz), 7.08 (1H, d, 8.8 Hz), 7.09 (1H, d, J=6.8 Hz), 7.19 (1H, dd, J=8.8, 6.8 Hz), 7.21 (1H, d, J=2.4 Hz), 7.25–7.47 (6H, m), 8.68 (1H, br s). EIMS m/z (relative intensity): 530 (M$^+$, 100). Elementary Analysis: C$_{32}$H$_{38}$N$_2$O$_3$S Required: C, 72.42; H, 7.22; N, 5.28; S, 6.04. Found: C, 72.41; H, 7.24; N, 5.11; S, 5.82.

Example 30

Production of 6-(5-hydroxybenzoxazol-2-ylthio)-N-(2,6-diisopropylphenyl)hexanamide Under cooling in ice bath, 6-(5-benzyloxybenzoxazol-2-ylthio)-N-(2,6-diisopropylphenyl)hexanamide (514 mg, 2.0 mmol) was dissolved in trifluoroacetic acid (20 ml), followed by addition of thioanisole (1.24 g, 10 mmol), with stirring at ambient temperature for 12 hours. The solvent was distilled off from the reaction solution; the resulting residue was diluted with water, and extracted with ethyl acetate. The organic layer was washed sequentially with a saturated sodium hydrogen carbonate solution and saturated sodium chloride solution, and was dried over anhydrous magnesium sulfate, from which the solvents were distilled off. The residue was purified by silica gel column chromatography (30 g of silica gel; elution solvents:hexane:acetone=5:1 to 5:2), to recover the objective compound (459 mg at a yield of 97%) as a pale red amorphous. IR (KBr) cm$^{-1}$: 3247, 2963, 1649, 1445, 1153. 1H-NMR (d$_6$-DMSO) δ: 1.12 (12H, d, J=6.8 Hz), 1.48–1.91 (6H, m), 2.35 (2H, m), 3.08 (2H, sept, J=6.8 Hz), 3.31 (2H, t, J=7.1 Hz), 6.70 (1H, dd, J=8.8, 2.4 Hz), 6.92 (1H, d, J=2.4 Hz), 7.09 (1H, d, J=8.3 Hz), 7.10 (1H, d, J=7.1 Hz), 7.19 (1H, dd, J=8.3, 7.1 Hz), 7.31 (1H, d, J=8.8 Hz), 8.68 (1H, br s), 8.92 (1H, s). EIMS m/z (relative intensity): 440 (M$^+$, 100). Elementary Analysis: C$_{25}$H$_{32}$N$_2$O$_3$S Required: C, 68.15; H, 7.32; N, 6.36; S, 7.28. Found: C, 68.16; H, 7.45; N, 6.26; S, 6.86.

Example 31

Production of 9-(5-hydroxybenzoxazol-2-ylthio)-N-(2,6-diisopropylphenyl)nonanamide To a solution of 2-mercapto-5-benzyloxybenzoxazole (515 mg, 2.0 mmol) and 9-bromo-N-(2,6-diisopropylphenyl)nonanamide (793 mg, 2.0 mmol) in DMF (15 ml) were added potassium carbonate (415 mg, 3.0 mmol) and 18-crown-6 (53 mg, 0.02 mmol), and the resulting mixture was stirred at 80° C. for one hour. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (75 g of silica gel; elution solvents:hexane:acetone=5:1); the resulting crystal was recrystallized from acetone-hexane, to recover the objective compound (990 mg at a yield of 86%) as a colorless crystal.

Under cooling in ice bath, 9-[5-benzyloxybenzoxazol-2-ylthio]-N-(2,6-diisopropylphenyl)nonanamide (859 mg, 1.5 mmol) was dissolved in trifluoroacetic acid (40 ml), followed by addition of thiophenol (1.86 g, 15 mmol), with stirring at ambient temperature for 24 hours. The solvent was distilled off under reduced pressure; the resulting residue was diluted with water, and extracted with ethyl acetate. The organic layer was washed sequentially with saturated sodium hydrogen carbonate solution, water and saturated sodium chloride solution, and was dried over anhydrous sodium sulfate, from which the solvents were distilled off. The residue was purified by silica gel column chromatography (85 g of silica gel; elution solvents:hexane:acetone= 5:1 to 10:3 to 5:2), to recover the objective compound (634 mg at a yield of 88%) as a pale pink amorphous.

IR (KBr) cm$^{-1}$: 3250, 2929, 1651, 1447, 1154. 1H-NMR (d$_6$-DMSO) δ: 1.13 (12H, d, J=6.8 Hz), 1.37–1.69 (10H, m), 1.80 (2H, quint, J=7.2 Hz) 2.34 (2H, m), 3.10 (2H, sept, J=6.8 Hz), 3.30 (2H, t, J=7.2 Hz), 6.72 (1H, dd, J=8.8, 2.0 Hz), 6.94 (1H, dd, J=2.0, 0.5 Hz), 7.10 (1H, d, J=8.6 Hz), 7.11 (1H, d, J=6.6 Hz), 7.21 (1H, dd, J=8.6, 6.6 Hz), 7.32 (1H, dd, J=8.8, 0.5 Hz) 8.87 (1H, br s), 8.93 (1H, br s). EIMS m/z (relative intensity): 482 (M$^+$, 100). Elementary Analysis: C$_{28}$H$_{38}$N$_2$O$_3$S Required: C, 69.68; H, 7.93; N, 5.80; S, 6.64. Found: C, 69.41; H, 8.12; N, 5.62; S, 6.92.

Example 32

Production of 6-(5-acetylthiobenzoxazol-2-ylthio)-N-(2,6-diisopropylphenyl)hexanamide In the same manner as in Example 22 except for the use of 6-(5-hydroxybenzoxazol-2-ylthio)-N-(2,6-diisopropylphenyl)hexanamide instead of 6-(4-hydroxybenzoxazol-2-ylthio)-N-(2,6-diisopropylphenyl)hexanamide, reaction progressed to recover the objective compound as a pale red crystal.

Melting Point: 102–104° C. IR (KBr) cm$^{-1}$: 3247, 2963, 1649, 1445, 1153. 1H-NMR (d$_6$-DMSO) δ: 1.14 (12H, d, J=6.8 Hz), 1.51–1.96 (6H, m), 2.28 (3H, S), 2.38 (2H, m), 3.11 (2H, sept, J=6.8 Hz), 3.38 (2H, t, J=7.1 Hz), 7.06 (1H, dd, J=8.6, 2.4 Hz), 7.11 (1H, d, J=8.8 Hz), 7.12 (1H, d, 7.1 Hz), 7.23 (1H, dd, J=8.8, 7.1 Hz), 7.59 (1H, d, J=8.6 Hz), 8.71 (1H, br s). EIMS m/z (relative intensity): 482 (M$^+$, 100). Elementary Analysis: C$_{27}$H$_{34}$N$_2$O$_4$S Required: C, 67.19; H, 7.10; N, 5.80; S, 6.64. Found: C, 67.40; H, 7.20; N, 5.72; S, 6.50.

Example 33

Production of 9-(5-acetyloxythiobenzoxazol-2-ylthio)-N-(2,6-diisopropylphenyl)nonanamide In the same manner as in Example 22 except for the use of 9-(5-hydroxybenzoxazol-2-ylthio)-N-(2,6-diisopropylphenyl)nonanamide instead of 6-(4-hydroxybenzoxazol-2-ylthio)-N-(2,6-diisopropylphenyl)hexanamide, reaction progressed to recover the objective compound as a colorless crystal.

Melting Point: 89–90° C. IR (KBr) cm$^{-1}$: 3433, 3266, 1770, 1649, 1496. 1H-NMR (d$_6$-DMSO) δ: 1.13 (12H, d, J=6.8 Hz), 1.37–1.71 (10H, m), 1.82 (2H, quint, J=7.2 Hz), 2.25 (3H, S), 2.33 (2H, m), 3.09 (2H, sept, J=6.8 Hz), 3.32 (2H, t, J=7.2 Hz), 7.01 (1H, dd, J=8.8, 2.4 Hz), 7.08 (1H, d, J=8.6 Hz), 7.09 (1H, d, J=7.1 Hz), 7.19 (1H, dd, J=8.6, 7.1 Hz), 7.33 (1H, dd, J=2.4, 0.5 Hz), 7.52 (1H, dd, J=8.8, 0.5 Hz), 8.61 (1H, br s) EIMS m/z (relative intensity): 524 (M$^+$, 100). Elementary Analysis: C$_{30}$H$_{40}$N$_2$O$_4$S Required: C, 68.68; H, 7.68; N, 5.34; S, 6.11. Found: C, 68.79; H, 7.79; N, 5.31; S, 6.09.

Example 34

Production of 6-(5-methoxycarbonylbenzoxazol-2-ylthio)-N-(2,6-diisopropylphenyl)hexanamide In the same manner as in Example 24 except for the use of 3-amino-4-hydroxybenzoic acid instead of 3-hydroxyanthranilic acid, reaction progressed to recover the objective compound as a colorless needle-like crystal.

Melting Point: 104–106° C. IR (KBr) cm$^{-1}$: 3417, 3251, 2960, 1720, 1651. 1H-NMR (d$_6$-DMSO) δ: 1.11 (12H, d, J=6.8 Hz), 1.47–1.95 (6H, m), 2.36 (2H,m), 3.07 (2H, sept, J=6.8 Hz), 3.38 (2H, t, J=7.1 Hz), 3.88 (3H, S), 7.08 (1H, d, J=8.5 Hz), 7.09 (1H, d, J=7.1 Hz), 7.20 (1H, dd, J=8.5, 7.1 Hz), 7.67 (1H, d, J=8.3 Hz), 7.93 (1H, dd, J=8.5, 2.4 Hz), 8.12 (1H, dd, J=2.4 Hz), 8.68 (1H, br s). Elementary Analysis: C$_{27}$H$_{34}$N$_2$O$_4$S Required: C, 67.19; H, 7.10; N, 5.80; S, 6.64. Found: C, 67.32; H, 7.11; N, 5.81; S, 6.62.

Example 35

Production of 6-(5-carboxybenzoxazol-2-ylthio)-N-(2,6-diisopropylphenyl)hexanamide In the same manner as in Example 25 except for the use of 6-(5-methoxycarbonylbenzoxazol-2-ylthio)-N-(2,6-diisopropylphenyl)hexanamide instead of 6-(4-methoxycarbonylbenzoxazol-2-ylthio)-N-(2,6-diisopropylphenyl)hexanamide, reaction progressed to recover the objective compound as a colorless crystal.

Melting Point: 198–200° C. IR (KBr) cm$^{-1}$: 3610, 3236, 2963, 1691, 1646. 1H-NMR (d$_6$-DMSO) δ: 1.13 (12H, d, J=6.8 Hz), 1.53–1.94 (6H, m), 2.38 (2H, m), 3.10 (2H, sept, J=6.8 Hz), 3.37 (2H, t, J=7.2 Hz), 7.08 (1H, d, J=8.5 Hz), 7.09 (1H, d, J=6.6 Hz), 7.19 (1H,dd, J=8.5, 6.6 Hz), 7.58 (1H, dd, J=8.5, 0.5 Hz), 7.93 (1H, dd, J=8.5, 1.7 Hz), 8.12 (1H, dd, J=1.7, 0.5 Hz), 8.62 (1H, br s). EIMS m/z (relative intensity): 468 (M$^+$), 176(100) Elementary Analysis: C$_{26}$H$_{32}$N$_2$O$_4$S Required: C, 66.64; H, 6.88; N, 5.98; S, 6.84. Found: C, 66.78; H, 7.00; N, 5.98; S, 6.67.

Example 36

Production of 6-(5-hydroxymethylbenzoxazol-2-ylthio)-N-(2,6-diisopropylphenyl)hexanamide In the same manner as in Example 26 except for the use of 6-(5-carboxybenzoxazol-2-ylthio)-N-(2,6-diisopropylphenyl)hexanamide instead of 6-(4-carboxybenzoxazol-2-ylthio)-N-(2,6-diisopropylphenyl)hexanamide, reaction progressed to recover the objective compound as a colorless crystal.

Melting Point: 152–153° C. IR (KBr) cm$^{-1}$: 3432, 3222, 2965, 1646, 1491. 1H-NMR (d$_6$-DMSO) δ: 1.13 (12H, d, J=6.8 Hz), 1.50–1.92 (6H,m), 2.36 (2H, m), 3.09 (2H, sept, J=6.8 Hz), 3.34 (2H, t, J=7.1 Hz), 4.59 (2H, s), 7.09 (1H, d, J=8.1 Hz), 7.09 (1H, d, J=6.8 Hz), 7.19 (1H, dd, J=8.1 , 6.8Hz), 7.24 (1H, dd, J=8.3, 1.5 Hz), 7.46 (1H, d, J=8.3 Hz), 7.52 (1H, d, J=1.5 Hz), 8.67 (1H, br s). EIMS m/z (relative intensity): 454 (M$^+$), 176 (100) Elementary Analysis: $C_{26}H_{34}N_2O_3S$ Required: C, 68.69; H, 7.54; N, 6.16; S, 7.05. Found: C, 68.59; H, 7.58; N, 6.12; S, 7.11.

Example 37

Production of 6-[5-(N,N-dimethylaminomethyl) benzoxazol-2-ylthio]-N-(2,6-diisopropylphenyl) hexanamide In the same manner as in Example 27 except for the use of 6-(5-hydroxymethylbenzoxazol-2-ylthio)-N-(2,6-diisopropylphenyl)hexanamide instead of 6-(4-hydroxymethylbenzoxazol-2-ylthio)-N-(2,6-diisopropylphenyl) hexanamide, reaction progressed to recover the objective compound as a colorless crystal.

Melting Point: 112–113° C. IR (KBr) cm$^{-1}$: 3429, 3238, 2961, 1652, 1502. 1H-NMR (d$_6$-DMSO) δ: 1.12 (12H, d, J=6.8 Hz), 1.50–1.92 (6H,m),2.19 (3H, s), 2.20 (3H, s), 2.36 (2H, m), 3.09 (2H, sept, J=6.8 Hz), 3.34 (2H, t, J=7.2 Hz), 3.49 (2H, s), 7.09 (1H, d, J=8.6 Hz), 7.09 (1H, d, J=7.1 Hz), 7.19 (1H, dd, J=8.6, 7.1 Hz), 7.21 (1H, dd, J=8.6, 1.5 Hz), 7.46 (1H, d, J=8.6 Hz), 7.48 (1H, d, J=1.5 Hz), 8.66 (1H, br s). EIMS m/z (relative intensity): 481 (M$^+$), 207 (100). Elementary Analysis: $C_{28}H_{39}N_3O_2S$ Required: C, 69.82; H, 8.16; N, 8.72; S, 6.66. Found: C, 69.65; H, 8.18; N, 8.65; S, 6.54.

Example 38

Production of 6-(5-N,N-dimethylaminobenzoxazol-2-ylthio)-N-(2,6-diisopropylphenyl)hexanamide To a solution of 2-amino-4-nitrophenol (1.54 g, 10 mmol) in ethanol (50 ml) was added potassium o-ethyl dithiocarbonate (1.76 g, 11 mmol), at reflux under heating for 12 hours. After the reaction solution was left to stand for cooling, the solvents were distilled off under reduced pressure; the resulting residue was adjusted to acidity by using 1 N hydrochloric acid, and extracted with ethyl acetate. The organic layer was washed with saturated sodium chloride solution and dried over anhydrous sodium sulfate, from which the solvents were distilled off. The resulting solid material was crystallized from acetone-hexane, to recover 2-mercapto-5-nitrobenzoxazole (1.90 g at a yield of 97%) as a yellow crystal. To a solution of the oxazole (392 mg, 2.0 mmol) and 6-bromo-N-(2,6-diisopropylphenyl)hexanamide (708 mg, 2.0 mmol) in DMF (5 ml) were added potassium carbonate (304 mg, 2.2 mmol) and 18-crown-6 (53 mg, 0.2 mmol), and the resulting mixture was stirred at 80° C. for 3 hours. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (50 g of silica gel; elution solvents:hexane:acetone=5:1 to 10:3); the resulting crystal was recrystallized from acetone-hexane, to recover 6-(5-nitrobenzoxazol-2-ylthio)-N-(2,6-diisopropylphenyl) hexanamide (796 mg at a yield of 85%) as a pale yellow crystal (of a melting point of 118 to 119° C.). The nitro material (670 mg, 1.42 mmol) was dissolved in acetic acid (15 ml), followed by addition of zinc (1.86 g, 28.5 mmol) under cooling in ice bath, and the resulting mixture was stirred at ambient temperature for 2 hours. After the reaction solution was filtered through celite, the filtrate was adjusted to neutrality by using an aqueous saturated sodium hydrogen carbonate solution, and extracted with ethyl acetate. The organic layer was washed sequentially with an aqueous sodium hydrogen carbonate solution, water and saturated sodium chloride solution, and was dried over anhydrous sodium sulfate, from which the solvents were distilled off. The residue was purified by silica gel column chromatography (12 g of silica gel; elution solvents:chloroform:methanol=97:3); the resulting crystal was recrystallized from methylene chloride-ether, to recover 6-(5-aminobenzoxazol-2-ylthio)-N-(2,6-diisopropylphenyl) hexanamide (374 mg at a yield of 60%) as a pale yellow crystal (of a melting point of 151–152° C.). To a solution of the aniline (220 mg, 0.50 mmol) in acetonitrile (3 ml) were sequentially added an aqueous 37% formaldehyde solution (406 mg, 5.0 mmol) and a suspension of sodium cyanoborohydride (126 mg, 2.0 mmol) in acetonitrile (2 ml), followed by dropwise addition of acetic acid (45 μl) with stirring at ambient temperature; and then, the resulting mixture was further stirred for 30 minutes. After distillation of the solvents, the resulting residue was diluted with water, and extracted with ethyl acetate. The organic layer was sequentially washed with water and saturated sodium chloride solution and dried over anhydrous sodium sulfate, from which the solvents were distilled off. The residue was purified by silica gel column chromatography (10 g of silica gel; elution solvents:hexane:methylene chloride:acetone=4:4:1), and the resulting crystal was recrystallized from ether-hexane, to recover the objective compound (122 mg at a yield of 52%) as a colorless needle-like crystal.

Melting Point: 130–132° C. IR (KBr) cm$^{-1}$: 3435, 3227, 2961, 1651, 1494. 1H-NMR (d$_6$-DMSO) δ: 1.12 (12H, d, J=6.8 Hz), 1.47–1.92 (6H, m), 2.35 (2H,m), 2.89 (6H, s), 3.08 (2H, sept, J=6.8 Hz), 3.31 (2H, t, J=7.1 Hz), 6.71 (1H, dd, J=8.8, 2.4 Hz), 6.87 (1H, d, J=2.4 Hz), 7.08 (1H, d, J=8.3 Hz), 7.09 (1H, d, J=6.8 Hz), 7.19 (1H, dd, J=8.3, 6.8 Hz), 7.33 (1H, d, J=8.8 Hz), 8.68 (1H, br s). EIMS m/z (relative intensity): 467 (M$^+$, 100). Elementary Analysis: $C_{27}H_{37}N_3O_2S$ Required: C, 69.34; H, 7.97; N, 8.99; S, 6.82. Found: C, 69.44; H, 7.97; N, 8.94; S, 6.86.

Example 39

Production of 6-(6-hydroxybenzoxazol-2-ylthio)-N-(2,6-diisopropylphenyl)hexanamide To a solution of 2-mercapto-6-hydroxybenzoxazole (167 mg, 1.0 mmol) and 6-bromo-N-(2,6-diisopropylphenyl) hexanamide (354 mg, 1.0 mmol) in DMF (6 ml) were added potassium carbonate (207 mg, 1.5 mmol) and 18-crown-6 (26 mg, 0.01 mmol), and the resulting mixture was stirred at 80° C. for 2 hours. After the reaction solution was diluted with water, the organic layer was extracted with ethyl acetate. The organic layer was washed sequentially with water and saturated sodium chloride solution, and was dried over anhydrous sodium sulfate, from which the solvents were distilled off. The residue was purified by silica gel column chromatography (70 g of silica gel; elution solvents:hexane:acetone=10:3 to 5:1), to recover the objective compound (347 mg at a yield of 79%) as a pale brown amorphous.

IR (KBr) cm$^{-1}$: 3247, 2963, 1652, 1484. 1H-NMR (d$_6$-DMSO) δ: 1.13 (12H, d, J=6.8 Hz), 1.51–1.91 (6H, m), 2.37 (2H, m), 3.10 (2H, sept, J=6.8 Hz), 3.28 (2H, t, J=7.2 Hz), 6.75 (1H, dd, J=8.5, 2.2 Hz), 6.91 (1H, d, J=2.2 Hz), 7.08 (1H, d, J=8.6 Hz), 7.09 (1H, d, J=6.6 Hz), 7.19 (1H, dd, J=8.8, 6.6 Hz), 7.31 (1H, d, J=8.5 Hz) 8.61 (1H, br s), 9.08

(1H, br s). EIMS m/z (relative intensity): 440 (M⁺, 100). Elementary Analysis: $C_{25}H_{32}N_2O_3S$ Required: C, 68.15; H, 7.32; N, 6.36; S, 7.28. Found: C, 67.93; H, 7.37; N, 6.31; S, 7.03.

Example 40

Production of 6-(6-methoxycarbonylbenzoxazol-2-ylthio)-N-(2,6-diisopropylphenyl)hexanamide In the same manner as in Example 24 except for the use of 4-amino-3-hydroxybenzoic acid instead of 3-hydroxyanthranilic acid, reaction progressed to recover the objective compound as a colorless needle-like crystal.

Melting Point: 157–158° C. IR (KBr) cm⁻¹: 3412, 3236, 2959, 1714, 1647. 1H-NMR (d₆-DMSO) δ: 1.12 (12H, d, J=6.8 Hz), 1.51–1.94 (6H, m), 2.37 (2H,m), 3.09 (2H, sept, J=6.8 Hz), 3.39 (2H, t, J=7.2 Hz), 3.88 (3H, s), 7.08 (1H, d, J=8.6 Hz), 7.09 (1H, d, J=6.6 Hz), 7.20 (1H, dd, J=8.6, 6.6 Hz), 7.65 (1H, dd, J=8.3, 0.5 Hz), 7.95 (1H, dd, J=8.3, 1.7 Hz), 8.09 (1H, dd, J=1.7, 0.5 Hz), 8.67 (1H, br s). EIMS m/z (relative intensity): 483 (M⁺+1), 69 (100). Elementary Analysis: $C_{27}H_{34}N_2O_4S$ Required: C, 67.19; H, 7.10; N, 5.80; S, 6.64. Found: C, 67.35; H, 7.13; N, 5.78; S, 6.47.

Example 41

Production of 6-(6-carboxybenzoxazol-2-ylthio)-N-(2,6-diisopropylphenyl)hexanamide In the same manner as in Example 25 except for the use of 6-(6-methoxycarbonylbenzoxazol-2-ylthio)-N-(2,6-diisopropylphenyl)hexanamide instead of 6-(4-methoxycarbonylbenzoxazol-2-ylthio)-N-(2,6-diisopropylphenyl)hexanamide, reaction progressed to recover the objective compound as a colorless crystal.

Melting Point: 212–213° C. IR (KBr) cm⁻¹: 3216, 2964, 1648, 1491, 1430. 1H-NMR (d₆-DMSO) δ: 1.13 (12H, d, J=6.8 Hz), 1.51–1.94 (6H, m), 2.37 (2H,m), 3.09 (2H, sept, J=6.8 Hz), 3.39 (2H, t, J=7.1 Hz), 7.08 (1H, d, J=8.5 Hz), 7.09 (1H, d, J=6.6 Hz), 7.19 (1H,dd, J=8.5, 6.6 Hz), 7.62 (1H, dd, J=8.3, 0.4 Hz), 7.94 (1H, dd, J=8.3, 1.5 Hz), 8.06 (1H, dd, J=1.5, 0.4 Hz), 8.65 (1H, br s). EIMS m/z (relative intensity): 468 (M⁺), 176 (100). Elementary Analysis: $C_{26}H_{32}N_2O_4S$ Required: C, 66.64; H, 6.88; N, 5.98; S, 6.84. Found: C, 66.81; H, 7.00; N, 5.96; S, 6.64.

Example 42

Production of 6-(6-hydroxymethylbenzoxazol-2-ylthio)-N-(2,6-diisopropylphenyl)hexanamide In the same manner as in Example 26 except for the use of 6-(6-carboxybenzoxazol-2-ylthio)-N-(2,6-diisopropylphenyl)hexanamide instead of 6-(4-carboxybenzoxazol-2-ylthio)-N-(2,6-diisopropylphenyl) hexanamide, reaction progressed to recover the objective compound as a colorless crystal.

Melting Point: 93–95° C. IR (KBr) cm⁻¹: 3421, 3261, 2964, 1645, 1492. 1H-NMR (d₆-DMSO) δ: 1.13 (12H, d, J=6.8 Hz), 1.50–1.92 (6H, m), 2.37 (2H, m), 3.09 (2H, sept, J=6.8 Hz), 3.34 (2H, t, J=7.2 Hz), 4.61 (2H, s), 7.09 (1H, d, J=8.6 Hz), 7.09 (1H, d, J=6.6 Hz), 7.19 (1H, dd, J=8.6 , 6.6Hz), 7.26 (1H, dd, J=8.1, 1.3 Hz), 7.49 (1H, dd, J=8.1, 0.7 Hz), 7.49 (1H, dd, J=1.3, 0.7 Hz), 8.64 (1H, br s). EIMS m/z (relative intensity): 454 (M⁺), 69 (100). Elementary Analysis: $C_{26}H_{34}N_2O_3S$ Required: C, 68.69; H, 7.54; N, 6.16; S, 7.05. Found: C, 68.52; H, 7.50; N, 6.12; S, 7.09.

Example 43

Production of 6-[6-(N,N-dimethylaminomethyl) benzoxazol-2-ylthio]-N-(2,6-diisopropylphenyl) hexanamide In the same manner as in Example 27 except for the use of 6-(6-hydroxymethylbenzoxazol-2-ylthio)-N-(2,6-diisopropylphenyl)hexanamide instead of 6-(4-hydroxymethylbenzoxazol-2-ylthio)-N-(2,6-diisopropylphenyl) hexanamide, reaction progressed to recover the objective compound as a colorless crystal.

Melting Point: 82–84° C. IR (KBr) cm⁻¹: 3246, 2963, 1652, 1503, 1220. 1H-NMR (d₆-DMSO) δ: 1.12 (12H, d, J=6.8 Hz), 1.46–1.93 (6H, m), 2.24 (6H, s), 2.36 (2H, m), 3.08 (2H, sept, J=6.8 Hz), 3.34 (2H, t, J=7.3 Hz), 3.58 (2H, s), 7.08 (1H, d, J=8.3 Hz), 7.09 (1H, d, J=6.6 Hz), 7.20 (1H, dd, J=8.3, 6.6 Hz), 7.25 (1H, dd, J=8.1, 1.2 Hz), 7.49 (1H, d, J=1.2 Hz), 7.51 (1H, d, J=8.1 Hz), 8.66 (1H, br s). Elementary Analysis: $C_{28}H_{39}N_3O_2S\cdot0.5H_2O$ Required: C, 68.53; H, 8.22; N, 8.56; S, 6.53. Found: C, 68.53; H, 8.14; N, 8.44; S, 6.64.

Example 44

Production of 6-(6-N,N-dimethylaminobenzoxazol-2-ylthio)-N-(2,6-diisopropylphenyl)hexanamide In the same manner as in Example 28 except for the use of 2-amino-6-nitrophenol instead of 2-amino-3-nitrophenol, reaction progressed to recover the objective compound as a colorless needle-like crystal.

Melting Point: 149–150° C. IR (KBr) cm⁻¹: 3435, 3231, 2966, 1650, 1100. 1H-NMR (d₆-DMSO) δ: 1.13 (12H, d, J=6.8 Hz), 1.48–1.89 (6H, m), 2.36 (2H,m), 2.93 (6H, s), 3.09 (2H, sept, J=6.8 Hz), 3.27 (2H, t, J=7.1 Hz), 6.73 (1H, dd, J=8.8, 2.4 Hz), 6.85 (1H, d, J=2.4 Hz), 7.09 (1H, d, J=8.8 Hz), 7.09 (1H, d, J=6.8 Hz), 7.19 (1H, dd, J=8.8, 6.8 Hz), 7.35 (1H, d, J=8.8 Hz), 8.66 (1H, br s). EIMS m/z (relative intensity): 467 (M⁺, 100). Elementary Analysis: $C_{27}H_{37}N_3O_2S$ Required: C, 69.34; H, 7.97; N, 8.99; S, 6.86. Found: C, 69.46; H, 8.07; N, 8.90; S, 6.96.

Example 45

Production of 6-(6-methylbenzoxazol-2-ylthio)-N-(2,6-diisopropylphenyl)hexanamide To a solution of 2-amino-6-methylphenol (636 mg, 4.57 mmol) in ethanol (10 ml) was added potassium o-ethyl dithiocarbonate (801 mg, 5 mmol), at reflux under heating for 2 hours. The solvents were distilled off under reduced pressure; subsequently, the resulting residue was adjusted to acidity by using 1 N hydrochloric acid, and extracted with ethyl acetate. The organic layer was washed with saturated sodium chloride solution and dried over anhydrous sodium sulfate, from which the solvents were distilled off. The resulting crude powder was crystallized from acetone-hexane, to recover 2-mercapto-6-methylbenzoxazole (538 mg at a yield of 65%) as a yellowish brown crystal. To a solution of the oxazole (453 mg, 2.5 mmol) and 6-bromo-N-(2,6-diisopropylphenyl)hexanamide (885 mg, 2.5 mmol) in DMF (8 ml) were added potassium carbonate (387 mg, 2.8 mmol) and 18-crown-6 (66 mg, 0.25 mmol), and the resulting mixture was stirred at 80° C. for 3 hours. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (50 g of silica gel; elution solvents:hexane:acetone=5:1 to 10:3); the resulting crystal was recrystallized from acetone-ether-hexane, to recover the objective compound (908 mg at a yield of 82%) as a colorless needle-like crystal.

Melting Point: 112–114° C. IR (KBr) cm⁻¹: 3427, 3230, 2964, 1644, 1502. 1H-NMR (d₆-DMSO) δ: 1.12 (12H, d, J=6.8 Hz), 1.46–1.92 (6H, m), 2.36 (2H,m), 2.41 (3H, S), 3.05 (2H, sept, J=6.8 Hz), 3.32 (2H, t, J=7.1 Hz), 7.08 (1H, d, J=8.8 Hz), 7.09 (1H, d, J=6.6 Hz), 7.12 (1H, dd, J=8.1, 2.4 Hz), 7.20 (1H, dd, J=8.8, 6.6 Hz), 7.36 (1H, dd, J=2.4, 0.7 Hz), 7.43 (1H, d, J=8.1 Hz), 8.68 (1H, br s). EIMS m/z (relative intensity): 438 (M+, 100). Elementary Analysis: $C_{26}H_{34}N_2O_2S$ Required: C, 71.20; H, 7.81; N, 6.39; S, 7.31. Found: C, 71.08; H, 7.99; N, 6.27; S, 7.04.

Example 46

Production of 6-(7-methoxycarbonylbenzoxazol-2-ylthio)-N-(2,6-diisopropylphenyl)hexanamide To a solution of 3-aminosalicylic acid (1.53 g, 10 mmol) in ethanol (70 ml) was added potassium o-ethyl dithiocarbonate (3.2 g, 20 mmol), at reflux under heating for 2.5 hours. After the reaction solution was left to stand for cooling, the solvents were distilled off under reduced pressure; the resulting residue was adjusted to acidity by using 1 N hydrochloric acid; the resulting deposited precipitate was filtered and dried, to recover 7-carboxyl-2-mercaptobenzoxazole (1.3 g at a yield of 67%) as a brown powder. To a solution of the carboxylic acid (976 mg, 5.0 mmol) in methanol (50 ml) was added p-toluenesulfonic acid monohydrate (95 mg, 0.5 mmol), for reflux under heating for 4 days. After the solution was left to stand for cooling, the solvents were distilled off under reduced pressure; the resulting residue was extracted with ethyl acetate. The organic layer was washed sequentially with water and saturated sodium chloride solution and dried over anhydrous sodium sulfate, from which the solvents were distilled off. The resulting solid material was crystallized from acetone-hexane, to recover 7-methoxycarbonyl-2-mercaptobenzoxazole (0.955 g at a yield of 91%) as a brown powder. To a solution of the oxazole (837 mg, 4.0 mmol) and 6-bromo-N-(2,6-diisopropylphenyl)hexanamide (1.42 g, 4.0 mmol) in DMF (20 ml) were added potassium carbonate (608 mg, 4.4 mmol) and 18-crown-6 (106 mg, 0.4 mmol), and the resulting mixture was stirred at 80° C. for 2 hours. After the reaction solution was diluted with water, the organic layer was extracted with ethyl acetate. The organic layer was washed sequentially with water and saturated sodium chloride solution, and was dried over anhydrous magnesium sulfate, from which the solvents were distilled off. The residue was purified by silica gel column chromatography (50 g of silica gel; elution solvents:hexane:acetone=5:1); the resulting crystal was recrystallized from acetone-ether-hexane, to recover the objective compound (1.93 g at a yield of 100%) as a colorless needle-like crystal.

Melting Point: 118–119° C. IR (KBr) cm$^{-1}$: 3420, 2963, 1719, 1645, 1507. 1H-NMR (d$_6$-DMSO) δ: 1.12 (12H, d, J=6.9 Hz), 1.56 (2H, quint, J=7.3 Hz), 1.73 (2H, quint, J=7.3 Hz), 1.90 (2H, quint, J=7.3 Hz), 2.37 (2H, t, J=7.3 Hz), 3.08 (2H, sept, J=6.8 Hz), 3.39 (2H, t, J=7.3 Hz), 3.93 (3H, s), 7.09 (2H, d, J=7.6 Hz), 7.19 (1H, t, J=7.6 Hz), 7.42 (1H, t, J=7.9 Hz), 7.80 (1H, dd, J=7.5, 0.9 Hz), 7.81 (1H, dd, J=7.9, 0.9 Hz), 8.68 (1H, br s). EIMS m/z (relative intensity): 482 (M+), 176 (100). Elementary Analysis: $C_{27}H_{34}N_2O_4S$ Required: C, 67.19; H, 7.10; N, 5.80; S, 6.64. Found: C, 67.42; H, 7.21; N, 5.84; S, 6.49.

Example 47

Production of 6-(7-carboxybenzoxazol-2-ylthio)-N-(2,6-diisopropylphenyl)hexanamide In the same manner as in Example 26 except for the use of 6-(7-methoxycarbonylbenzoxazol-2-ylthio)-N-(2,6-diisopropylphenyl)hexanamide instead of 6-(4-methoxycarbonylbenzoxazol-2-ylthio)-N-(2,6-diisopropylphenyl) hexanamide, reaction progressed to recover the objective compound as a colorless crystal.

Melting Point: 175–177° C. IR (KBr) cm$^{-1}$: 3241, 2963, 1691, 1647, 1507. 1H-NMR (d$_6$-DMSO) δ: 1.12 (12H, d, J=6.9 Hz), 1.57 (2H, quint, J=7.3 Hz), 1.73 (2H, quint, J=7.3 Hz), 1.89 (2H, quint, J=7.3 Hz), 2.37 (2H, t, J=7.3 Hz), 3.08 (2H, sept, J=6.9 Hz), 3.38 (2H, t, J=7.3 Hz), 7.09 (2H, d, J=7.6 Hz), 7.20 (1H, t, J=7.6 Hz), 7.37 (1H, t, J=7.9 Hz), 7.76 (2H, d, J=7.9 Hz), 8.70 (1H, br s). Elementary Analysis: $C_{26}H_{32}N_2O_4S$ Required: C, 66.64; H, 6.88; N, 5.98; S, 6.84. Found: C, 66.48; H, 6.87; N, 6.06; S, 6.60.

Example 48

Production of 6-[7-hydroxymethylbenzoxazol-2-ylthio]-N-(2,6-diisopropylphenyl)hexanamide In the same manner as in Example 26 except for the use of 6-(7-carboxybenzoxazol-2-ylthio)-N-(2,6-diisopropylphenyl)hexanamide instead of 6-(4-carboxylbenzoxazol-2-ylthio)-N-(2,6-diisopropylphenyl) hexanamide, reaction progressed to recover the objective compound as a colorless crystal.

Melting Point: 91–92° C. IR (KBr) cm$^{-1}$: 3394, 2966, 1647, 1485, 1428. 1H-NMR (d$_6$-DMSO) δ: 1.12 (12H, d, J=6.9 Hz), 1.56 (2H, quint, J=7.3 Hz), 1.72 (2H, quint, J=7.3 Hz), 1.87 (2H, quint, J=7.3 Hz), 2.36 (2H, t, J=7.3 Hz), 3.08 (2H, sept, J=6.9 Hz), 3.36 (2H, t, J=7.3 Hz), 4.75 (2H, s), 4.88 (1H, br s), 7.09 (2H, d, J=7.6 Hz), 7.19 (1H, t, J=7.6 Hz), 7.26 (1H, t, J=7.3 Hz), 7.29 (1H, dd, J=7.3, 1.7 Hz), 7.46 (1H, dd, J=7.3, 1.7 Hz), 8.69 (1H, br s). Elementary Analysis: $C_{26}H_{34}N_2O_3S$ Required: C, 68.69; H, 7.54; N, 6.16; S, 7.05. Found: C, 68.54; H, 7.68; N, 6.26; S, 6.95.

Example 49

Production of 6-[7-(N,N-dimethylaminomethyl) benzoxazol-2-ylthio]-N-(2,6-diisopropylphenyl) hexanamide In the same manner as in Example 27 except for the use of 6-(7-hydroxymethylbenzoxazol-2-ylthio)-N-(2,6-diisopropylphenyl)hexanamide instead of 6-(4-hydroxymethylbenzoxazol-2-ylthio)-N-(2,6-diisopropylphenyl)hexanamide, reaction progressed to recover the objective compound as a colorless crystal.

Melting Point: 102–104° C. IR (KBr) cm$^{-1}$: 3426, 3234, 1646, 1530, 1501. 1H-NMR (d$_6$-DMSO) δ: 1.12 (12H, d, J=6.9 Hz), 1.56 (2H, quint, J=7.3 Hz), 1.72 (2H, quint, J=7.3 Hz), 1.87 (2H, quint, J=7.3 Hz), 2.24 (6H, s), 2.36 (2H, t, J=7.3 Hz), 3.08 (2H, sept, J=6.9 Hz), 3.35 (2H, t, J=7.3 Hz), 3.71 (2H, s), 7.09 (2H, d, J=7.6 Hz), 7.19 (1H, t, J=7.6 Hz), 7.23 (1H, dd, J=7.6, 1.3 Hz), 7.27 (1H, t, J=7.6 Hz), 7.48 (1H, dd, J=7.6, 1.3 Hz), 8.69 (1H, br s); Elementary Analysis: $C_{28}H_{39}N_3O_2S$ Required: C, 69.82; H, 8.16; N, 8.72; S, 6.65. Found: C, 69.88; H, 8.26; N, 8.65; S, 6.66.

Example 50

Production of 6-(7-N,N-dimethylaminobenzoxazol-2-ylthio)-N-(2,6-diisopropylphenyl )hexanamide To a solution of 6-(7-carboxybenzoxazol-2-ylthio)-N-(2,6-diisopropylphenyl)hexanamide (328 mg, 0.7 mmol) in t-BuOH (6 ml) were sequentially added triethylamine (101 mg, 1.0 mmol) and diphenylphosphoryl azide (248 mg, 0.9 mmol), at reflux under heating for 1.5 hours. After the resulting solution was left to stand for cooling, water was added to the solution, which was then adjusted to alkalinity with an aqueous potassium hydroxide solution, and extracted with ethyl acetate. The organic layer was washed sequentially with water and saturated sodium chloride solution, and was dried over anhydrous magnesium sulfate, from which the solvents were distilled off. The resulting residue was purified by silica gel column chromatography (10 g of silica gel; elution solvents; hexane:acetone=5:1), to recover 6-(7-t-butoxycarbonylaminobenzoxazol-2-ylthio)-N-(2,6-diisopropylphenyl)hexanamide (171 mg at a yield of 45%) as a colorless needle-like crystal.

The N-t-butoxycarbonylamino material (150 mg, 0.28 mmol) was dissolved in trifluoroacetic acid (2 ml), with stirring at ambient temperature for 2 hours. After distillation of trifluoroacetic acid, an aqueous sodium hydrogen carbonate solution was added to the resulting residue, and extracted with ethyl acetate. The organic layer was washed sequentially with water and saturated sodium chloride solution, and was dried over anhydrous magnesium sulfate, from which the solvents were distilled off. The resulting residue was purified by preparative thin layer chromatography (elution solvents; hexane:acetone=5:3), to recover 6-(7-aminobenzoxazol-2-ylthio)-N-(2,6-diisopropylphenyl)hexanamide (126 mg at a yield of 45%) as a pale brown needle-like crystal. To a solution of the aniline (180 mg, 0.41 mmol) in acetonitrile (3 ml) was added an aqueous 37% formaldehyde solution (123 mg, 4.1 mmol) under cooling in ice bath and was additionally added gradually sodium cyanoborohydride (100 mg, 1.6 mmol), followed by addition of acetic acid (0.05 ml). Ten minutes later, acetic acid (0.05 ml) was additionally added, with stirring for 20 minutes. To the reaction solution was added water, and extracted with ethyl acetate. The organic layer was sequentially washed with an aqueous sodium hydrogen carbonate solution and saturated sodium chloride solution and dried over anhydrous sodium sulfate, from which the solvents were distilled off. The residue was purified by silica gel column chromatography (12 g of silica gel; elution solvents:hexane:acetone=5:2), and the resulting crude crystal was recrystallized from acetone-hexane, to recover the objective compound (100 mg at a yield of 52%) as a colorless needle-like crystal.

Melting Point: 129–130° C. IR (KBr) cm$^{-1}$: 3435, 2965, 1645, 1537, 1497. 1H-NMR (d$_6$-DMSO) δ: 1.12 (12H, d, J=6.9 Hz), 1.56 (2H, quint, J=7.3 Hz), 1.71 (2H, quint, J=7.3 Hz), 1.87 (2H, quint, J=7.3 Hz), 2.36 (2H, t, J=7.3 Hz), 3.02 (6H, s), 3.08 (2H, sept, J=6.9 Hz), 3.33 (2H, t, J=7.3 Hz), 6.59 (1H, dd, J=8.0, 1.0 Hz), 6.95 (1H, dd, J=8.0, 1.0 Hz), 7.09 (2H, d, J=7.6 Hz), 7.12 (1H, t, J=8.0 Hz), 7.19 (1H, t, J=7.6 Hz), 8.69 (1H, br s). EIMS m/z (relative intensity): 467 (M$^+$), 193 (100). Elementary Analysis: C$_{27}$H$_{37}$N$_3$O$_2$S Required: C, 69.34; H, 7.97; N, 8.99; S, 6.86. Found: C, 69.37; H, 8.06; N, 8.87; S, 6.85.

Example 51

Production of 6-[7-(1-morpholino)methylbenzoxazol-2-ylthio]-N-(2,6-diisopropylphenyl)hexanamide To a solution of 6-(7-hydroxymethylbenzoxazol-2-ylthio)-N-(2,6-diisopropylphenyl)hexanamide (182 mg, 0.4 mmol) in dichloromethane (4 ml) were added triethylamine (61 m g , 0.6 mmol) and 4-dimethylaminopyridine (5 mg, 0.04 mmol), followed by dropwise addition of methane sulfonylchloride (57 mg, 0.5 mmol) under cooling in ice bath with stirring; the temperature was allowed to warm temperature; and then, the resulting solution was stirred for 15 minutes. The reaction solution was extracted with ethyl acetate; the organic layer was washed sequentially with 0.5 N hydrochloric acid and saturated sodium chloride solution, and was dried over anhydrous magnesium sulfate, from which the solvents were distilled off. Morpholine (139 mg, 1.6 mmol) was added to a solution of the resulting residue in THF (4 ml), at reflux under heating for one hour. The reaction solution was extracted with ethyl acetate; the organic layer was sequentially washed with an aqueous sodium hydrogen carbonate solution and saturated sodium chloride solution and dried over anhydrous sodium sulfate, from which the solvents were distilled off. The resulting crude crystal was recrystallized from acetone-ether-hexane, to recover the objective compound (170 mg at a yield of 81%) as a colorless needle-like crystal.

Melting Point: 117–118° C. IR (KBr) cm$^{-1}$: 3440, 2963, 1647, 1501, 1428. 1H-NMR (d$_6$-DMSO) δ: 1.12 (12H, d, J=6.8 Hz), 1.56 (2H, quint, J=7.3 Hz), 1.72 (2H, quint, J=7.3 Hz), 1.87 (2H, quint, J=7.3 Hz), 2.36 (2H, t, J=7.3 Hz), 2.42–2.45 (4H, m), 3.08 (2H, sept, J=6.9 Hz), 3.35 (2H, t, J=7.3 Hz), 3.56–3.59 (4H, m), 3.74 (2H, s), 7.09 (2H, d, J=7.6 Hz), 7.19 (1H, t, J=7.6 Hz), 7.24 (1H, dd, J=7.6, 1.9 Hz), 7.27 (1H, t, J=7.6 Hz), 7.48 (1H, dd, J=7.6, 1.9 Hz), 8.70 (1H, br s). Elementary Analysis: C$_{30}$H$_{41}$N$_3$O$_3$S Required: C, 68.80; H, 7.89; N, 8.02; S, 6.12. Found: C, 68.72; H, 7.91; N, 7.92; S, 6.23.

Example 52

Production of 6-[7-(tetrazol-5-yl)benzoxazol-2-ylthio)-N-(2,6-diisopropylphenyl)hexanamide To a solution of 6-(7-carboxybenzoxazol-2-ylthio)-N-(2,6-diisopropylphenyl)hexanamide (469 mg, 1.0 mmol) and 1-hydroxybenzotriazole ammonium salt (167 mg, 1.1 mmol) in DMF (8 ml) was added WSC (211 mg, 1.1 mmol), and the resulting mixture was stirred at ambient temperature for 15 hours. After the reaction solution was extracted with ethyl acetate, the organic layer was washed sequentially with diluted hydrochloric acid, water and saturated sodium chloride solution, and was dried over anhydrous sodium sulfate, from which the solvents were distilled off. The residue was purified by silica gel column chromatography (30 g of silica gel; elution solvents:chloroform:methanol=5:2), to recover 6-(7-carbamoylbenzoxazol-2-ylthio)-N-(2,6-diisopropylphenyl)hexanamide (493 mg at a yield of 100%). The amide material (493 mg, 1.0 mmol) was dissolved in phosphorus oxychloride (3 ml), with stirring at ambient temperature for 24 hours. The reaction solution was poured into ice water, to decompose excess phosphorus oxychloride; the resulting solution was neutralized with an aqueous potassium hydroxide solution, and extracted with ethyl acetate. The organic layer was washed sequentially with water and saturated sodium chloride solution, and was dried over anhydrous sodium sulfate, from which the solvents were distilled off. The resulting crude crystal was recrystallized from acetone-ether-hexane, to recover 6-(7-cyanobenzoxazol-2-ylthio)-N-(2,6-diisopropylphenyl)hexanamide (315 mg at a yield of 70%). To a solution of the nitrile material (300 mg, 0.67 mmol) in DMF (3 ml) were added sodium azide (173.5 mg, 2.67 mmol) and ammonium chloride (142.8 mg, 2.67 mmol), with stirring at 120° C. for 15 hours. To the resulting reaction solution was added 1 N hydrochloric acid, and resulting mixture was extracted with ethyl acetate. The organic layer was washed with water and saturated sodium chloride solution and dried over anhydrous sodium sulfate, from which the solvents were distilled off.

The resulting residue was purified by silica gel column chromatography (20 g of silica gel; elution solvents:chloroform:acetone:acetic acid=60:4:1). The resulting crystal was recrystallized from acetone-ether-hexane, to recover the objective compound (115 mg at a yield of 35%) as a colorless crystal.

Melting Point: 218–220° C. IR (KBr) cm$^{-1}$: 3425, 2963, 1647, 1501, 1444. 1H-NMR (d$_6$-DMSO) δ: 1.11 (12H, d, J=6.8 Hz), 1.58 (2H, quint, J=7.3 Hz), 1.73 (2H, quint, J=7.3 Hz), 1.92 (2H, quint, J=7.3 Hz), 2.37 (2H, t, J=7.3 Hz), 3.08 (2H, sept, J=6.8 Hz), 3.42 (2H, t, J=7.3 Hz), 7.09 (2H, d, J=7.6 Hz), 7.19 (1H, t, J=7.6 Hz), 7.50 (1H, t, J=7.8 Hz), 7.78 (1H, dd, J=7.8, 1.0 Hz), 7.89 (1H, dd, J=7.8, 1.0 Hz), 8.70 (1H, br s). Elementary Analysis: C$_{26}$H$_{32}$N$_6$O$_2$S Required: C, 63.39; H, 6.55; N, 17.06; S, 6.51. Found: C, 63.60; H, 6.63; N, 16.85; S, 6.45.

Example 53

Production of 2-(7-methoxycarbonylbenzoxazol-2-ylthio)-N-(2,6-diisopropylphenyl)acetamide In the same manner as in Example 46 except for the use of 2-bromo-N-(2,6-diisopropylphenyl)acetamide instead of 6-bromo-N-(2,6-diisopropylphenyl)hexanamide, reaction progressed to recover the objective compound as a colorless crystal.

Melting Point: 186–187° C. IR (KBr) cm$^{-1}$: 3437, 2965, 1733, 1637, 1367. 1H-NMR (d$_6$-DMSO) δ: 1.17 (6H, d, J=6.8 Hz), 1.25 (6H, d, J=6.8 Hz), 2.90 (2H, sept, J=6.8 Hz), 3.92 (3H, s), 4.27 (2H, s), 6.89 (1H, t, J=7.8 Hz), 6.95 (1H, dd, J=7.8, 1.8 Hz), 7.28 (2H, d, J=7.8 Hz), 7.42 (1H, t, J=7.8 Hz), 7.56 (1H, dd, J=7.8, 1.7 Hz), 10.29 (1H, s). Elementary Analysis: C$_{23}$H$_{26}$N$_2$O$_4$S Required: C, 64.77; H, 6.14; N, 6.57; S, 7.52. Found: C, 64.92; H, 6.19; N, 6.65; S, 7.55.

Example 54

Production of 9-(6-methoxycarbonylbenzoxazol-2-ylthio)-N-(2,6-diisopropylphenyl)nonanamide In the same manner as in Example 46 except for the use of 9-bromo-N-(2,6-diisopropylphenyl)nonanamide instead of 6-bromo-N-(2,6-diisopropylphenyl)hexanamide, reaction progressed to recover the objective compound as a colorless needle-like crystal.

Melting Point: 122–124° C. IR (KBr) cm$^{-1}$: 3428, 3242, 2968, 1724, 1649. 1H-NMR (d$_6$-DMSO) δ: 1.12 (12H, d, J=6.8 Hz), 1.34–1.68 (10H, m), 1.85 (2H, quint, J=7.1 Hz), 2.32 (2H, m), 3.09 (2H, sept, J=6.8 Hz), 3.36 (2H, t, J=7.2 Hz), 3.93 (3H, s), 7.08 (1H, d, J=8.3 Hz), 7.09 (1H, d, J=6.6 Hz), 7.19 (1H, dd, J=8.3, 6.6 Hz), 7.40 (1H, t, J=7.8 Hz), 7.79 (1H, dd, J=7.8, 1.2 Hz), 7.81 (1H, dd, J=7.8, 1.2 Hz), 8.62 (1H, br s). Elementary Analysis: C$_{30}$H$_{40}$N$_2$O$_4$S Required: C, 68.67; H, 7.68; N, 5.34; S, 6.11. Found: C, 68.78; H, 7.66; N, 5.41; S, 6.07.

Example 55

Production of N-(2,6-diisopropylphenyl)-N'-[7-(7-methoxycarbonylbenzoxazol-2-ylthio)heptyl]urea To a solution of 7-methoxycarbonyl-2-mercaptobenzoxazole (100 mg, 0.48 mmol) and N-(2,6-diisopropylphenyl)-N'-(7-bromoheptyl)urea (190 mg, 0.48mmol) in DMF (5 ml) were added potassium carbonate (73 mg, 0.53 mmol) and 18-crown-6 (13 mg, 0.05 mmol), with stirring at 80° C. for 4 hours. The reaction solution was diluted with water, and extracted with ethyl acetate. The organic layer was sequentially washed with water and saturated sodium chloride and dried over anhydrous magnesium sulfate, from which the solvents were distilled off. The resulting crystal was recrystallized from chloroform-ethyl acetate-hexane, to recover the objective compound (184 mg at a yield of 73%) as a colorless crystal.

Melting Point: 179–181° C. IR (KBr) cm$^{-1}$: 3319, 2931, 1722, 1625, 1509. 1H-NMR (d$_6$-DMSO) δ: 1.05 (12H, d, J=6.8 Hz), 1.25–1.42 (8H, m), 1.76 (2H, quint, J=7.3 Hz), 3.00 (2H, dt, J=6.6, 6.1 Hz), 3.11 (2H, sept, J=6.8 Hz), 3.29 (2H, t, J=7.3 Hz), 3.86 (3H, s), 5.48 (1H, br s), 6.93 (1H, br s), 7.00 (2H, d, J=7.6 Hz), 7.09 (1H, t, 7.6 Hz), 7.35 (1H, t, J=7.8 Hz), 7.75 (1H, dd, J=7.8, 1.2 Hz), 7.76 (1H, dd, J=7.6, 1.2 Hz). Elementary Analysis: C$_{29}$H$_{39}$N$_3$O$_4$S Required: C, 66.26; H, 7.48; N, 7.99; S, 6.10. Found: C, 65.99; H, 7.51; N, 8.20; S, 5.94.

Example 56

Production of N-(2,6-diisopropylphenyl)-N'-[7-(7-methoxycarbonylbenzoxazol-2-ylsulfinyl)heptyl]urea To a solution in dichloromethane-methanol (2:1, 9 ml) of the N-(2,6-diisopropylphenyl)-N'-[7-(7-methoxycarbonylbenzoxazol-2-ylthio)heptyl]urea (100 mg, 0.19 mmol) recovered in Example 55 was added m-chloroperbenzoic acid (60 mg, 0.19 mmol) at 0° C., with stirring at ambient temperature for 14 hours. The reaction solution was diluted with an aqueous sodium hydrogen carbonate solution, and extracted with ethyl acetate. The organic layer was washed with water and dried over anhydrous magnesium sulfate, from which the solvents were distilled off. The resulting residue was purified by preparative thin layer chromatography (elution solvents; chloroform:acetone:methanol=75:25:1); the resulting crystal was recrystallized from chloroform-ethyl acetate-hexane, to recover the objective compound (66 mg at a yield of 64%) as a colorless crystal.

Melting Point: 145–147° C. IR (KBr) cm$^{-1}$: 3319, 2931, 1727, 1626, 1295. 1H-NMR (d$_6$-DMSO) δ: 1.14 (12H, d, J=6.8 Hz), 1.28–1.38 (4H, m), 1.38–1.51 (4H, m), 1.70–1.90 (2H, m), 3.06 (2H, dd, J=6.6, 6.1 Hz), 3.19 (2H, sept, J=6.8 Hz), 3.38–3.52 (2H, m), 3.98 (3H, s), 5.57 (1H, br s), 7.01 (1H, br s), 7.09 (2H, d, J=7.3 Hz), 7.18 (1H, t, J=7.3 Hz), 7.62 (1H, t, J=7.9 Hz), 8.06 (1H, dd, J=7.9, 1.2 Hz), 8.14 (1H, dd, J=7.9, 1.2 Hz). Elementary Analysis: C$_{29}$H$_{39}$N$_3$O$_5$S Required: C, 64.30; H, 7.26; N, 7.76; S, 5.92. Found: C, 64.08; H, 7.53; N, 7.64; S, 5.94.

Example 57

Production of N-(2,6-diisopropylphenyl)-N'-[7-(5-N,N-dimethylaminobenzoxazol-2-ylthio)heptyl]urea To a solution of 2-mercapto-5-nitrobenzoxazole (200 mg, 1.02 mmol) and N-(7-bromoheptyl)-N'-(2,6-diisopropylphenyl)urea (484 mg, 1.02 mmol) in DMF (5 ml) were added potassium carbonate (185 mg, 1.34 mmol) and 18-crown-6 (32 mg, 0.10 mmol),with stirring at 80° C. for 4 hours. The reaction solution was diluted with water, and extracted with ethyl acetate. The organic layer was sequentially washed with water and saturated sodium chloride solution and dried over anhydrous magnesium sulfate, from which the solvents were distilled off. The resulting crystal was recrystallized from chloroform-ethyl acetate-hexane, to recover N-(2,6-diisopropylphenyl)-N'-[7-(5-nitrobenzoxazol-2-ylthio)heptyl]urea (500 mg at a yield of 96%) as a pale yellow crystal (at a melting point of 134–135° C.).

The nitro material (387 mg, 0.76 mmol) was dissolved in acetic acid (8 ml), followed by addition of zinc (987 mg, 15.1 mmol) under cooling in ice bath, and the resulting mixture was stirred at ambient temperature for 15 minutes. After the reaction solution was diluted with ethyl acetate and filtered through celite, the filtrate was adjusted to neutrality by using an aqueous sodium hydrogen carbonate solution. The organic layer was washed sequentially with an aqueous sodium hydrogen carbonate solution, water and saturated sodium chloride solution, and was dried over anhydrous magnesium sulfate, from which the solvents were distilled off. The residue was purified by silica gel column chromatography (hexane:acetone=2:1); the resulting crystal was recrystallized from chloroform-ethyl acetate-ether, to recover N-(2,6-diisopropylphenyl)-N'-[7-(5-aminobenzoxazol-2-ylthio)heptyl]urea (320 mg at a yield of 88%) as a pale yellow powdery crystal. To a solution of the amine (160 mg, 0.33 mmol) in acetonitrile (3 ml) were sequentially added a solution of an aqueous 37% formaldehyde solution (269 mg, 3.32 mmol) in acetonitrile (1 ml) and a suspension of sodium cyanoborohydride (83 mg, 1.33 mmol) in acetonitrile (1 ml), followed by dropwise addition of acetic acid (27 μl) with stirring at ambient temperature; and then, the resulting mixture was further stirred for 30 minutes. After distillation of the solvents, the resulting residue was diluted with water, and extracted with ethyl acetate. The organic layer was sequentially washed with water and saturated sodium chloride solution and dried over anhydrous sodium sulfate, from which the solvents were distilled off. The residue was purified by preparative thin layer chromatography (elution solvents:hexane:acetone= 2:1), and the resulting crystal was recrystallized from acetone-hexane, to recover the objective compound (67 mg at a yield of 40%) as a colorless crystal.

Melting Point: 139–140° C. IR (KBr) cm$^{-1}$: 3321, 2929, 1629, 1571, 1149. 1H-NMR (d$_6$-DMSO) δ: 1.06 (12H, d, J=6.8 Hz), 1.21–1.31 (4H, m), 1.33–1.43 (4H, m), 1.71 (2H, quint, J=7.3 Hz), 2.83 (6H, s), 3.00 (2H, dt, J=6.6, 6.1 Hz), 3.11 (2H, sept, J=6.8 Hz), 3.21 (2H, t, J=7.3Hz), 5.49 (1H, br s), 6.65 (1H, dd, J=9.0, 2.7 Hz), 6.81 (1H, d, J=2.7 Hz), 6.93 (1H, br s), 7.00 (2H, d, J=8.1 Hz), 7.10 (1H, dd, J=8.1, 6.8 Hz), 7.27 (1H, d, J=9.0 Hz). Elementary Analysis: C$_{29}$H$_{42}$N$_4$O$_2$S Required: C, 68.20; H, 8.29; N, 10.97; S, 6.28. Found: C, 68.19; H, 8.27; N, 10.73; S, 6.13.

Example 58

Production of 6-(7-methoxycarbonylbenzoxazol-2-ylthiosulfonyl)-N-(2,6-diisopropylphenyl)hexanamide To a solution of 6-(7-methoxycarbonylbenzoxazol-2-ylthio)-N-(2,6-diisopropylphenyl)hexanamide (37 mg, 0.08 mmol) in methylene chloride (3 ml) was added m-chloroperbenzoic acid (48 mg, 0.15 mmol) at –20° C., with stirring at ambient temperature for 19 hours. The reaction solution was diluted with an aqueous sodium hydrogen carbonate solution, and extracted with ethyl acetate. The organic layer was washed with water and dried over anhydrous magnesium sulfate, from which the solvents were distilled off. The resulting residue was purified by preparative thin layer chromatography (elution solvents; chloroform:acetone=4:1); and the resulting crystal was recrystallized from ethyl acetate-hexane, to recover the objective compound (15 mg at a yield of 38%) as a colorless needle-like crystal.

Melting Point: 145–147° C. IR (KBr) cm$^{-1}$: 3235, 2961, 1732, 1652, 1345, 1159. 1H-NMR (d$_6$-DMSO) δ: 1.13 (12H, d, J=7.0 Hz), 1.54–1.63 (2H, m), 1.66–1.75 (2H, m), 1.90–1.99 (2H, m), 2.31–2.39 (2H, m), 3.08 (2H, sept, J=7.0 Hz), 3.76 (2H, t, J=7.6 Hz), 3.99 (3H, s), 7.11 (2H, d, J=7.7 Hz), 7.21 (1H, t, J=7.7 Hz), 7.70 (1H, t, J=8.1 Hz), 8.17 (1H, dd, J=7.6, 1.2 Hz), 8.23 (1H, dd, J=8.1, 1.2 Hz), 8.72 (1H, br s). Elementary Analysis: C$_{27}$H$_{34}$N$_2$O$_6$S.1/6H$_2$O Required: C, 62.65; H, 6.69; N, 5.41; S, 5.92. Found: C, 62.68; H, 6.67; N, 5.47; S, 5.94.

Example 59

Production of 6-[7-(2-N,N-dimethylaminoethyloxycarbonyl)benzoxazol-2-ylthio]-N-(2,6-diisopropylphenyl)hexanamide A solution of 2,4,6-trichlorobenzoyl chloride (104 mg, 0.425 mmol) in THF (2 ml) was dropwise added to a solution of 6-(7-carboxybenzoxazol-2-ylthio)-N-(2,6-diisopropylphenyl)hexanamide (199 mg, 0.425 mmol) and tritylamine (52 mg, 0.510 mmol) in THF (1 ml) under cooling in ice bath. After stirring at ambient temperature for 35 minutes, the deposited triethylamine hydrochloride salt was filtered off. From the filtrate was distilled off the solvents under reduced pressure, and a solution of the resulting residue in chloroform (2 ml) was dropwise added to a solution of N,N-dimethyl ethanolamine (38 mg, 0.425 mmol), and dimethylaminopyridine (5 mg, 0.043 mmol) in chloroform (1 ml) under cooling in ice bath, with stirring at ambient temperature for 40 minutes. After distillation of the solvents from the resulting reaction solution under reduced pressure, the resulting residue was diluted with ethyl acetate and water. The organic layer was washed sequentially with saturated sodium hydrogen carbonate solution, water and saturated sodium chloride solution and dried over anhydrous sodium sulfate, from which the solvents were distilled off. The resulting residue was purified by silica gel column chromatography (20 g of silica gel; elution solvents:hexane:acetone=5:2/chloroform:methanol=100:1-20:1-10:1); and the resulting crystal was recrystallized from acetone-hexane, to recover the objective compound (114 mg at a yield of 50%) as a colorless needle-like crystal.

Melting Point: 119–120° C. IR (KBr) cm$^{-1}$: 3423, 3232, 2966, 1721, 1647. 1H-NMR (d$_6$-DMSO) δ: 1.13 (12H, d, J=6.8 Hz), 1.53–1.96 (6H, m), 2.28 (6H,s), 2.37 (2H,m), 2.71 (2H, t, J=5.9 Hz), 3.09 (2H, sept, J=6.8 Hz), 3.39 (2H, t, J=7.2 Hz), 4.43 (2H, t, J=5.9 Hz), 7.08 (1H, d, J=8.5 Hz), 7.09 (1H, d, J=6.7 Hz), 7.19 (1H, dd, J=8.5, 6.7 Hz), 7.40 (1H, t, J=7.8 Hz), 7.80 (2H, dd, J=7.8, 1.5 Hz), 8.64 (1H, br s). Elementary Analysis: C$_{30}$H$_{41}$N$_3$O$_4$S Required: C, 66.76; H, 7.66; N, 7.79; S, 5.94. Found: C, 66.75; H, 7.73; N, 7.80; S, 5.91.

Example 60

Production of 6-[7-(2-N,N-dimethylaminoethyloxycarbamoyl)benzoxazol-2-ylthio]-N-(2,6-diisopropylphenyl)hexanamide A solution of 2,4,6-trichlorobenzoyl chloride (104 mg, 0.425 mmol) in THF (2 ml) was dropwise added to a solution of 6-(7-carboxybenzoxazol-2-ylthio)-N-(2,6-diisopropylphenyl)hexanamide (199 mg, 0.425 mmol) and triethylamine (52 mg, 0.510 mmol) in THF (1 ml) under cooling in ice bath. After stirring at ambient temperature for 35 minutes, the deposited triethylamine hydrochloride salt was filtered off. From the filtrate was distilled off the solvents under reduced pressure, and a solution of the resulting residue in chloroform (2 ml) was dropwise added to a solution of N,N-dimethylethylenediamine (44 mg, 0.5 mmol) and dimethylaminopyridine (6 mg, 0.005 mmol) in chloroform (1 ml) under cooling in ice bath, with stirring at ambient temperature for one hour. After distillation of the solvents under reduced pressure from the resulting reaction solution, the resulting residue was diluted with ethyl acetate and water. The organic layer was washed sequentially with saturated sodium hydrogen carbonate solution, water and saturated sodium chloride solution and dried over anhydrous sodium sulfate, from which the solvents were distilled off. The resulting residue was purified by silica gel column chromatography (20 g of silica gel; elution solvents:chloroform:saturated ammonia-methanol=20:1); and the resulting crystal was recrystallized from acetone-hexane, to recover the objective compound (60 mg at a yield of 22%) as a colorless crystal.

Melting Point: 135–137° C. IR (KBr) cm$^{-1}$: 3401, 3255, 2963, 1669, 1648. 1H-NMR (d$_6$-DMSO) δ: 1.12 (12H, d, J=6.8 Hz), 1.52–1.94 (6H, m), 2.26 (6H, s), 2.37 (2H, m), 2.52 (2H, t, J=6.4 Hz), 3.09 (2H, sept, J=6.8 Hz), 3.40 (2H, t, J=7.1 Hz), 3.46 (2H, q, J=6.4 Hz), 7.09 (1H, d, J=8.3 Hz), 7.09 (1H, d, J=6.6 Hz), 7.19 (1H,dd, J=8.3, 6.6 Hz), 7.36 (1H, t, J=7.8 Hz), 7.67 (1H, dd, J=7.8, 1.2 Hz), 7.69 (1H, dd, J=7.8, 1.2 Hz), 7.74 (1H, br s). 8.66 (1H, br s) Elementary Analysis: $C_{30}H_{42}N_4O_3S$ Required: C, 66.88; H, 7.86; N, 10.40; S, 6.84. Found: C, 66.71; H, 7.82; N, 10.25; S, 6.67.

Example 61

Production of 2-(7-methoxylcarbonylbenzoxazol-2-ylthio)-N-(2,4,6-trifluorophenyl)acetamide In the same manner as in Example 46 except for the use of 2-bromo-N-(2,4,6-trichlorophenyl)acetamide instead of 6-bromo-N-(2,6-diisopropylphenyl)hexanamide, reaction progressed to recover the objective compound as a colorless needle-like crystal.

Melting Point: 190–192° C. IR (KBr) cm$^{-1}$: 3426, 3252, 1723, 1679, 1508. 1H-NMR (CDCl$_3$) δ: 3.99 (3H, s), 4.08 (2H, s), 6.70 (2H, m), 7.41 (1H, t, J=7.8 Hz), 7.81 (1H, dd, J=7.8, 1.0 Hz), 7.94 (1H, dd, J=7.8, 1.0 Hz), 9.03 (1H, br s). Elementary Analysis: $C_{23}H_{26}N_2O_4S$ Required: C, 51.52; H, 2.80; N, 7.07; S, 14.38. Found: C, 51.44; H, 2.92; N, 7.03; S, 14.28.

Example 62

Production of 6-(7-methoxylcarbonylbenzoxazol-2-ylthio)-N-(2,4,6-trimethoxyphenyl)hexanamide To a solution of 2,4,6-trimethoxyaniline (180 mg, 0.98 mmol) and triethylamine (111 mg, 1.1 mmol) in chloroform (4 ml) was dropwise added 6-bromohexanoyl chloride (214 mg, 1.0 mmol) under cooling in ice bath, with stirring at ambient temperature for one hour. The reaction mixture was concentrated, and the resulting residue was extracted with ethyl acetate. The organic layer was washed with dilute hydrochloric acid, an aqueous sodium hydrogen carbonate solution, water, and saturated sodium chloride solution and dried over anhydrous sodium sulfate, from which the solvents were distilled off; the resulting crystal was recrystallized from hexane-ether-chloroform, to recover the objective compound (320 mg at a yield of 89%) as a colorless needle-like crystal. In the same manner as in Example 46 except for the use of 6-bromo-N-(2,4,6-trimethoxyphenyl) hexanamide instead of 6-bromo-N-(2,6-diisopropylphenyl) hexanamide, subsequently, reaction progressed to recover the objective compound as a colorless needle-like crystal.

Melting Point: 136–138° C. IR (KBr) cm$^{-1}$: 3251, 2935, 1727, 1660, 1507. 1H-NMR (d$_6$-DMSO) δ: 1.52 (2H, quint, J=7.3 Hz), 1.64 (2H, quint, J=7.3 Hz), 1.85 (2H, quint, J=7.3 Hz), 2.19 (2H, t, J=7.3 Hz), 3.36 (2H, t, J=7.3 Hz), 3.71 (6H, s), 3.76 (3H, S), 3.93 (3H, s), 6.22 (2H, s), 7.42 (1H, t, J=7.8 Hz), 7.80 (1H, dd, J=7.8, 1.2 Hz),7.84 (1H, dd, J=7.8, 1.2 Hz), 7.92 (1H, br S). Elementary Analysis: $C_{24}H_{28}N_2O_7S$ Required: C, 59.00; H, 5.78; N, 5.73; S, 6.56. Found: c, 58.94; H, 5.82; N, 5.74; S, 6.55

Example 63

Production of 6-(5-methoxycarbonylbenzimidazol-2-ylthio)-N-(2,6-diisopropylphenyl)hexanamide To a solution of 5-methoxycarbonyl-2-mercaptobenzimidazole (100 mg, 0.48 mmol) and 6-bromo-N-(2,6-diisopropylphenyl)hexanamide (170 mg, 0.48 mmol) in DMF (4 ml) were added potassium carbonate (73 mg, 0.53 mmol) and 18-crown-6 (13mg, 0.05 mmol),with stirring at 80° C. for 4 hours. The reaction solution was diluted with water, and extracted with ethyl acetate. The organic layer was sequentially washed with water and saturated sodium chloride solution and dried over anhydrous magnesium sulfate, from which the solvents were distilled off. The resulting crystal was purified by preparative thin layer chromatography (elution solvents:chloroform:acetone saturated ammonia methanol=80:20:1); and the resulting crystal was recrystallized from ethyl acetate-hexane, to recover the objective compound (137 mg at a yield of 59%) as a colorless crystal.

Melting Point: 190–192° C. IR (KBr) cm$^{-1}$: 3178, 2962, 1716, 1655, 1434, 1297. 1H-NMR (d$_6$-DMSO) δ: 1.13 (12H, d, J=6.8 Hz), 1.51–1.62 (2H, m), 1.68–1.77 (2H, m), 1.77–1.87 (2H, m), 2.33–2.41 (2H, m), 3.10 (2H, sept, J=6.8 Hz), 3.35 (2H, t, J=7.2 Hz), 3.87 (3H, s), 7.10 (1H, d, J=8.1 Hz), 7.11 (1H, d, J=7.3 Hz), 7.21 (1H, dd, J=8.1, 7.3 Hz), 7.47 (1H, d, J=8.3 Hz), 7.77 (1H, dd, J=8.3, 1.6 Hz), 8.03 (1H, br s), 8.71 (1H, br s). Elementary Analysis: $C_{27}H_{35}N_3O_3S \cdot 0.4H_2O$ Required: C, 66.34; H, 7.38; N, 8.60; S, 6.56. Found: C, 66.25; H, 7.37; N, 8.42; S, 6.40.

Example 64

Production of 6-(5-N,N-dimethylaminobenzimidazol-2-ylthio)-N-(2,6-diisopropylphenyl)hexanamide To a solution of 2-mercapto-5-nitrobenzimidazole (195 mg, 1.0 mmol) and 6-bromo-N-(2,6-diisopropylphenyl) hexanamide (354 mg, 1.0 mmol) in DMF (7 ml) were added potassium carbonate (152 mg, 1.1 mmol) and 18-crown-6 (26 mg, 0.1 mmol),with stirring at 80° C. for 3 hours. The reaction solution was diluted with water, and extracted with ethyl acetate. The organic layer was sequentially washed with water and saturated sodium chloride solution and dried over anhydrous magnesium sulfate, from which the solvents were distilled off, to recover 6-(5-nitrobenzimidazol-2-ylthio)-N-(2,6-diisopropylphenyl)hexanamide (600 mg) as a pale yellow oil. The nitro material (640 mg, 1.37 mmol) was dissolved in acetic acid (10 ml), followed by addition of zinc (1.79 g, 27.3 mmol) under cooling in ice bath, with stirring at ambient temperature for 15 minutes. The reaction solution was filtered through celite; the resulting filtrate was adjusted to neutrality by using an aqueous sodium hydrogen carbonate solution, and extracted with ethyl acetate. The organic layer was washed sequentially with an aqueous sodium hydrogen carbonate solution, water and saturated sodium chloride solution and dried over anhydrous sodium sulfate solution, from which the solvents were distilled off. The residue was purified by silica gel column chromatography (elution solvents; chloroform:methanol=10:1), to recover 6-(5-aminobenzimidazol-2-ylthio)-N-(2,6-diisopropylphenyl)hexanamide (451 mg at a yield of 75%) as a pale yellow oil.

To a solution of the aniline (398 mg, 0.91 mmol) in acetonitrile (7 ml) were added sequentially an aqueous 37% formaldehyde solution (736 mg, 9.07 mmol) and a suspension of sodium cyanoborohydride (228 mg, 3.63 mmol) in acetonitrile (7 ml), followed by dropwise addition of acetic acid (73 µl) while the resulting mixture was stirred at ambient temperature; and then, the resulting mixture was further stirred for 30 minutes. After distillation of the solvents, the resulting residue was diluted with water, and extracted with ethyl acetate. The organic layer was sequentially washed with water and saturated sodium chloride solution and dried over anhydrous sodium sulfate, from which the solvents were distilled off. The residue was purified by preparative thin layer chromatography (elution solvents:chloroform:saturated ammonia methanol=10:1), and the resulting crystal was recrystallized from chloroform-ethyl acetate-hexane, to recover the objective compound (53 mg at a yield of 13%) as a pale brown powdery crystal.

Melting Point: 109–111° C. IR (KBr) cm$^{-1}$: 3235, 2962, 1651, 1519, 1440. 1H-NMR (d$_6$-DMSO) δ: 1.13 (12H, d, J=6.8 Hz), 1.51–1.59 (2H, m), 1.66–1.82 (4H, m), 2.32–2.40 (2H, m), 2.89 (6H, s), 3.10 (2H, sept, J=6.8 Hz), 3.24 (2H, t, J=7.1 Hz), 6.68–6.76 (2H, m), 7.11 (2H, d, J=7.6 Hz), 7.18–7.28 (2H, m), 8.71 (1H, br s). Elementary Analysis: C$_{27}$H$_{38}$N$_4$OS Required: C, 69.49; H, 8.21; N, 12.01; S, 6.87. Found: C, 69.31; H, 8.20; N, 11.90;. S, 6.91.

Example 65

Production of 6-(6-N,N-dimethylaminobenzothiazol-2-ylthio)-N-(2,6-diisopropylphenyl)hexanamide To a solution of 2-mercapto-6-nitrobenzothiazole (212 mg, 1.0 mmol) and 6-bromo-N-(2,6-diisopropylphenyl)hexanamide (354 mg, 1.0 mmol) in DMF (6 ml) were added potassium carbonate (152 mg, 1.1 mmol) and 18-crown-6 (26 mg, 0.1 mmol),with stirring at 80° C. for 2 hours. The reaction solution was diluted with water and ethyl acetate. The organic layer was sequentially washed with an aqueous sodium hydrogen carbonate solution, water, dilute hydrochloric acid and saturated sodium chloride solution and dried over anhydrous magnesium sulfate, from which the solvents were distilled off. The residue was purified by silica gel column chromatography (50 g of silica gel; elution solvents:hexane:acetone=5:2), to recover 6-(6-nitrobenzothiazol-2-ylthio)-N-(2,6-diisopropylphenyl) hexanamide (490 mg at a yield of 100%) as a pale yellow oil. The nitro material (490 mg, 1.0 mmol) was dissolved in acetic acid (5 ml), followed by addition of zinc (1.3 g, 20 mmol) under cooling in ice bath, with stirring at ambient temperature for 20 minutes. The reaction solution was diluted with ethyl acetate and filtered through celite; the filtrate was adjusted to neutrality by using an aqueous sodium hydrogen carbonate solution. The organic layer was sequentially washed with an aqueous sodium hydrogen carbonate solution, water and saturated sodium chloride solution and dried over anhydrous sodium sulfate, from which the solvents were distilled off, to recover 6-(6-aminobenzothiazol-2-ylthio)-N-(2,6-diisopropylphenyl) hexanamide (426 mg). To a solution of the amine material (380 mg, 0.83 mmol) in acetonitrile (4 ml) were added sequentially an aqueous 37% formaldehyde solution (325 mg, 4.0 mmol) and sodium cyanoborohydride (100.5 mg, 1.6 mmol), followed by dropwise addition of acetic acid (0.1 ml) while the resulting mixture was stirred at ambient temperature; and then, the resulting mixture was further stirred for 2 hours as it was. Additionally, acetic acid (0.1 ml) was dropwise added to the mixture, which was stirred for 30 minutes. After distillation of the solvents under reduced pressure, the resulting residue was diluted with ethyl acetate and water. The organic layer was sequentially washed with an aqueous sodium hydrogen carbonate solution, water and saturated sodium chloride solution and dried over anhydrous magnesium sulfate, from which the solvents were distilled off. The residue was purified by silica gel column chromatography (elution solvents:hexane:acetone=10:1 to 5:1), and the resulting crystal was recrystallized from acetone-dichloromethane-hexane, to recover the objective compound (152 mg at a yield of 38%) as a colorless needle-like crystal.

Melting Point: 146–147° C. IR (KBr) cm$^{-1}$: 3427, 3233, 1648, 1602, 1460. 1H-NMR (d$_6$-DMSO) δ: 1.12 (12H, d, J=6.8 Hz), 1.50–1.60 (6H, m), 1.68–1.75 (2H, m), 1.78–1.85 (2H, m), 2.35 (2H, t, J=6.8 Hz), 2.94 (6H, s), 3.08 (2H, sept, J=6.8 Hz), 3.29 (2H, t, J=7.3 Hz), 6.90 (1H, dd, J=9.0, 2.6 Hz), 7.09 (1H, d, J=7.6 Hz), 7.17 (1H, d, J=2.6 Hz), 7.20 (1H, t, J=7.6 Hz), 7.62 (1H, d, J=9.0 Hz), 8.70 (1H, br s). Elementary Analysis: C$_{27}$H$_{37}$N$_3$OS$_2$ Required: C, 67.04; H, 7.71; N, 8.69; S, 13.26. Found: C, 67.00; H, 7.83; N, 8.70; S, 13.19.

Example 66

Production of 6-[(±)-3a, 7a-trans-3a,4,5,6,7,7a-hexahydrobenzoxazol-2-ylthio]-N-(2,6-diisopropylphenyl)hexanamide A mixture solution of (±)-trans-2-aminocyclohexanol (500 mg, 4.34 mmol), carbon disulfide (1 ml) and an aqueous 0.5 N sodium hydroxide solution (1 ml) was refluxed under heating for 4 hours. The reaction solution was extracted with ether and then isolated; to the aqueous layer was added acetic acid to adjust the layer to acidity, and the resulting mixture was extracted with ether. The organic layer was washed with water and dried over anhydrous magnesium sulfate, from which the solvents were distilled off.

To a solution of the resulting (±)-2-mercapto-3a,7a-trans-3a,4,5,6,7,7a-hexahydrobenzoxazole (67 mg, 0.43 mmol) and 6-bromo-N-(2,6-diisopropylphenyl)hexanamide (151 mg, 0.43 mmol) in DMF (3 ml) were added potassium carbonate (65 mg, 0.47 mmol) and 18-crown-6 (11 mg, 0.04 mmol), with stirring at 80° C. for 6 hours. The reaction solution was diluted with water, and extracted with ethyl acetate. The organic layer was washed with water and dried over anhydrous magnesium sulfate, from which the solvents were distilled off. The residue was purified by preparative thin layer chromatography (elution solvents:hexane:acetone=3:1); and the resulting crystal was recrystallized from ethyl acetate-hexane, to recover the objective compound (53 mg at a yield of 29%) as a colorless needle-like crystal.

Melting Point: 121–123° C. IR (KBr) cm$^{-1}$: 3242, 2961, 1652, 1570, 1525. 1H-NMR (d$_6$-DMSO) δ: 1.15 (12H, d, J=6.8 Hz), 1.28–1.87 (12H, m), 2.15–2.27 (2H, m), 2.30–2.40 (2H, m), 2.95–3.05 (1H, m), 3.01 (2H, t, J=7.1 Hz), 3.11 (2H, sept, J=6.8 Hz), 3.66 (1H, dt, J=11.5 ,3.8 Hz), 7.12 (1H, d, J=8.6 Hz), 7.12 (1H, d, J=6.8 Hz), 7.22 (1H, dd, J=8.6, 6.8 Hz), 8.70 (1H, br s). EIMS m/z (relative intensity): 430 (M$^+$), 204 (100). Elementary Analysis: $C_{26}H_{38}N_2O_2S$ Required: C, 69.73; H, 8.89; N, 6.50. Found: C, 69.56; H, 9.00; N, 6.30.

Example 67

Production of 6-[(±)3a, 7a-cis-3a,4,5,6,7,7a-hexahydrobenzoxazol-2-ylthio]-N-(2,6-diisopropylphenyl)hexanamide In the same manner as in Example 66 except for the use of (±)-cis-2-aminocyclohexanol instead of (±)-trans-2-aminocyclohexanol, reaction progressed to recover (±)-2-mercapto-3a, 7a-cis-3a,4,5,6,7,7a-hexahydrobenzoxazole; subsequently, in the same manner by using 6-bromo-N-(2, 6-diisopropylphenyl)hexanamide, reaction progressed, to recover the objective compound as a colorless needle-like crystal.

Melting Point: 96–97° C. IR (KBr) cm$^{-1}$: 3253, 2964, 2939, 1647, 1592. 1H-NMR (d$_6$-DMSO) δ: 1.15 (12H, d, J=6.8 Hz), 1.32–1.83 (14H, m), 2.36 (2H, m), 3.02 (2H, t, J=7.3 Hz), 3.11 (2H, sept, J=6.8 Hz), 3.97 (1H, dt, J=8.1, 5.6 Hz), 4.65 (1H, d t, J=8.1, 5.3 Hz), 7.12 (1H, d, J=8.6 Hz), 7.12 (1H, d, J=6.8 Hz), 7.23 (1H, dd, J=8.6, 6.8 Hz), 8.71 (1H, br s). EIMS m/z (relative intensity): 430 (M$^+$), 204 (100). Elementary Analysis: $C_{25}H_{38}N_2O_2S$ Required: C, 69.73; H, 8.89; N, 6.50; S, 7.44. Found: C, 69.51; H, 8.90; N, 6.35; S, 7.62

Example 68

Production of 6-(imidazol-2-ylthio)-N-(2,6-diisopropylphenyl)hexanamide

To a solution of 2-mercaptoimidazole (56 mg, 0.56 mmol) and 6-bromo-N-(2,6-diisopropylphenyl)hexanamide (198 mg, 0.56 mmol) in DMF (4 ml) were added potassium carbonate (85 mg, 0.62 mmol) and 18-crown-6 (15 mg, 0.06 mmol), with stirring at 80° C. for 6 hours. The reaction solution was diluted with water, and extracted with ethyl acetate. The organic layer was washed with water and dried over anhydrous magnesium sulfate, from which the solvents were distilled off. The residue was purified by preparative thin layer chromatography (elution solvents:chloroform:methanol=20:1); and the resulting crystal was recrystallized from methanol-ethyl acetate-hexane, to recover the objective compound (76 mg at a yield of 36%) as a colorless needle-like crystal.

Melting Point: 190–191° C. IR (KBr) cm$^{-1}$: 3235, 2960, 1644, 1530, 1093. 1H-NMR (d$_6$-DMSO) δ: 1.14 (12H, d, J=6.8 Hz), 1.45–1.60 (2H, m), 1.63–1.77 (4H, m), 2.30–2.40 (3H, m), 3.05 (2H, t, J=7.3 Hz), 3.10 (2H, sept, J=6.8 Hz), 7.00–7.09 (2H, m), 7.12 (1H, d, J=7.1 Hz), 7.12 (1H, d, J=6.6 Hz), 7.22 (1H, dd, J=7.1, 6.6 Hz), 8.70 (1H, br s). EIMS m/z (relative intensity): 373 (M$^+$, 100). Elementary Analysis: $C_{21}H_{31}N_3OS$ Required: C, 67.52; H, 8.36; N, 11.25; S, 8.58. Found: C, 67.39; H, 8.34; N, 11.11; S, 8.35.

Example 69

Production of 6-naphtho[2,3-d]oxazol-2-ylthio)-N-(2,6-diisopropylphenyl)hexanamide To a solution of 3-amino-2-naphthol (1.59 g, 10 mmol) in ethanol (50 ml) was added potassium o-ethyl dithiocarbonate (3.21 g, 20 mmol), at reflux under heating for 24 hours. After the solvents were distilled off under reduced pressure, the resulting residue was diluted with water and adjusted to acidity by using conc. hydrochloric acid, and extracted with ethyl acetate. The organic layer was washed with saturated sodium chloride solution and dried over anhydrous sodium sulfate. After the solvents were distilled off, the resulting residue was purified by silica gel column chromatography (200 g of silica gel; elution solvents; hexane:acetone=5:1 to 5:2); the resulting crystal was recrystallized from acetone-hexane, to recover 2-mercaptonaphtho[2,3-d]oxazole (1.28 g at a yield of 64%) as a pale brown crystal.

To a solution of the oxazole (102 mg, 0.5 mmol) and 6-bromo-N-(2,6-diisopropylphenyl)hexanamide (177 mg, 0.5 mmol) in DMF (3 ml) were added potassium carbonate (104 mg, 0.75 mmol) and 18-crown-6 (13 mg, 0.05 mmol), with stirring at 80° C. for 2 hours. The reaction solution was diluted with water and extracted with ether. The organic layer was washed sequentially with water and saturated sodium chloride solution and dried over anhydrous magnesium sulfate, from which the solvents were distilled off. The residue was purified by silica gel column chromatography (25 g of silica gel; elution solvents:hexane:acetone=5:1); the resulting crystal was recrystallized from acetone-hexane, to recover the objective compound (161 mg at a yield of 68%) as a colorless crystal.

Melting Point: 159–160° C. IR (KBr) cm$^{-1}$: 3425, 3230, 2964, 1647, 1516. 1H-NMR (d$_6$-DMSO) δ: 1.13 (12H, d, J=6.8 Hz), 1.54–1.97 (6H, m), 2.38 (2H, m), 3.10 (2H, sept, J=6.8 Hz), 3.42 (2H, t, J=7.2 Hz), 7.09 (1H, d, J=8.8 Hz), 7.09 (1H, d, J=6.6 Hz), 7.19 (1H, dd, J=8.8, 6.6 Hz), 7.41–7.50 (2H, m), 7.93–8.03 (4H, m), 8.67 (1H, br s), EIMS m/z (relative intensity): 474 (M$^+$, 100). Elementary Analysis: $C_{29}H_{34}N_2O_2S$ Required: C, 73.38; H, 7.22; N, 5.90; S, 6.75. Found: C, 73.38; H, 7.26; N, 5.85; S, 6.65.

Example 70

Production of 6-(5-dimethylphenylsilylmethyloxybenzoxazol-2-ylthio)-N-(2,6-diisopropylphenyl)hexanamide To a solution of 6-(5-hydroxybenzoxazol-2-ylthio)-N-(2,6-diisopropylphenyl)hexanamide (118 mg, 0.27 mmol) in DMF (1 ml) were sequentially added 18-crown-6 (7.1 mg, 0.027 mmol), potassium carbonate (56 mg, 0.40 mmol) and chloromethyldimethylphenylsilane (50 mg, 0.27 mmol), with stirring at 80° C. for 4 hours. To the reaction solution was again added chloromethyldimethylphenylsilane (25 mg, 0.13 mmol), with stirring at 80° C. for 3 hours. Still additionally, chloromethyldimethylphenylsilane (25 mg, 0.13 mmol) was added, with stirring at 80° C. for 90 minutes. The reaction mixture was diluted with water, and extracted with ethyl acetate. The organic layer was sequentially washed with water and saturated sodium chloride solution and dried over anhydrous sodium sulfate, from which the solvents were distilled off. The residue was purified by silica gel column chromatography (20 g of silica gel; elution solvents:hexane:acetone=5:1), to recover the objective compound (108 mg at a yield of 68%) as a colorless needle-like crystal.

Melting Point: 106–108° C. IR (KBr) cm$^{-1}$: 3433, 3222, 2962, 1648, 1472. 1H-NMR (d$_6$-DMSO) δ: 0.38 (6H, s), 1.12 (12H, d, J=6.8 Hz) 1.50–1.91 (6H, m), 2.34–2.39 (2H, m), 3.09 (2H, sept., J=6.8 Hz), 3.32 (2H, t, J=7.1 Hz), 3.91 (2H, s), 6.87 (1H, dd, J=8.8, 2.5 Hz), 7.08 (1H, d, J=8.3 Hz), 7.09 (1H, d, J=6.8 Hz), 7.16 (1H, d, J=2.5 Hz), 7.19 (1H, dd, J=8.3, 6.8 Hz), 7.32–7.39 (4H, m), 7.56–7.62 (2H, m), 8.65 (1H, br s) EIMS m/z (relative intensity): 558 (M$^+$, 100). Elementary Analysis: $C_{34}H_{44}N_2O_3SSi$ Required: C, 69.35; H, 7.53; N, 4.76; S, 5.45. Found: C, 69.26; H, 7.55; N, 4.76; S, 5.44.

Example 71

Production of N-(2,6-diisopropylphenyl)-N'-heptyl-N'-[6-(7-methoxycarbonylbenzoxazol-2-ylthio)hexyl]urea 6-Hexanolactone (2.28 g, 20 mmol) and heptylamine (2.42 g, 21 mmol) were stirred together at 100° C. for 2 hours. The reaction mixture was diluted with water, and extracted with ethyl acetate; the organic layer was washed with 1 N hydrochloric acid, water, an aqueous saturated sodium hydrogen carbonate solution and saturated sodium chloride solution and dried over anhydrous sodium sulfate. After the solvents were distilled off, the resulting residue was purified by silica gel column chromatography (150 g of silica gel; elution solvents:hexane:acetone=5:2 to 5:3), to recover 6-hydroxy-N-heptylhexanamide (2.1 g at a yield of 46%) as a colorless needle-like crystal (m.p.: 56–58° C.).

To a solution of the amide (2.6 g, 11 mmol) in THF (40 ml) with stirring under cooling in ice bath was added lithium aluminium hydride (1.1 g, 30 mmol) under argon atomospher, with stirring at room temperature for one hour, at 80° C. for 2 hours and at 90° C. for one hour. The resulting mixture was diluted with ether (300 ml), followed by addition of several droplets of an aqueous ammonium chloride solution, with stirring at room temperature for 30 minutes. Insoluble matters were filtered off through celite; the filtrate was concentrated; and the residue was extracted with diluted hydrochloric acid. The aqueous layer was washed with ether and ethyl acetate, and was then adjusted to alkalinity by using potassium carbonate, and extracted with chloroform extraction. The organic layer was washed with saturated sodium chloride solution and dried over potassium carbonate, from which the solvents were distilled off. The resulting solid material was crystallized in acetone-ether-hexane, to recover 6-heptylamino-1-hexanol (1.42 g at a yield of 59%) as a colorless needle-like crystal (m.p.: 50 to 52° C.).

To a solution of the aminoalcohol (646 mg, 3.0 mmol) in chloroform (4 ml) was dropwise added 2,6-diisopropylphenylisocyanate (610 mg, 3.0 mmol) under cooling in ice bath water, with stirring at ambient temperature for 2 hours. To the resulting reaction mixture was added hexane, to deposit crystal, which was then filtered and recovered as N-(2,6-diisopropylphenyl)-N'-heptyl-N'-(6-hydroxyhexyl)urea (1.09 g at a yield of 87%) as a colorless needle-like crystal (m.p.: 137–139° C.).

To a solution of the urea (419 mg, 1.0 mmol) and 4-dimethylaminopyridine (12 mg, 0.1 mmol) in THF (5 ml) were added triethylamine (142 mg, 1.4 mmol) and methanesulfonyl chloride (137 mg, 1.2 mmol) under cooling in ice bath, and the resulting mixture was stirred at the temperature for 2 hours. After insoluble matters were filtered off, the resulting solution was concentrated. The residue was extracted with ethyl acetate; the organic layer was washed with water and saturated sodium chloride solution and dried over sodium sulfate, from which the solvents were distilled off. The resulting solid matter was crystallized in hexane-ethyl acetate, to recover 6-[3-(2,6-diisopropylphenyl)-1-heptylureido]hexyl methanesulfonate (433 mg at a yield of 87%) as a colorless needle-like crystal (m.p.: 140–141° C.).

A solution of the methanesulfonate (199 mg, 0.4 mmol) in DMF (2 ml) was added to a solution of 7-methoxycarbonyl-2-mercaptobenzoxazole (84 mg, 0.4 mmol), potassium carbonate (83 mg, 0.6 mmol) and 18-crown-6 (11 mg, 0.04 mmol) in DMF (1 ml), with stirring at 80° C. for 90 minutes. The reaction solution was diluted with water, and extracted with ethyl acetate. The organic layer was washed sequentially with water and saturated sodium chloride solution and dried over anhydrous sodium sulfate, from which the solvents were distilled off. The residue was purified by silica gel column chromatography (25 g of silica gel; elution solvents:hexane:acetone=20:1 to 5:1), to recover the objective compound (131 mg at a yield of 54%) as a colorless needle-like crystal.

Melting Point: 120–121° C. IR (KBr) cm$^{-1}$: 3425, 3328, 1728, 1624, 1507. 1H-NMR (d$_6$-DMSO) δ: 0.86 (3H, t, J=6.8 Hz), 1.11 (12H, d, J=6.8 Hz) 1.26–1.31 (8H, m), 1.37–1.42 (2H, m), 1.47–1.60 (6H, m), 1.81–1.88 (2H, m), 3.14 (2H, sept, J=6.8 Hz), 3.25–3.31 (2H, m), 3.36 (1H, t, J=7.1 Hz), 3.93 (3H, s) 7.04 (1H, br s), 7.05 (2H, d, J=7.8 Hz), 7.15 (1H, t, J=7.8 Hz), 7.41 (1H, m), 7.78–7.84 (2H, m) EIMS m/z (relative intensity): 609 (M$^+$), 189 (100) Elementary Analysis: $C_{35}H_{51}N_3O_4S$ Required: C, 68.93; H, 8.43; N, 6.89; S, 5.26. Found: C, 69.09; H, 8.50; N, 6.84; S, 5.10.

Example 72

Production of N-(2,6-diisopropylphenyl)-N'-heptyl-N'-[6-(oxazolo[4,5-b]pyridin-2-ylthio)hexyl]urea In the same manner as in Example 71 except for the use of 2-mercaptooxazolo[4,5-b]pyridine instead of 7-methoxycarbonyl-2-mercaptobenzoxazole, reaction progressed to recover the objective compound as a colorless needle-like crystal.

Melting Point: 124–125° C. IR (KBr) cm$^{-1}$: 3420, 3328, 1624, 1507, 1402. 1H-NMR (d$_6$-DMSO) δ: 0.86 (3H, t, J=7.0 Hz), 1.11 (2.4H, d, J=6.8 Hz), 1.11 (9.6H, d, J=6.8 Hz), 1.26–1.32 (8H, m), 1.37–1.43 (2H, m), 1.47–1.60 (6H, m), 1.81–1.93 (2H, m), 3.10–3.19 (2H, m), 3.25–3.31 (2H, m), 3.38 (1.6H, t, J=7.2 Hz), 4.22 (0.4H, t, J=7.2 Hz), 7.05 (1H, d, J=8.3 Hz), 7.06 (1H, br s), 7.06 (1H, d, J=6.8 Hz), 7.15 (1H, dd, J=8.3, 6.8 Hz), 7.28 (0.8H, dd, J=8.3, 4.9 Hz), 7.30 (0.2H, dd, J=8.3, 4.9 Hz), 7.84 (0.2H, dd, J=8.3, 1.5 Hz), 7.95 (0.8H, dd, J=8.3, 1.5 Hz), 8.28 (0.2H, dd, J=4.9, 1.5 Hz), 8.39 (0.8H, dd, J=4.9, 1.5 Hz). EIMS m/z (relative intensity): 552 (M$^+$), 188 (100) Elementary Analysis: $C_{32}H_{48}N_4O_2S$ Required: C, 69.53; H, 8.75; N, 10.13; S, 5.80. Found: C, 69.65; H, 8.83; N, 10.09; S, 5.86.

Example 73

Production of 2-(7-trifluoromethylbenzoxazol-2-ylthio)-N-(2,6-diisopropylphenyl)acetamide In the same manner as in Example 11 except for the use of 2-nitro-6-trifluoromethylphenol instead of 3-hydroxy-6-methyl-nitropyridine, reaction progressed to recover 2-mercapto-7-trifluoromethylbenzoxazole (110 mg, 0.5 mmol); to a solution of the 2-mercapto-7-trifluoromethylbenzoxazole (110 mg, 0.5 mmol) and 2-bromo-N-(2,6-diisopropylphenyl)acetamide (149 mg, 0.5 mmol) was added potassium carbonate (76 mg, 0.55 mmol), with stirring at ambient temperature for one hour. The reaction solution was diluted with water, and extracted with ethyl acetate. The organic layer was sequentially washed with water and saturated sodium chloride solution and dried over sodium sulfate, from which the solvents were distilled off. The residue was purified by preparative thin layer chromatography (elution solvents:hexane:acetone=5:2), to recover the objective compound (61 mg at a yield of 28%) as a colorless needle-like crystal.

Melting Point: 172–173° C. IR (KBr) cm$^{-1}$: 3432, 3267, 2967, 1664, 1509. 1H-NMR (CDCl$_3$) δ: 1.04–1.12 (12H, m), 2.99 (2H, sept, J=6.9 Hz), 4.15 (2H, s), 7.14 (2H, d, J=7.8 Hz), 7.28 (1H, t, J=7.8 Hz), 7.42 (1H, t, J=7.9 Hz), 7.55 (1H, d, J=7.9 Hz), 7.76 (1H, d, J=7.9 Hz), 8.36 (1H, br s). EIMS m/z (relative intensity): 436 (M$^+$, 100) Elementary Analysis: $C_{22}H_{23}F_3N_2O_2S$ Required: C, 60.54; H, 5.31; N, 6.42; F, 13.06. Found: C, 60.42; H, 5.32; N, 6.39; F, 12.95.

Example 74

Production of 6-(7-trifluoromethylbenzoxazol-2-ylthio)-N-(2,6-diisopropylphenyl)hexanamide In the same manner as in Example 73 except for the use of 6-bromo-N-(2,6-diisopropylphenyl)hexanamide instead of 2-bromo-N-(2,6-diisopropylphenyl)acetamide, reaction progressed to recover the objective compound as a colorless needle-like crystal.

Melting Point: 130° C. IR (KBr) cm$^{-1}$: 3227, 2968, 1645, 1534, 1490. 1H-NMR (d$_6$-DMSO) δ: 1.11 (12H, d, J=7.0 Hz), 1.56 (2H, m), 1.72 (2H, m), 1.89 (2H, m), 2.36 (2H, m), 3.08 (2H, sept, 6.8 Hz), 3.39 (2H, t, J=7.1 Hz), 7.09 (2H, d, J=7.6 Hz), 7.20 (1H, t, J=7.6 Hz), 7.50 (1H, t, J=7.9 Hz), 7.59 (1H, d, J=7.9 Hz), 7.88 (1H, d, J=7.9 Hz), 8.69 (1H, br s). EIMS m/z (relative intensity): 492 (M$^+$), 69 (100). Elementary Analysis: $C_{26}H_{31}F_3N_2O_2S$ Required: C, 63.40; H, 6.34; N, 5.69. Found: C, 63.11; H, 6.43; N, 5.65.

Example 75

Production of 9-(7-trifluoromethylbenzoxazol-2-ylthio)-N-(2,6-diisopropylphenyl)nonanamide In the same manner as in Example 73 except for the use of 9-bromo-N-(2,6-diisopropylphenyl)nonanamide instead of 2-bromo-N-(2,6-diisopropylphenyl)acetamide, reaction progressed to recover the objective compound as a colorless needle-like crystal.

Melting Point: 82–84° C. IR (KBr) cm$^{-1}$: 3436, 3244, 1648, 1506, 1332. 1H-NMR (d$_6$-DMSO) δ: 1.11 (12H, d, J=6.8 Hz), 1.34–1.41 (6H, m), 1.44–1.51 (2H, m), 1.61–1.68 (2H, m), 1.84 (2H, quint, J=7.2 Hz). 2.29–2.35 (2H, m), 3.08 (2H, sept, J=6.8 Hz), 3.37 (2H, t, J=7.2 Hz), 7.09 (2H, d, J=7.6 Hz), 7.19 (1H, t, J=7.6 Hz), 7.50 (1H, ddd, J=8.1, 7.8, 0.7 Hz), 7.59 (1H, d, J=7.8 Hz), 7.88 (1H, d, J=8.1 Hz), 8.67 (1H, br s). EIMS m/z (relative intensity): 534 (M$^+$, 100) Elementary Analysis: $C_{29}H_{37}F_3N_2O_2S$ Required: C, 65.15; H, 6.97; N, 5.24; F, 10.66. Found: C, 65.31; H, 6.92; N, 5.29; F, 10.51.

Example 76

Production of 6-(5-trifluoromethylbenzoxazol-2-ylthio)-N-(2,6-diisopropylphenyl]hexanamide In the same manner as in Example 11 except for the use of 2-nitro-4-trifluoromethylphenol instead of 3-hydroxy-6-methyl-2-nitropyridine, reaction progressed to recover 2-mercapto-5-trifluoromethylbenzoxazole. The resulting product was subjected to the same reaction in the same manner as in Example 74, to recover the objective compound as a colorless crystal.

Melting Point: 98° C. IR (KBr) cm$^{-1}$: 3232, 2964, 1648 1500. 1H-NMR (d$_6$-DMSO) δ: 1.12 (12H, d, J=6.8 Hz), 1.56 (2H, m), 1.72 (2H, m), 1.88 (2H, m), 2.36 (2H, m), 3.08 (2H, sept, J=6.8 Hz), 3.40 (2H, t, J=7.0 Hz), 7.10 (2H, d, J=7.3 Hz), 7.20 (1H, t, J=7.3 Hz), 7.63 (1H, d, J=8.6 Hz), 7.79 (1H, d, J=8.6 Hz), 7.92 (1H, s), 8.70 (1H, br s). EIMS m/z (relative intensity): 492 (M$^+$, 100). Elementary Analysis: $C_{26}H_{31}F_3N_2O_2S$ Required: C, 63.40; H, 6.34; N, 5.69. Found: C, 63.47; H, 6.62; N, 5.45.

Example 77

Production of 6-(7-tert-butylbenzoxazol-2-ylthio)-N-(2,6-diisopropylphenyl)hexanamide To a solution of 2-tert-butylphenol (2.00 g, 13.3 mmol) in acetonitrile (30 ml) was dropwise added at −20° C. acetyl nitricate recovered by mixing together acetic anhydride (1.35 g, 13.3 mmol) and fuming nitric acid (13.3 mmol) at −0° C., with stirring for 5 minutes. The reaction solution was diluted with water, and extracted with ethyl acetate. The organic layer was sequentially washed with water and saturated sodium chloride solution and dried over anhydrous magnesium sulfate, from which the solvents were distilled off. The residue was purified by silica gel column chromatography (60 g of silica gel; elution solvents:hexane:acetone=3:1), to recover 2-tert-butyl-6-nitrophenol (600 mg at a yield of 23%) as a yellow crystal.

In the same manner as in Example 11 except for the use of 2-tert-butyl-6-nitrophenol instead of 3-hydroxy-6-methyl-2-nitropyridine, reaction progressed to recover the objective compound as a colorless crystal.

Melting Point: 141–142° C. IR (KBr) cm$^{-1}$: 3247, 2961, 1654, 1505, 1117. 1H-NMR (d$_6$-DMSO) δ: 1.11 (12H, d, J=6.8 Hz), 1.57 (2H, m), 1.72 (2H, m), 1.88 (2H, m), 2.36 (2H, m), 3.08 (2H, sept, J=6.8 Hz), 3.35 (2H, J=7.0 Hz), 7.09 (2H, d, J=7.8 Hz), 7.18 (1H, dd, J=7.8, 1.4 Hz), 7.19 (1H, t, J=7.8 Hz), 7.23 (1H, t, J=7.8 Hz), 7.42 (1H, dd, J=7.8, 1.4 Hz), 8.71 (1H, br s). EIMS m/z (relative intensity): 480 (M$^+$, 100). Elementary Analysis: $C_{26}H_{40}N_2O_2S$ Required: C, 72.46; H, 8.39; N, 5.83. Found: C, 72.19; H, 8.35; N, 5.68.

Example 78

Production of 6-(4,5,6-trimethoxybenzoxazol-2-ylthio)-N-(2,6-diisopropylphenyl)hexanamide In the same manner as in Example 1 except for the use of 4,5,6-trimethoxy-2-mercaptobenzoxazole instead of 2-mercaptooxazolo[4,5-b]pyridine, reaction progressed to recover the objective compound as a pale yellow needle-like crystal.

Melting Point: 96–98° C. (dec.) IR (KBr) cm$^{-1}$: 3428, 3231, 2964, 1648, 1485. 1H-NMR (d$_6$-DMSO) δ: 1.12 (12H, d, J=6.9 Hz), 1.51–1.59 (2H, m), 1.69–1.72 (2H, m), 1.81–1.89 (2H, m), 2.35 (2H, t, J=7.1 Hz), 3.08 (2H, sept, J=6.9 Hz), 3.30 (2H, t, J=7.1 Hz), 3.72 (3H, s), 3.82 (3H, s), 4.18 (3H, S), 6.97 (1H, S), 7.09 (2H, d, J=7.8 Hz), 7.20 (1H, t, J=7.8 Hz), 8.67 (1H, br s) EIMS m/z (relative intensity): 514 (M$^+$, 100). Elementary Analysis: $C_{28}H_{38}N_2O_5S$ Required: C, 65.34; H, 7.44; N, 5.44; S, 6.23. Found: C, 65.17; H, 7.45; N, 5.44; S, 6.26.

Example 79

Production of 6-(7-ethoxycarbonylbenzoxazol-2-ylthio)-N-(2,6-diisopropylphenyl)hexanamide A solution of 6-(7-methoxycarbonylbenzoxazol-2-ylthio)-N-(2,6-diisopropylphenyl)hexanamide (145 mg, 0.3 mmol) and 4-dimethylaminopyridine (3.7 mg, 0.03 mmol) in ethanol (30 ml) was refluxed under heating for 24 hours. After concentration, the reaction solution was diluted with water, and extracted with ethyl acetate. The organic layer was sequentially washed with 0.05 N hydrochloric acid, water and saturated sodium chloride solution and dried over anhydrous sodium sulfate, from which the solvents were distilled off. The residue was purified by preparative thin layer chromatography (elution solvents:hexane:acetone=

5:2), to recover the objective compound (95 mg at a yield of 64%) as a colorless needle-like crystal.

Melting Point: 114–116° C. IR (KBr) cm$^{-1}$: 3425, 3241, 2965, 1717, 1647. 1H-NMR (d$_6$-DMSO) δ: 1.11 (12H, d, J=6.8 Hz), 1.37 (3H, t, J=7.1 Hz), 1.54–1.61 (2H, m), 1.69–1.76 (2H, m), 1.86–1.93 (2H, m), 2.36 (2H, t, J=7.2 Hz), 3.08 (2H, sept, J=6.8 Hz), 3.39 (2H, t, J=7.2 Hz), 4.40 (2H, q, J=7.1 Hz), 7.09 (2H, d, J=7.8 Hz), 7.19 (1H, t, J=7.8 Hz), 7.42 (1H, t. J=7.8 Hz), 7.79 (1H, dd, J=7.8, 1.2 Hz), 7.83 (1H, dd, J=7.8, 1.2 Hz), 8.70 (1H, br s). EIMS m/z (relative intensity): 496 (M$^+$), 67 (100). Elementary Analysis: C$_{28}$H$_{36}$N$_2$O$_4$S Required: C, 67.71; H, 7.31; N, 5.64; S, 6.46. Found: C, 67.83; H, 7.33; N, 5.63; S, 6.52.

Example 80

Production of 6-(7-methoxymethylcarbonylbenzoxazol-2-ylthio)-N-(2,6-diisopropylphenyl)hexanamide To a solution of 6-(7-carboxybenzoxazol-2-ylthio)-N-(2,6-diisopropylphenyl)hexanamide (141 mg, 0.3 mmol) in DMF (2 ml) were added triethylamine (36 mg, 0.36 mmol) and chloromethyl methyl ether (27 mg, 0.33 mmol), and the resulting mixture was stirred at ambient temperature for 50 minutes. The reaction solution was diluted with water, and extracted with ethyl acetate. The organic layer was sequentially washed with water and saturated sodium chloride solution and dried over anhydrous sodium sulfate, from which the solvents were distilled off. The residue was purified by silica gel column chromatography (10 g of silica gel; elution solvents:hexane:acetone=5:2), to recover the objective compound (119 mg at a yield of 77%) as a colorless needle-like crystal.

Melting Point: 120–122° C. IR (KBr) cm$^{-1}$: 3433, 3241, 2963. 1729, 1649. 1H-NMR (d$_6$-DMSO) δ: 1.11 (12H, d, J=6.8 Hz), 1.54–1.61 (2H, m),1.64–1.76 (2H, 1.86–1.93 (2H, m), 2.35–2.38 (2H, m), 3.08 (2H, sept, J=6.8 Hz), 3.40 (2H, t, J=7.1 Hz), 3.52 (3H, s), 5.50 (2H, s), 7.09 (2H, d, J=7.8 Hz), 7.19 (1H, t, J=7.8 Hz), 7.44 (1H, t, J=7.8 Hz), 7.83 (1H, dd, J=7.8, 1.2 Hz) 7.86 (1H, dd, J=7.8, 1.2 Hz), 8.70 (1H, br s) EIMS m/z (relative intensity): 512 (M$^+$), 67 (100). Elementary Analysis: C$_{28}$H$_{36}$N$_2$O$_2$S Required: C, 65.60; H, 7.08; N, 5.46; S, 6.25. Found: C, 65.69; H, 7.12; N, 5.42; S, 6.45.

Example 81

Production of 6-(7-tert-butoxycarbonylbenzoxazol-2-ylthio)-N-(2,6-diisopropylphenyl)hexanamide To a suspension of 6-(7-carboxybenzoxazol-2-ylthio)-N-(2,6-diisopropylphenyl)hexanamide (141 mg, 0.3 mmol) in toluene (3 ml) was dropwise added N,N-dimethylformamide-di-tert-butyl acetal (305 mg, 1.5 mmol) with stirring at 100° C. The reaction mixture in solution was left to stand and cooled and was then diluted with water, and extracted with ethyl acetate. The organic layer was sequentially washed with water and saturated sodium chloride solution and dried over sodium sulfate, from which the solvents were distilled off. The residue was crystallized from hexane-ether-acetone, to recover the objective compound (130 mg at a yield of 83%) as a colorless needle-like crystal.

Melting Point: 137–140° C. IR (KBr) cm$^{-1}$: 3256, 2967, 1713, 1651, 1505. 1H-NMR (d$_6$-DMSO) δ: 1.11 (12H, d, J=6.8 Hz), 1.54–1.62 (2H, m), 1.60 (9H, s), 1.68–1.76 (2H, m), 1.84–1.92 (2H, m), 2.36 (2H, t, J=6.6 Hz), 3.08 (2H, sept, J=6.8 Hz), 3.39 (2H, t, J=7.0 Hz), 7.09 (2H, d, J=7.6 Hz), 7.19 (1H, t, J=7.6 Hz), 7.39 (1H, t, J=7.8 Hz), 7.73 (1H, dd, J=7.8, 1.2 Hz), 7.79 (1H, dd, J=7.8, 1.2 Hz), 8.70 (1H, br s). EIMS m/z (relative intensity): 524 (M$^+$), 468 (100). Elementary Analysis: C$_{30}$H$_{40}$N$_2$O$_4$S Required: C, 68.67; H, 7.68; N, 5.34; S, 6.11. Found: C, 68.70; H, 7.54; N, 5.33; S, 6.23.

Example 82

Production of 6-(7-tert-butoxycarbonylmethyloxybenzoxazol-2-ylthio)-N-(2,6-diisopropylphenyl)hexanamide In the same manner as in Example 59 except for the use of tert-butyl glycolic acid instead of N,N-dimethyl ethanolamine, reaction progressed to recover the objective compound as a colorless needle-like crystal.

Melting Point: 77–79° C. IR (KBr) cm$^{-1}$: 3244, 2964, 1755, 1735, 1647. 1H-NMR (d$_6$-DMSO) δ: 1.12 (12H, d, J=6.8 Hz), 1.45 (9H, s), 1.52–1.62 (2H, m), 1.64–1.74 (2H, m), 1.84–1.92 (2H, m), 2.36 (2H, t, J=6.8 Hz), 3.08 (2H, sept, J=6.8 Hz), 3.40 (2H, t, J=7.0 Hz), 4.81 (2H, s), 7.09 (2H, d, J=7.6 Hz), 7.19 (1H, t, J=7.6 Hz), 7.45 (1H, t, J=7.8 Hz), 7.84 (1H, dd, J=7.8, 1.2 Hz), 7.87 (1H, dd, J=7.8, 1.2 Hz), 8.70 (1H, br s). EIMS m/z (relative intensity): 582 (M$^+$), 525 (100). Elementary Analysis: C$_{32}$H$_{42}$N$_2$O$_6$S Required: C, 65.95; H, 7.26; N, 4.81; S, 5.50. Found: C, 66.09; H, 7.29; N, 4.78; S, 5.53.

Example 83

Production of 6-[7-(3-methyloxethan-3-ylmethyloxycarbonyl)benzoxazol-2-ylthio)-N-(2,6-diisopropylphenyl)hexanamide In the same manner as in Example 59 except for the use of 3-methyl-3-oxethane methanol instead of N,N-dimethyl ethanolamine, reaction progressed to recover the objective compound (340 mg at a yield of 60%) as a colorless needle-like crystal.

Melting Point: 145–147° C. IR (KBr) cm$^{-1}$: 3425, 3254, 2965, 1722, 1647. 1H-NMR (d$_6$-DMSO) δ: 1.12 (12H, d, J=6.8 Hz), 1.40 (3H, s), 1.52–1.62 (2H, m), 1.64–1.76 (2H, m), 1.84–1.92 (2H, m), 2.36 (2H, t, J=6.9 Hz), 3.08 (2H, sept, J=6.8 Hz), 3.39 (2H, t, J=7.0 Hz), 4.32 (2H, d, J=5.9 Hz), 4.47 (2H, s), 4.54 (2H, J=5.9 Hz), 7.09 (2H, d, J=7.6 Hz), 7.20 (1H, t, J=7.6 Hz), 7.44 (1H, t, J=8.0 Hz), 7.83 (1H, dd, J=8.0, 1.2 Hz), 7.85 (1H, dd, J=8.0, 1.2 Hz), 8.70 (1H, br s). EIMS m/z (relative intensity): 552 (M$^+$), 230 (100). Elementary Analysis: C$_{31}$H$_{40}$N$_2$O$_5$S Required: C, 69.50; H, 7.34; N, 6.00; S, 6.87. Found: C, 69.47; H, 7.33; N, 6.08; S, 6.95.

Example 84

Production of 6-[7-(4,4-dimethyloxazolin-2-yl)benzoxazol-2-ylthio]-N-(2,6-diisopropylphenyl)hexanamide 6-(7-Methoxycarbonylbenzoxazol-2-ylthio)-N-(2,6-diisopropylphenyl)hexanamide (241 mg, 0.5 mmol) was added to 2-amino-2-methyl-1-propanol (3 ml), with stirring at 100° C. for 6 hours. The reaction solution was diluted with water, and extracted with ethyl acetate. The organic layer was sequentially washed with diluted hydrochloric acid, water, an aqueous sodium hydrogen carbonate solution and saturated sodium chloride solution and dried over anhydrous magnesium sulfate, from which the solvents were distilled off. The residue was purified by silica gel column chromatography (20 g of silica gel; elution solvents:hexane:acetone=5:2), to recover 6-[7-[N-(1-hydroxy-2-methyl-2propyl)carbamoyl]benzoxazol-2-ylthio]-N-(2,6-diisopropylphenyl)hexanamide (140 mg at a yield of 52%) as a pale yellow needle-like crystal.

The amide (108 mg, 0.2 mmol) was added to phosphorus oxychloride (1 ml) under cooling in ice bath, and the resulting mixture was stirred at the temperature for 10 minutes. The reaction mixture was poured into ice bath water, and extracted with ethyl acetate. The organic layer was sequentially washed with water and saturated sodium chloride solution and dried over anhydrous sodium sulfate, from which the solvents were distilled off. The resulting residue was purified by preparative thin layer chromatography (elution solvents; hexane:acetone=5:3), to recover the objective compound (67 mg at a yield of 64%) as a colorless needle-like crystal.

Melting Point: 127–129° C. IR (KBr) cm$^{-1}$: 3430, 3261, 2964, 1652, 1505. 1H-NMR (d$_6$-DMSO) δ: 1.12 (12H, d, J=6.8 Hz), 1.33 (6H, s), 1.52–1.62 (2H, m), 1.66–1.76 (2H, m), 1.86–1.94 (2H, m), 2.36 (2H, t, J=6.8 Hz), 3.08 (2H, sept, J=6.8 Hz), 3.37 (2H, t, J=7.2 Hz), 4.13 (2H, s), 7.09 (2H, d, J=7.6 Hz), 7.19 (1H, t, J=7.6 Hz), 7.37 (1H, t, J=7.9 Hz), 7.71 (1H, dd, J=7.9, 1.2 Hz), 7.72 (1H, dd, J=7.9, 1.2 Hz), 8.70 (1H, br s). EIMS m/z (relative intensity): 521 (M$^+$), 262 (100). Elementary Analysis: C$_{30}$H$_{39}$N$_3$O$_3$S Required: C, 69.07; H, 7.53; N, 8.05; S, 6.15. Found: C, 69.05; H, 7.56; N, 7.95; S, 6.24.

Example 85

Production of 6-[7-([1,3]dioxolan-2-yl)benzoxazol-2-ylthio]-N-(2,6-diisopropylphenyl)hexanamide To a solution of 6-(7-hydroxymethylbenzoxazol-2-ylthio)-N-(2,6-diisopropylphenyl)hexanamide (440 mg, 1.0 mmol) in methylene chloride (10 ml) were sequentially added molecular sieves 4A (powder, 2 g) and pyridinium dichromate (1.1 g, 2.9 mmol), and the resulting mixture was stirred at ambient temperature for 30 minutes. The reaction mixture was diluted with ether and filtered off through celite; and the filtrate was concentrated. The residue was purified by silica gel column chromatography (20 g of silica gel; elution solvents; hexane:acetone=5:3), to recover 6-(7-formylbenzoxazol-2-ylthio)-N-(2,6-diisopropylphenyl)hexanamide (330 mg at a yield of 75%) as a colorless needle-like crystal.

To a solution of the aldehyde (136 mg, 0.3 mmol) in toluene (5 ml) were sequentially added ethylene glycol (130 mg, 2.1 mmol), trimethyl o-formate (133 mg, 0.9 mmol) and p-toluenesulfonic acid.monohydrate (10 mg, 0.05 mmol), with stirring at 50° C. for 4 hours and additionally at 100° C. for 4 hours. The resulting reaction solution was diluted with water, and extracted with ethyl acetate. The organic layer was washed sequentially with an aqueous saturated sodium hydrogen carbonate solution, water and saturated sodium chloride solution and dried over anhydrous sodium sulfate, from which the solvents were distilled off. The residue was purified by preparative thin layer chromatography (elution solvents:hexane:acetone=5:2), to recover a solid matter; then, the solid matter was crystallized from hexane-ether, to recover the objective compound (76 mg at a yield of 51%) as a colorless needle-like crystal.

Melting Point: 105–107° C. IR (KBr) cm$^{-1}$: 3432, 3221, 2963, 1643, 1537. 1H-NMR (d$_6$-DMSO) δ: 1.12 (12H, d, J=6.8 Hz), 1.52–1.61 (2H, m), 1.67–1.76 (2H, m), 1.82–1.91 (2H, m), 2.36 (2H, t, J=6.9 Hz), 3.08 (2H, sept, J=6.8 Hz), 3.36 (2H, t, J=7.2 Hz), 3.98–4.13 (4H, m), 6.11 (1H, s), 7.09 (2H, d, J=7.6 Hz), 7.19 (1H, t, J=7.6 Hz), 7.30 (1H, t, J=7.6 Hz), 7.34 (1H, dd, J=7.6, 1.6 Hz), 7.59 (1H, dd, J=7.6, 1.6 Hz), 8.70 (1H, br s). EIMS m/z (relative intensity): 496 (M$^+$,100). Elementary Analysis: C$_{28}$H$_{36}$N$_2$O$_4$S Required: C, 67.71; H, 7.31; N, 5.64; S, 6.46. Found: C, 67.88; H, 7.31; N, 5.62; S, 6.61.

Example 86

Production of 6-[7-(4R,5R)-4,5-dimethyl[1,3]dioxolan-2-yl)benzoxazol-2-ylthio]-N-(2,6-diisopropylphenyl)hexanamide In the same manner as in Example 85 except for the use of (2R,3R)-2,3-butanediol instead of ethylene glycol, reaction progressed to recover the objective compound (101 mg at a yield of 64%) as a colorless needle-like crystal.

Melting Point: 115–117° C. IR (KBr) cm$^{-1}$: 3424, 3236, 2969, 1646, 1499. 1H-NMR (d$_6$-DMSO) δ: 1.12 (12H, d, J=6.8 Hz), 1.27–1.33 (6H, m), 1.52–1.62 (2H, m), 1.66–1.76 (2H, m), 1.86–1.94 (2H, m), 2.36 (2H, t, J=6.2 Hz), 3.08 (2H, sept, J=6.8 Hz), 3.36 (2H, t, J=7.2 Hz), 3.79–3.87 (2H, m), 6.21 (1H, s), 7.09 (2H, d, J=7.6 Hz), 7.19 (1H, t, J=7.6 Hz), 7.30 (1H, t, J=7.6 Hz), 7.35 (1H, dd, J=7.6, 1.4 Hz), 7.58 (1H, dd, J=7.6, 1.4 Hz), 8.70 (1H, br s). EIMS m/z (relative intensity): 524 (M$^+$), 452 (100). Elementary Analysis: C$_{30}$H$_{40}$N$_2$O$_4$S Required: C, 68.67; H, 7.68; N, 5.34; S, 6.11. Found: C, 68.87; H, 7.68; N, 5.28; S, 6.24.

Example 87

Production of 6-(7-acetylbenzoxazol-2-ylthio)-N-(2,6-diisopropylphenyl)hexanamide Potassium o-ethyl dithiocarbonate (241 mg, 1.5 mmol) was added to a solution of 3-amino-2-hydroxyacetophenone (113 mg, 0.75 mmol) in ethanol (10 ml), at reflux under heating for 16 hours, from which the solvent was distilled off. The residue was dissolved in water, followed by addition of 2 N hydrochloric acid to adjust the resulting solution to pH 3 to 4. The deposited crystal was filtered and recovered; then, the crystal was washed with water and dried with heating under reduced pressure, to recover 7-acetyl-2-mercaptobenzoxazole (134 mg at a yield of 92%) as a brown solid.

In the same manner as in Example 1 except for the use of the oxazole herein recovered instead of 2-mercaptooxazolo[4,5-b]pyridine, reaction progressed to recover the objective compound as a colorless needle-like crystal.

Melting Point: 156–158° C. IR (KBr) cm$^{-1}$: 3437, 3218, 2958, 1682, 1651. 1H-NMR (d$_6$-DMSO) δ: 1.12 (12H, d, J=6.8 Hz), 1.52–1.62 (2H, m), 1.66–1.76 (2H, m), 1.86–1.94 (2H, m), 2.37 (2H, t, J=6.9 Hz), 2.69 (3H, s), 3.08 (2H, sept, J=6.8 Hz), 3.40 (2H, t, J=7.0 Hz), 7.09 (2H, d, J=7.6 Hz), 7.20 (1H, t, J=7.6 Hz), 7.42 (1H, t, J=7.8 Hz), 7.75 (1H, dd, J=7.8, 1.1 Hz), 7.82 (1H, dd, J=7.8, 1.1 Hz), 8.71 (1H, br s). EIMS m/z (relative intensity): 466 (M$^+$), 177 (100). Elementary Analysis: C$_{27}$H$_{34}$N$_2$O$_3$S Required: C, 69.50; H, 7.34; N, 6.00; S, 6.87. Found: C, 69.47; H, 7.33; N, 6.08; S, 6.95.

Example 88

Production of 6-[7-(pyrazol-3-yl)benzoxazol-2-ylthio]-N-(2,6-diisopropylphenyl)hexanamide To a solution of 6-(7-acetylbenzoxazol-2-ylthio)-N-(2,6-diisopropylphenyl)hexanamide (155 mg, 0.33 mmol) in DMF (3 ml) was added N,N-dimethylformamidedimethylacetal (191 mg, 1.6 mmol), with stirring at 50° C. for 4 hours and additionally at 100° C. for 15 hours. The reaction solution was diluted with water, and extracted with ethyl acetate. The organic layer was sequentially washed with water and saturated sodium chloride solution and dried over sodium sulfate, from which the solvent was distilled off. The residue was purified by preparative thin layer chromatography (elution solvents:hexane:acetone=5:3), to recover 6-[7-(3-dimethylaminoacryloyl)benzoxazol-2-ylthio]-N-(2,6-diisopropylphenyl)hexanamide (146 mg at a yield of 85%) as a pale yellow needle-like crystal.

To a solution of the enamine (104 mg, 0.2 mmol) in methanol (3 ml) were added acetic acid (60 mg, 1.0 mmol) and hydrazine.monohydrate (50 g, 1.0 mmol), with stirring at ambient temperature for 2 hours. The reaction solution was concentrated and then diluted with water, and extracted with ethyl acetate. The organic layer was sequentially washed with water and saturated sodium chloride solution and dried over sodium sulfate, from which the solvents were distilled off. The residue was purified by preparative thin layer chromatography (elution solvents:hexane:acetone=1:1), to recover the objective compound (75 mg at a yield of 76%) as a colorless needle-like crystal.

Melting Point: 174–176° C. IR (KBr) cm$^{-1}$: 3236, 2964, 1647, 1530, 1493. 1H-NMR (d$_6$-DMSO) δ: 1.12 (12H, d, J=6.8 Hz), 1.52–1.62 (2H, m), 1.66–1.76 (2H, m), 1.86–1.94 (2H, m), 2.37 (2H, t, J=6.9 Hz), 3.08 (2H, sept, J=6.8 Hz), 3.40 (2H, t, J=6.7 Hz), 6.81 (1H, m), 7.09 (2H, d, J=7.6 Hz), 7.19 (1H, t, J=7.6 Hz), 7.30 (1H, t, J=7.6 Hz), 7.34 (1H, m), 7.52 (1H, m), 7.75–7.80 (2H, m), 8.70 (1H, br s), 12.79 (1H, br s). EIMS m/z (relative intensity): 490 (M$^+$), 176 (100). Elementary Analysis: C$_{28}$H$_{36}$N$_2$O$_4$S Required: C, 68.54; H, 6.98; N, 11.42; S, 6.53. Found: C, 68.65; H, 7.05; N, 11.30; S, 6.57.

Example 89

Production of 6-[6,7-bis(methoxycarbonyl) benzoxazol-2-ylthio]-N-(2,6-diisopropylphenyl) hexanamide In the same manner as in Example 1 except for the use of 6,7-bis (methoxycarbonyl)-2-mercaptobenzoxazole instead of 2-mercaptooxazolo[4,5-b]pyridine, reaction progressed to recover the objective compound as a colorless needle-like crystal.

Melting Point: 159–161° C. IR (KBr) cm$^{-1}$: 3425, 3257, 1744, 1721, 1647. 1H-NMR (d$_6$-DMSO) δ: 1.12 (12H, d, J=6.8 Hz), 1.52–1.60 (2H, m), 1.68–1.75 (2H, m), 1.85–1.92 (2H, m), 2.36 (2H, t, J=7.1 Hz), 3.08 (2H, sept, J=6.8 Hz), 3.40 (2H, t, J=7.1 Hz), 3.85 (3H, s), 3.91 (3H, s), 7.09 (2H, d, J=7.6 Hz), 7.20 (1H, t, J=7.6 Hz), 7.77 (1H, d, J=8.3 Hz), 7.81 (1H, d, J=8.3 Hz), 8.67 (1H, br s) EIMS m/z (relative intensity): 540 (M$^+$), 162 (100). Elementary Analysis: C$_{29}$H$_{36}$N$_2$O$_6$S Required: C, 64.42; H, 6.71; N, 5.18. Found: C, 64.56; H, 6.69; N, 5.26.

Example 90

Production of 6-(oxazolo[4,5-g]phthalid-2-ylthio)-N-(2,6-diisopropylphenyl)hexanamide To a solution of 2,3-bis(methoxycarbonyl)phenol (4.6 g, 20 mmol) in acetonitrile (100 ml) was dropwise added at 0° C. acetyl nitricate acid recovered by mixing together acetic anhydride (6.0 g, 60 mmol) and fuming nitric acid (3.6 g, 60 mmol) at 0° C., with stirring for 40 minutes. The reaction solution was diluted with water, and extracted with ethyl acetate. The organic layer was sequentially washed with water and saturated sodium chloride solution and dried over anhydrous magnesium sulfate, from which the solvents were distilled off. The residue was purified by silica gel column chromatography (100 g of silica gel; elution solvents:hexane:acetone=5:2), to preferentially recover 2,3-bis(methoxycarbonyl)-6-nitrophenol (1.34 g at a yield of 32%) as a yellow crystal from ether.

To a solution of the diester (1.27 g, 5 mmol) in THF (4 ml) and t-BuOH (4 ml) in mixture was added an aqueous solution of lithium hydroxide (420 mg, 10 mmol) at 0° C., with stirring at ambient temperature for 24 hours. The reaction solution was adjusted to acidity by using 2 N hydrochloric acid, and extracted with ethyl acetate. The organic layer was sequentially washed with water and saturated sodium chloride solution and dried over anhydrous magnesium sulfate, from which the solvents were distilled off, to recover 3-hydroxy-2-methoxycarbonyl-4-nitrobenzoic acid (728 mg at a yield of 60%) as a yellow crystal.

To a THF solution of the benzoic acid (650 mg, 2.7 mmol) was dropwise added borane (1.0 M THF solution, 8.1 ml, 8.1 mmol) at 0° C. under argon atmosphere, with stirring at ambient temperature for 24 hours. The reaction solution was diluted with water and adjusted to acidity by using 2 N hydrochloric acid, and extracted with ethyl acetate. The organic layer was sequentially washed with water and saturated sodium chloride solution and dried over anhydrous magnesium sulfate, from which the solvents were distilled off. The residue was purified by silica gel column chromatography (20 g of silica gel; elution solvents:chloroform:methanol=20:1), to recover 6-nitro-7-hydroxyphthalide (290 mg at a yield of 61%) as a yellow crystal.

To a solution of the nitrophthalide (290 mg, 1.5 mmol) in ethanol (20 ml) was added a catalyst 10% palladium-carbon (300 mg), and the resulting mixture was stirred at ambient temperature under hydrogen atmosphere for 3 hours. The reaction solution was subjected to filtration through celite. Potassium o-Ethyl dithiocarbonate (280 mg, 1.7 mmol) was added to the resulting filtrate, with stirring under heating for 16 hours. After the solution was left to stand and cooled, the solvents were distilled off under reduced pressure. The residue was diluted with 2 N hydrochloric acid to adjust the resulting solution to acidity, and extracted with ethyl acetate. The organic layer was sequentially washed with water and saturated sodium chloride solution, and was then dried over anhydrous magnesium sulfate, from which the solvents were distilled off. The residue was purified by silica gel column chromatography (15 g of silica gel; elution solvents:chloroform:methanol=20:1). The resulting solid was crystallized from acetone and hexane, to recover 2-mercaptooxazolo[4,5-g]phthalide (225 mg at a yield of 80%) as a colorless needle-like crystal.

In the same manner as in Example 1 except for the use of the phthalide herein recovered instead of 2-mercaptooxazolo [4,5-b]pyridine, reaction progressed to recover the objective compound as a colorless needle-like crystal.

Melting Point: 161–162° C. IR (KBr) cm$^{-1}$: 3243, 2959, 1768, 1647, 1263. 1H-NMR (d$_6$-DMSO) δ: 1.11 (12H, d, J=6.8 Hz), 1.56 (2H, m), 1.72 (2H, m), 1.89 (2H, m), 2.47 (2H, m), 3.08 (2H, sept, J=7.0 Hz), 3.40 (2H, t, J=7.0 Hz), 5.57 (2H, s), 7.09 (2H, d, J=7.4 Hz), 7.18 (1H, t, J=7.4 Hz), 7.78 (2H, m), 8.71 (1H, br, s). EIMS m/z (relative intensity): 480 (M$^+$), 162 (100). Elementary Analysis: C$_{27}$H$_{32}$N$_2$O$_4$S Required: C, 67.47; H, 6.71; N, 5.83; Found: C, 67.37; H, 6.75; N, 5.78;

Example 91

Production of 6-[6-hydroxy-7-methoxycarbonylbenzoxazol-2-ylthio)-N-(2,6-diisopropylphenyl)hexanamide In the same manner as in Example 77 except for the use of ethyl 2,6-dihydroxybenzoate instead of 2-tert-butylphenol, reaction progressed to recover the objective compound as a colorless crystal.

Melting Point: 155–156° C. IR (KBr) cm$^{-1}$: 3228, 2966, 1677, 1645, 1513. 1H-NMR (d$_6$-DMSO) δ: 1.11 (12H, d, J=6.8 Hz), 1.55 (2H, m), 1.71 (2H, m), 1.86 (2H, m), 2.35 (2H, m), 3.08 (2H, sept, J=7.0 Hz), 3.32 (2H, t, J=7.0 Hz), 3.97 (3H, s), 6.92 (1H, d, J=8.7 Hz), 7.09 (2H, d, J=7.4 Hz), 7.20 (1H, t, J=7.4 Hz), 7.67 (1H, d, J=8.7 Hz), 8.69 (1H, br, s). EIMS m/z (relative intensity): Elementary Analysis: $C_{27}H_{34}N_2O_5S \cdot 1/2H_2O$ Required: C, 63.88; H, 6.95; N, 5.52; Found: C, 63.93; H, 6.87; N, 5.37;

Example 92

Production of 6-[6,7-dihydro-7,7-dimethyloxazolo[4,5-g]benzofuran]-2-ylthio-N-(2,6-diisopropylphenyl)hexanamide In the same manner as in Example 77 except for the use of 2,3-dihydro-2,2-dimethyl-7-benzofuranol instead of 2-tert-butylphenol, reaction progressed to recover the objective compound as a colorless crystal.

Melting Point: 136–137° C. IR (KBr) cm$^{-1}$: 3417, 3249, 2984, 1648, 1509. 1H-NMR (d$_6$-DMSO) δ: 1.12 (12H, d, J=6.8 Hz), 1.49 (6H, s), 1.51–1.61 (2H, m), 1.66–1.76 (2H, m), 1.80–1.88 (2H, m), 2.36 (2H, t, J=6.6 Hz), 3.08 (2H, sept, J=6.8 Hz), 3.12 (2H, s), 3.33 (2H, t, J=7.1 Hz), 7.02 (2H, d, J=7.8 Hz), 7.09 (2H, d, J=7.8 Hz), 7.09 (2H, d, J=7.6 Hz), 7.19 (1H, t, J=7.6 Hz), 8.70 (1H, br s) EIMS m/z (relative intensity):494(M$^+$), 176(100) Elementary Analysis: $C_{29}H_{38}N_2O_3S$ Required: C, 70.41; H, 7.74; N, 5.66; Found: C, 70.36; H, 7.64; N, 5.75;

Industrial Applicability

As has been described above, the novel anilide compound of the invention is useful in the form of pharmaceutical composition, specifically as acyl coenzyme A cholesterol acyltransferase (ACAT) inhibitor.

What is claimed is:

1. A compound represented by the following formula IV, a salt thereof or a solvated product thereof:

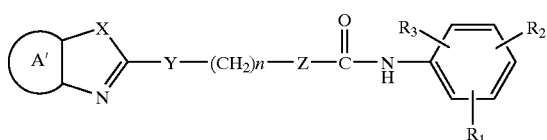

(IV)

wherein

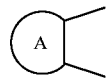

represents

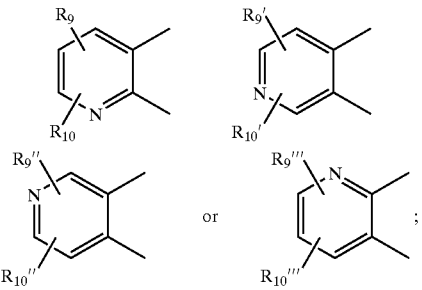

X represents —NH—, oxygen atom or sulfur atom;

Y represents —NR$_4$—, oxygen atom, sulfur atom, sulfoxide or sulfone;

Z represents single bond;

R$_1$, R$_2$ and R$_3$ may be the same or different and represent hydrogen atom, a lower alkyl group, a lower alkoxyl group, halogen atom, hydroxyl group, phosphate group, sulfonamide group, or amino group which may or may not have a substituent; otherwise, any combination of two of R$_1$, R$_2$ and R$_3$ represents an alkylene dioxy group;

R$_4$ represents hydrogen atom, a lower alkyl group, an aryl group or a silylated lower alkyl group which may or may not have a substituent; and R$_9$, R$_{10}$, R$_9'$, R$_{10}'$, R$_9''R_{10}''$, R$_9'''$, and R$_{10}'''$, may be the same or different and represent hydrogen atom, a lower alkyl group which may or may not have a substituent, a lower alkoxyl group which may or may not have a substituent, halogen atom, hydroxyl group, carboxyl group, an alkoxycarbonyl group which may or may not have a substituent, an alkylcarbonyloxy group which may or may not have a substituent, an alkylcarbonyl group which may or may not have a substituent, carbamoyl group which may or may not have a substituent, a hydroxyalkyl group, phosphate group, sulfonamide group, amino group which may or may not have a substituent, an aminoalkyl group which may or may not have a substituent, or a heterocyclic residue; otherwise, any combination of two thereof represents an alkylene dioxy group; and n represents an integer of 2 to 15;

with the proviso that when X is sulfur atom then

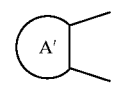

is not

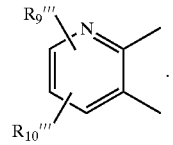

2. A pharmaceutical composition comprising a compound, a salt thereof or a solvated compound thereof according to claim 1, and a pharmaceutically acceptable carrier.

3. A pharmaceutical composition according to claim 2, which is an ACAT inhibitor, an intra-cellular cholesterol transfer inhibitory agent, a blood cholesterol-reducing agent or a macrophage foaming-suppressing agent.

4. A pharmaceutical composition according to claim 2, which is prophylactic and therapeutic agent of hyperlipidemia, arteriosclerosis, cerebrovascular diseases, ischemic cardiac diseases, ischemic intestinal diseases or aortic aneurysm.

5. A method for therapeutically treating diseases with the etiology of abnormal levels of ACAT, intra-cellular cholesterol transfer, blood cholesterol or macrophage foaming, comprising administering a therapeutically effective dose of a compound according to Formula (I), a salt thereof or a solvated compound thereof:

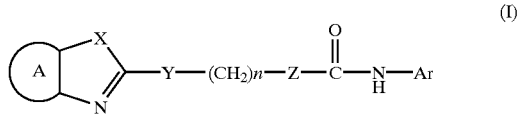

(I)

wherein

represents a divalent residue of pyridine which may or may not have a substituent; and Ar represents an aryl group which may or may not have a substituent;

X represents —NH—, oxygen atom or sulfur atom;

Y represents —NR$_4$—, oxygen atom, sulfur atom, sulfoxide or sulfone;

Z represents single bond;

R$_4$ represents hydrogen atom, a lower alkyl group, an aryl group or a silylated lower alkyl group which may or may not have a substituent; and n represents an integer of 1 to 15.

6. A method for therapeutically treating hyperlipidemia, arteriosclerosis, ischemic cardiac diseases, ischemic intestinal diseases or aortic aneurysm, comprising administering a therapeutically effective dose of a compound according to Formula (I), a salt thereof or a solvated compound thereof;

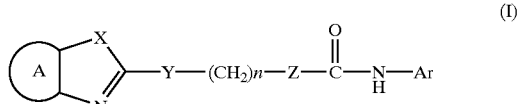

(I)

wherein

represents a divalent residue of pyridine which may or may not have a substituent;

Ar represents an aryl group which may or may not have a substituent;

x represents —NH—, oxygen atom or sulfur atom;

Y represents —NR$_4$, oxygen atom, sulfur atom, sulfoxide or sulfone;

Z represent single bond;

R$_4$ represents hydrogen atom, a lower alkyl group, an aryl group or a silylated lower alkyl group which ay or may not have a substituent; and n represents an integer of 1 to 15.

7. A method of claim 5 wherein the compound of Formula (I), salt thereof or solvated compound thereof is administered to a patient suffering from a disease having etiology of abnormal levels of ACAT intra-cellular cholesterol transfer, blood cholesterol or macrophage foaming.

8. A method of claim 5 wherein the compound of Formula (I), salt thereof or solvated compound thereof is administered to a patient suffering from a disease having etiology of abnormal levels of ACAT.

9. A method of claim 5 wherein the compound of Formula (I), salt thereof or solvated compound thereof is administered to a patient suffering from a disease associated with abnormal levels of intra-cellular cholesterol transfer.

10. A method of claim 5 wherein the compound of Formula (I), salt thereof or solvated compound thereof is administered to a patient suffering from a disease associated with abnormal levels of blood cholesterol or macrophage foaming.

11. A method of claim 5 wherein the compound of Formula (I), salt thereof or solvated compound thereof is administered to a patient suffering from a disease associate with abnormal levels of macrophage foaming.

12. A method of claim 6 wherein the compound of Formula (I), salt thereof or solvated compound thereof is administered to a patient suffering from hyperlipidemia, arteriosclerosis, an ischemic cardiac disease, an ischemic intestinal disease or aortic aneurysm.

13. A method of claim 6 wherein the compound of Formula (I), salt thereof or solvated compound thereof is administered to a patient suffering from hyperlipidemia.

14. A method of claim 6 wherein the compound of Formula (I), salt thereof or solvated compound thereof is administered to a patient suffering from arteriosclerosis.

15. A method of claim wherein the compound of Formula (I), salt thereof or solvated compound thereof is administered to a patient suffering from an ischemic cardiac disease.

16. A method of claim 6 wherein the compound of Formula (I), salt thereof or solvated compound thereof is administered to a patient suffering from an ischemic intestinal disease.

17. A method of claim 6 wherein the compound of Formula (I), salt thereof or solvated compound thereof is administered to a patient suffering from aortic aneurysm.

* * * * *